(12) United States Patent
Allan et al.

(10) Patent No.: US 9,854,982 B2
(45) Date of Patent: Jan. 2, 2018

(54) IMPLANTABLE MEDICAL DEVICE DEPLOYMENT WITHIN A VESSEL

(75) Inventors: James Calvin Allan, Santa Rosa, CA (US); Erik C. Griswold, Penngrove, CA (US); William J. Havel, West Lafayette, IN (US); Steven L. Waldhauser, Centerville, MN (US); Kelly M. Wien, Big Lake, MN (US); Kendra Yasger, Big Lake, MN (US); Rudolph A. Beasley, Rohnert Park, CA (US); Jon D. Schell, Shoreview, MN (US); Don H. Tran, Novato, CA (US)

(73) Assignee: Medtronic, Inc., Minneapolis, MN (US)

( * ) Notice: Subject to any disclaimer, the term of this patent is extended or adjusted under 35 U.S.C. 154(b) by 718 days.

(21) Appl. No.: 13/482,880

(22) Filed: May 29, 2012

(65) Prior Publication Data

US 2013/0253309 A1 Sep. 26, 2013

Related U.S. Application Data

(60) Provisional application No. 61/615,712, filed on Mar. 26, 2012.

(51) Int. Cl.
*A61B 5/0215* (2006.01)
*A61B 6/00* (2006.01)
(Continued)

(52) U.S. Cl.
CPC .......... *A61B 5/0215* (2013.01); *A61B 5/0031* (2013.01); *A61B 5/686* (2013.01);
(Continued)

(58) Field of Classification Search
CPC .... A61B 17/12172; A61B 2017/00243; A61B 2017/00867; A61B 18/24
(Continued)

(56) References Cited

U.S. PATENT DOCUMENTS 4,035,909 A 7/1977 Dey
4,103,690 A 8/1978 Harris
(Continued)

FOREIGN PATENT DOCUMENTS

WO 00/59376 A1 10/2000
WO WO 01/66151 A1 9/2001
(Continued)

OTHER PUBLICATIONS

Medtronic, Inc., "Cardiac Resynchronization Therapy for Heart Failure Management—Implant and Follow-up—Brief Overview" 4 pages (2002).
(Continued)

*Primary Examiner* — Rochelle Turchen

(57) ABSTRACT

In one example, this disclosure is directed to a method for intravascular implantation of an implantable medical device comprising positioning a distal end of an elongated outer sheath forming an inner lumen adjacent a target site within a vasculature of a patient, and partially deploying an implantable medical device from the distal opening, wherein the implantable medical device includes an expandable fixation element. A portion of the expandable fixation element assumes an expanded position when the implantable medical device is partially deployed from the distal opening. The method including advancing the distal end of the outer sheath within the vasculature with the implantable medical device partially deployed from the distal opening, and monitoring at least one of the vasculature and the portion of the expandable fixation element for deflection to determine when the size of the portion of the expandable fixation element corresponds to the size of the vasculature.

21 Claims, 30 Drawing Sheets

(51) Int. Cl.
*A61B 5/00* (2006.01)
*A61M 25/04* (2006.01)
*A61B 5/042* (2006.01)
*A61N 1/365* (2006.01)

(52) U.S. Cl.
CPC .............. *A61B 6/00* (2013.01); *A61B 5/042* (2013.01); *A61M 25/04* (2013.01); *A61N 1/36564* (2013.01)

(58) Field of Classification Search
USPC ............... 600/407, 420, 423, 424, 431, 434; 623/1.11, 1.12, 2.1
See application file for complete search history.

(56) References Cited

U.S. PATENT DOCUMENTS

| | | |
|---|---|---|
| 4,112,952 A | 9/1978 | Thomas et al. |
| 4,376,811 A | 3/1983 | Goebel |
| 4,494,531 A | 1/1985 | Gianturco |
| 4,727,873 A | 3/1988 | Mobin-Uddin |
| 4,729,384 A | 3/1988 | Bazenet |
| 4,731,305 A | 5/1988 | Goebel et al. |
| 5,002,067 A | 3/1991 | Berthelsen et al. |
| 5,024,239 A | 6/1991 | Rosenstein |
| 5,098,393 A | 3/1992 | Amplatz et al. |
| 5,249,574 A | 10/1993 | Bush et al. |
| 5,255,678 A | 10/1993 | Deslauriers et al. |
| 5,255,679 A | 10/1993 | Imran |
| 5,265,608 A | 11/1993 | Lee et al. |
| 5,282,845 A | 2/1994 | Bush et al. |
| 5,306,581 A | 4/1994 | Taylor et al. |
| 5,314,462 A | 5/1994 | Heil, Jr. et al. |
| 5,324,316 A | 6/1994 | Schulman et al. |
| 5,358,514 A | 10/1994 | Schulman et al. |
| 5,383,922 A | 1/1995 | Zipes et al. |
| 5,387,233 A | 2/1995 | Alferness et al. |
| 5,492,119 A | 2/1996 | Abrams |
| 5,540,734 A | 7/1996 | Zabara |
| 5,545,219 A | 8/1996 | Kuzma |
| 5,562,723 A | 10/1996 | Rugland et al. |
| 5,766,234 A | 6/1998 | Chen et al. |
| 5,776,632 A | 7/1998 | Honegger |
| 5,814,089 A | 9/1998 | Stokes et al. |
| 5,824,041 A | 10/1998 | Lenker et al. |
| 5,840,076 A | 11/1998 | Swanson et al. |
| 5,860,974 A | 1/1999 | Abele |
| 5,895,391 A | 4/1999 | Farnholtz |
| 5,897,584 A | 4/1999 | Herman |
| 5,968,052 A | 10/1999 | Sullivan et al. |
| 5,984,944 A | 11/1999 | Ferber |
| 6,024,752 A | 2/2000 | Horn et al. |
| 6,074,401 A | 6/2000 | Gardiner et al. |
| 6,113,593 A | 9/2000 | Tu et al. |
| 6,120,480 A | 9/2000 | Zhang et al. |
| 6,136,005 A | 10/2000 | Goode et al. |
| 6,149,658 A | 11/2000 | Gardiner et al. |
| 6,183,305 B1 | 2/2001 | Doan et al. |
| 6,238,813 B1 | 5/2001 | Maile et al. |
| 6,258,098 B1 | 7/2001 | Taylor et al. |
| 6,266,568 B1 | 7/2001 | Mann et al. |
| 6,270,489 B1 | 8/2001 | Wise et al. |
| 6,308,105 B1 | 10/2001 | Duysens et al. |
| 6,322,586 B1 | 11/2001 | Monroe et al. |
| 6,350,278 B1 | 2/2002 | Lenker et al. |
| 6,352,561 B1 | 3/2002 | Leopold et al. |
| 6,395,017 B1 | 5/2002 | Dwyer et al. |
| 6,434,431 B1 | 8/2002 | Camps et al. |
| 6,468,301 B1 | 10/2002 | Amplatz et al. |
| 6,477,423 B1 | 11/2002 | Jenkins |
| 6,498,951 B1 | 12/2002 | Larson et al. |
| 6,505,075 B1 | 1/2003 | Weiner |
| 6,510,332 B1 | 1/2003 | Greenstein |
| 6,514,265 B2 | 2/2003 | Ho et al. |
| 6,529,777 B1 | 3/2003 | Holmström et al. |
| 6,551,332 B1 | 4/2003 | Nguyen et al. |
| 6,582,400 B1 | 6/2003 | Hawk et al. |
| 6,585,634 B1 | 7/2003 | Henckel et al. |
| 6,589,238 B2 | 7/2003 | Edwards et al. |
| 6,600,955 B1 | 7/2003 | Zierhofer |
| 6,607,541 B1 | 8/2003 | Gardiner et al. |
| 6,607,843 B2 | 8/2003 | Ruth, II et al. |
| 6,613,059 B2 | 9/2003 | Schaller et al. |
| 6,623,518 B2 | 9/2003 | Thompson et al. |
| 6,626,916 B1 | 9/2003 | Yeung et al. |
| 6,641,593 B1 | 11/2003 | Schaller et al. |
| 6,645,143 B2 | 11/2003 | VanTassel et al. |
| 6,679,902 B1 | 1/2004 | Boyle et al. |
| 6,689,056 B1 | 2/2004 | Kilcoyne et al. |
| 6,695,859 B1 | 2/2004 | Golden et al. |
| 6,743,219 B1 | 6/2004 | Dwyer et al. |
| 6,840,956 B1 | 1/2005 | Wolinsky et al. |
| 6,866,650 B2 | 3/2005 | Stevens et al. |
| 6,876,885 B2 | 4/2005 | Swoyer et al. |
| 6,889,093 B1 | 5/2005 | Flammang |
| 6,895,283 B2 | 5/2005 | Erickson et al. |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,932,837 B2 | 8/2005 | Amplatz et al. |
| 6,960,221 B2 | 11/2005 | Ho et al. |
| 7,047,084 B2 | 5/2006 | Erickson et al. |
| 7,054,692 B1 | 5/2006 | Whitehurst et al. |
| 7,060,038 B2 | 6/2006 | Letort et al. |
| 7,070,881 B2 | 7/2006 | Kishiyama et al. |
| 7,072,703 B2 | 7/2006 | Zhang et al. |
| 7,099,718 B1 | 8/2006 | Thacker et al. |
| 7,128,765 B2 | 10/2006 | Paulot et al. |
| 7,147,604 B1 | 12/2006 | Allen et al. |
| 7,172,620 B2 | 2/2007 | Gilson |
| 7,177,702 B2 | 2/2007 | Wallace et al. |
| 7,181,288 B1 | 2/2007 | Rezai et al. |
| 7,236,821 B2 | 6/2007 | Cates et al. |
| 7,288,096 B2 | 10/2007 | Chin |
| 7,291,186 B2 | 11/2007 | Zhang |
| 7,294,334 B1 | 11/2007 | Michal et al. |
| 7,309,349 B2 | 12/2007 | Jackson et al. |
| 7,364,541 B2 | 4/2008 | Chu et al. |
| 7,410,512 B2 | 8/2008 | Tsukamoto et al. |
| 7,473,266 B2 | 1/2009 | Glaser |
| 7,499,758 B2 | 3/2009 | Cates et al. |
| 7,572,228 B2 | 8/2009 | Wolinsky et al. |
| 7,678,128 B2 | 3/2010 | Boyle et al. |
| 7,699,059 B2 | 4/2010 | Fonseca et al. |
| 7,704,245 B2 | 4/2010 | Dittman et al. |
| 7,717,854 B2 | 5/2010 | Mann et al. |
| 7,740,655 B2 | 6/2010 | Birdsall |
| 7,765,014 B2 | 7/2010 | Eversull et al. |
| 7,769,420 B2 | 8/2010 | Silver et al. |
| 7,776,080 B2 | 8/2010 | Bei et al. |
| 7,783,338 B2 | 8/2010 | Ainsworth et al. |
| 7,785,360 B2 | 8/2010 | Freitag |
| 7,797,053 B2 | 9/2010 | Atkinson et al. |
| 7,801,626 B2 | 9/2010 | Moser |
| 7,871,430 B2 | 1/2011 | Pavcnik et al. |
| 7,963,952 B2 | 6/2011 | Wright, Jr. et al. |
| 8,062,327 B2 | 11/2011 | Chanduszko et al. |
| 8,352,028 B2 | 1/2013 | Wenger |
| 8,496,614 B2 | 7/2013 | Birk et al. |
| 8,715,332 B2 | 5/2014 | Tan et al. |
| 9,125,765 B2 | 9/2015 | Mesheimer |
| 9,339,197 B2 | 5/2016 | Griswold et al. |
| 2001/0002300 A1 | 5/2001 | Tinker et al. |
| 2001/0047181 A1 | 11/2001 | Ho et al. |
| 2002/0010490 A1 | 1/2002 | Schaller et al. |
| 2002/0082610 A1 | 6/2002 | Cioanta et al. |
| 2002/0103521 A1 | 8/2002 | Swoyer et al. |
| 2002/0111659 A1 | 8/2002 | Davis et al. |
| 2002/0120250 A1 | 8/2002 | Altman |
| 2002/0147485 A1 | 10/2002 | Mamo et al. |
| 2002/0156513 A1 | 10/2002 | Borkan |
| 2002/0195872 A1 | 12/2002 | Weiner |
| 2002/0198572 A1 | 12/2002 | Weiner |

(56) References Cited

U.S. PATENT DOCUMENTS

| | | |
|---|---|---|
| 2003/0004537 A1 | 1/2003 | Boyle et al. |
| 2003/0036790 A1 | 2/2003 | Corbett, III et al. |
| 2003/0045901 A1 | 3/2003 | Opolski |
| 2003/0069623 A1 | 4/2003 | Stypulkowski |
| 2003/0078603 A1 | 4/2003 | Schaller et al. |
| 2003/0088301 A1 | 5/2003 | King |
| 2003/0093118 A1 | 5/2003 | Ho et al. |
| 2003/0093130 A1 | 5/2003 | Stypulkowski |
| 2003/0120328 A1 | 6/2003 | Jenkins et al. |
| 2003/0125790 A1 | 7/2003 | Fastovsky et al. |
| 2003/0199974 A1 | 10/2003 | Lee et al. |
| 2004/0059393 A1 | 3/2004 | Policker et al. |
| 2004/0093053 A1 | 5/2004 | Gerber et al. |
| 2004/0101746 A1 | 5/2004 | Ota et al. |
| 2004/0102797 A1 | 5/2004 | Golden et al. |
| 2004/0111099 A1 | 6/2004 | Nguyen et al. |
| 2004/0111139 A1 | 6/2004 | McCreery |
| 2004/0116878 A1 | 6/2004 | Byrd et al. |
| 2004/0116992 A1 | 6/2004 | Wardle et al. |
| 2004/0148007 A1 | 7/2004 | Jackson et al. |
| 2004/0176782 A1 | 9/2004 | Hanse et al. |
| 2004/0181206 A1 | 9/2004 | Chiu et al. |
| 2004/0185337 A1 | 9/2004 | Ishizaki |
| 2004/0193229 A1 | 9/2004 | Starkebaum et al. |
| 2004/0215230 A1 | 10/2004 | Frazier et al. |
| 2004/0230279 A1 | 11/2004 | Cates et al. |
| 2004/0243206 A1 | 12/2004 | Tadlock |
| 2005/0015129 A1 | 1/2005 | Mische |
| 2005/0021054 A1 | 1/2005 | Ainsworth et al. |
| 2005/0060014 A1 | 3/2005 | Swoyer et al. |
| 2005/0065601 A1 | 3/2005 | Lee et al. |
| 2005/0070924 A1 | 3/2005 | Schaller et al. |
| 2005/0090884 A1 | 4/2005 | Honeck |
| 2005/0096718 A1 | 5/2005 | Gerber et al. |
| 2005/0102006 A1 | 5/2005 | Whitehurst et al. |
| 2005/0107861 A1 | 5/2005 | Harris et al. |
| 2005/0107862 A1 | 5/2005 | Ohlenschlaeger |
| 2005/0149141 A1 | 7/2005 | Starkebaum |
| 2005/0149142 A1 | 7/2005 | Starkebaum |
| 2005/0154321 A1 | 7/2005 | Wolinsky et al. |
| 2005/0171479 A1 | 8/2005 | Hruska et al. |
| 2005/0209653 A1 | 9/2005 | Herbert et al. |
| 2005/0221054 A1 | 10/2005 | Kawano et al. |
| 2005/0222632 A1 | 10/2005 | Obino |
| 2005/0245840 A1 | 11/2005 | Christopherson et al. |
| 2005/0245986 A1 | 11/2005 | Starkebaum |
| 2005/0246004 A1 | 11/2005 | Cameron et al. |
| 2005/0267487 A1 | 12/2005 | Christensen et al. |
| 2005/0287859 A1 | 12/2005 | Eigler et al. |
| 2005/0288596 A1 | 12/2005 | Eigler et al. |
| 2006/0047205 A1 | 3/2006 | Ludomirsky et al. |
| 2006/0057458 A1 | 3/2006 | O'Dea et al. |
| 2006/0069422 A9 | 3/2006 | Bolduc et al. |
| 2006/0079943 A1 | 4/2006 | Narcisco, Jr. |
| 2006/0079950 A1 | 4/2006 | Lehnhardt et al. |
| 2006/0085041 A1 | 4/2006 | Hastings et al. |
| 2006/0085042 A1 | 4/2006 | Hastings et al. |
| 2006/0085971 A1 | 4/2006 | Andrews et al. |
| 2006/0099238 A1 | 5/2006 | Khosravi et al. |
| 2006/0100686 A1 | 5/2006 | Bolduc et al. |
| 2006/0149324 A1 | 7/2006 | Mann et al. |
| 2006/0149330 A1 | 7/2006 | Mann et al. |
| 2006/0206163 A1 | 9/2006 | Wahlstrand et al. |
| 2006/0206165 A1 | 9/2006 | Jaax et al. |
| 2006/0206166 A1 | 9/2006 | Weiner |
| 2006/0212096 A1 | 9/2006 | Stevenson |
| 2006/0222942 A1 | 10/2006 | Zhao et al. |
| 2006/0241733 A1 | 10/2006 | Zhang et al. |
| 2006/0259128 A1 | 11/2006 | Pavcnik et al. |
| 2006/0271137 A1 | 11/2006 | Stanton-Hicks |
| 2006/0275659 A1 | 12/2006 | Kim et al. |
| 2007/0027514 A1 | 2/2007 | Gerber |
| 2007/0027515 A1 | 2/2007 | Gerber |
| 2007/0043414 A1 | 2/2007 | Fifer et al. |
| 2007/0043424 A1 | 2/2007 | Pryor |
| 2007/0073391 A1 | 3/2007 | Bourang et al. |
| 2007/0088230 A1 | 4/2007 | Terashi et al. |
| 2007/0088396 A1 | 4/2007 | Jacobson |
| 2007/0088418 A1 | 4/2007 | Jacobson |
| 2007/0129637 A1 | 6/2007 | Wolinsky et al. |
| 2007/0135826 A1* | 6/2007 | Zaver et al. ................. 606/157 |
| 2007/0150020 A1 | 6/2007 | Hokanson et al. |
| 2007/0154801 A1 | 7/2007 | Hyung et al. |
| 2007/0156126 A1 | 7/2007 | Flaherty et al. |
| 2007/0179552 A1 | 8/2007 | Dennis et al. |
| 2007/0197939 A1 | 8/2007 | Wallace et al. |
| 2007/0219590 A1 | 9/2007 | Hastings et al. |
| 2007/0247786 A1 | 10/2007 | Aamodt et al. |
| 2007/0255295 A1 | 11/2007 | Starkebaum et al. |
| 2007/0255383 A1 | 11/2007 | Gerber et al. |
| 2007/0274565 A1 | 11/2007 | Penner |
| 2007/0276461 A1 | 11/2007 | Andreas et al. |
| 2007/0293090 A1 | 12/2007 | Engelmeyer et al. |
| 2007/0293909 A1 | 12/2007 | Cowan et al. |
| 2007/0293922 A1 | 12/2007 | Soltis et al. |
| 2007/0299492 A1 | 12/2007 | Zhang et al. |
| 2008/0009750 A1 | 1/2008 | Aeby et al. |
| 2008/0051704 A1 | 2/2008 | Patel et al. |
| 2008/0071178 A1 | 3/2008 | Greenland et al. |
| 2008/0077227 A1 | 3/2008 | Ouellette et al. |
| 2008/0103578 A1 | 5/2008 | Gerber |
| 2008/0125844 A1 | 5/2008 | Swoyer et al. |
| 2008/0132981 A1 | 6/2008 | Gerber |
| 2008/0132982 A1 | 6/2008 | Gerber |
| 2008/0148554 A1 | 6/2008 | Merrill et al. |
| 2008/0172118 A1 | 7/2008 | Johnson et al. |
| 2008/0255475 A1 | 10/2008 | Kondrosky et al. |
| 2008/0262422 A1 | 10/2008 | Cahill |
| 2008/0275350 A1 | 11/2008 | Liao et al. |
| 2008/0283066 A1 | 11/2008 | Delgado et al. |
| 2008/0300672 A1* | 12/2008 | Kassab et al. ............... 623/1.15 |
| 2009/0043367 A1 | 2/2009 | Zilberman et al. |
| 2009/0082828 A1 | 3/2009 | Ostroff |
| 2009/0082843 A1 | 3/2009 | Cox et al. |
| 2009/0099641 A1 | 4/2009 | Wu et al. |
| 2009/0105799 A1 | 4/2009 | Hekmat et al. |
| 2009/0131970 A1 | 5/2009 | Chanduszko et al. |
| 2009/0157092 A1 | 6/2009 | Blumenkranz |
| 2009/0163969 A1 | 6/2009 | Donofrio |
| 2009/0177095 A1 | 7/2009 | Aeby et al. |
| 2009/0192514 A1 | 7/2009 | Feinberg et al. |
| 2009/0192585 A1 | 7/2009 | Bloom et al. |
| 2009/0192601 A1 | 7/2009 | Rafiee et al. |
| 2009/0234367 A1 | 9/2009 | Verma |
| 2009/0270741 A1 | 10/2009 | Vanney et al. |
| 2009/0275818 A1 | 11/2009 | Rau et al. |
| 2009/0299429 A1 | 12/2009 | Mayotte |
| 2009/0306539 A1 | 12/2009 | Woodruff et al. |
| 2009/0326346 A1 | 12/2009 | Kracker et al. |
| 2010/0004730 A1 | 1/2010 | Benjamin et al. |
| 2010/0030063 A1 | 2/2010 | Lee et al. |
| 2010/0030139 A1 | 2/2010 | Copa |
| 2010/0057009 A1 | 3/2010 | McQueen et al. |
| 2010/0063478 A1 | 3/2010 | Selkee |
| 2010/0076398 A1 | 3/2010 | Scheurer et al. |
| 2010/0082087 A1 | 4/2010 | Silipo et al. |
| 2010/0094400 A1 | 4/2010 | Bolduc et al. |
| 2010/0168612 A1 | 7/2010 | Ducharme et al. |
| 2010/0179561 A1 | 7/2010 | Pilarski et al. |
| 2010/0185172 A1 | 7/2010 | Fabro |
| 2010/0234698 A1 | 9/2010 | Manstrom et al. |
| 2010/0274221 A1 | 10/2010 | Sigg et al. |
| 2010/0274227 A1 | 10/2010 | Khairkhahan et al. |
| 2010/0274345 A1 | 10/2010 | Rust |
| 2010/0304209 A1 | 12/2010 | Lund et al. |
| 2010/0305653 A1 | 12/2010 | Lund et al. |
| 2011/0077708 A1 | 3/2011 | Ostroff |
| 2011/0160557 A1 | 6/2011 | Cinbis et al. |
| 2011/0190842 A1 | 8/2011 | Johnson et al. |
| 2011/0220274 A1 | 9/2011 | Erskine et al. |
| 2011/0251662 A1 | 10/2011 | Griswold et al. |
| 2011/0264194 A1 | 10/2011 | Griswold |

(56) References Cited

U.S. PATENT DOCUMENTS

| | | |
|---|---|---|
| 2011/0313503 A1 | 12/2011 | Berra et al. |
| 2012/0029598 A1 | 2/2012 | Zhao |
| 2012/0172690 A1 | 7/2012 | Anderson |
| 2012/0172691 A1 | 7/2012 | Lee |
| 2012/0172891 A1 | 7/2012 | Lee |
| 2012/0172892 A1 | 7/2012 | Grubac et al. |
| 2013/0253309 A1 | 9/2013 | Allan et al. |
| 2013/0253346 A1 | 9/2013 | Griswold et al. |

FOREIGN PATENT DOCUMENTS

| | | |
|---|---|---|
| WO | WO 02/30295 A1 | 4/2002 |
| WO | 03/084398 A1 | 10/2003 |
| WO | 2004014456 A2 | 2/2004 |
| WO | WO 2004/014456 A2 | 2/2004 |
| WO | 2005028023 A1 | 3/2005 |
| WO | 2007021340 A1 | 2/2007 |
| WO | 2007022180 A1 | 2/2007 |
| WO | 2009039400 A1 | 3/2009 |
| WO | WO 2009/120636 A1 | 10/2009 |
| WO | WO 2009/124287 A1 | 10/2009 |
| WO | 10/088687 A1 | 5/2010 |

OTHER PUBLICATIONS

Luna Technologies, "About Distributed Sensing Technology" 2 pages (2010).
Rozenman et al., "Wireless Acoustic Communication With a Miniature Pressure Sensor in the Pulmonary Artery for Disease Surveillance and Therapy of Patients With Congestive Heart Failure," J Am Coll Cardiol 2007;49:784-9.
U.S. Appl. No. 13/074,948, by Nathan T. Lee, filed Mar. 29, 2011.
U.S. Appl. No. 13/096,881, by Vladimir Grubac, filed Apr. 28, 2011.
U.S. Appl. No. 13/197,072, by Rudy Beasley, filed Aug. 3, 2011.
U.S. Appl. No. 13/284,761, by Thomas A. Anderson, filed Oct. 28, 2011.
U.S. Appl. No. 13/482,816, by Erik C. Griswold, filed May 29, 2012.
U.S. Appl. No. 13/482,684, by Erik C. Griswold, filed May 29, 2012.
U.S. Appl. No. 13/482,738, by Steven L. Waldhauser, filed May 29, 2012.
U.S. Appl. No. 13/482,839, by Erik C. Griswold, filed May 29, 2012.
U.S. Appl. No. 13/482,883, by Erik C. Griswold, filed May 29, 2012.
U.S. Appl. No. 13/482,923, by Erik C. Griswold, filed May 29, 2012.

* cited by examiner

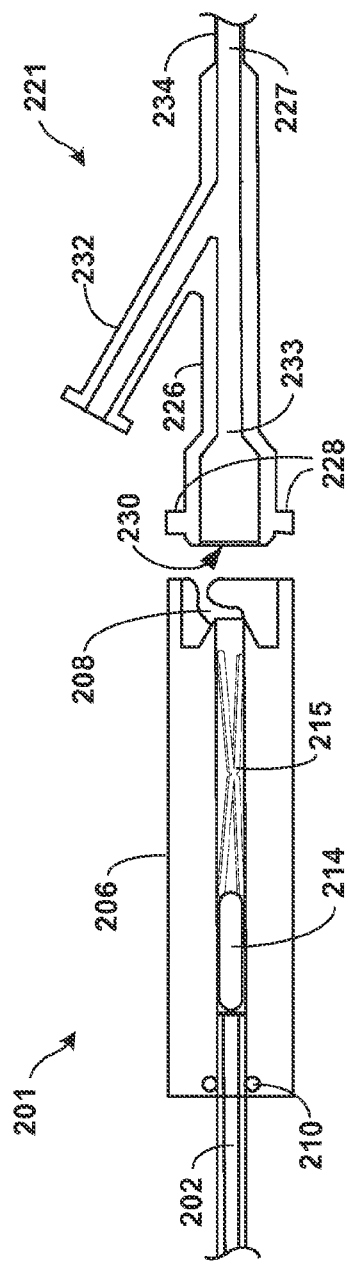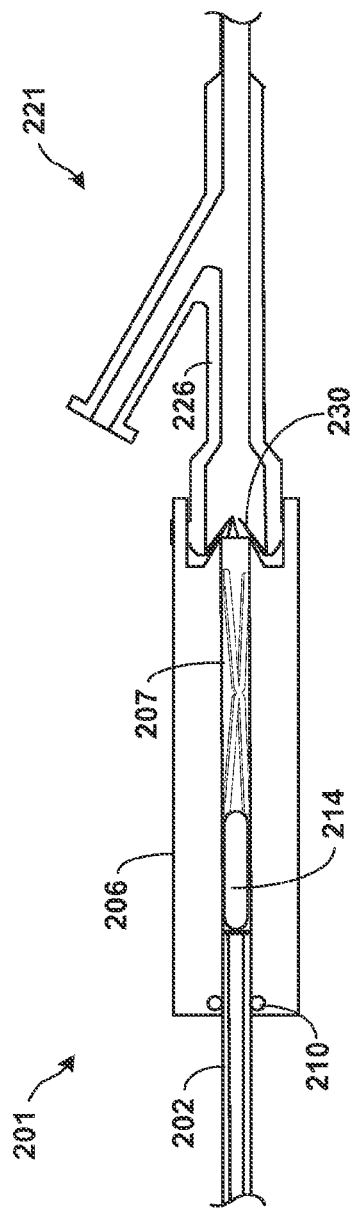

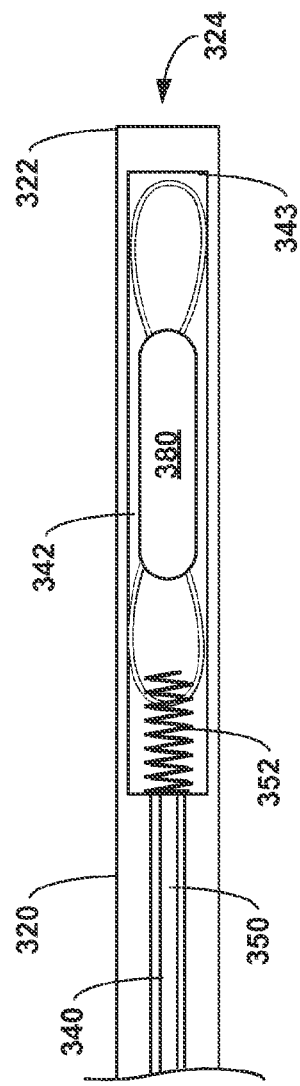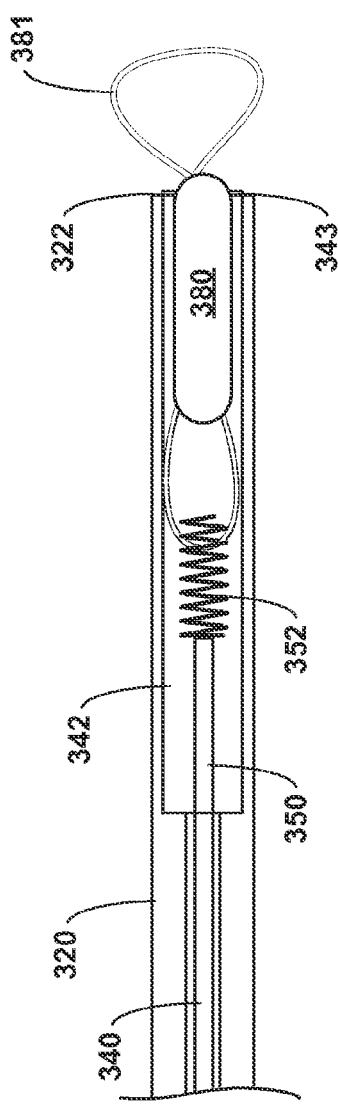
FIG. 10A
FIG. 10B

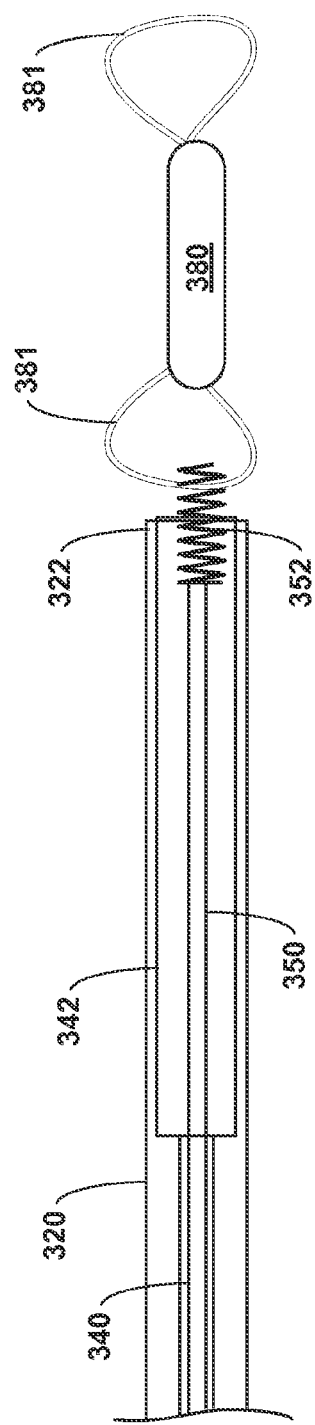
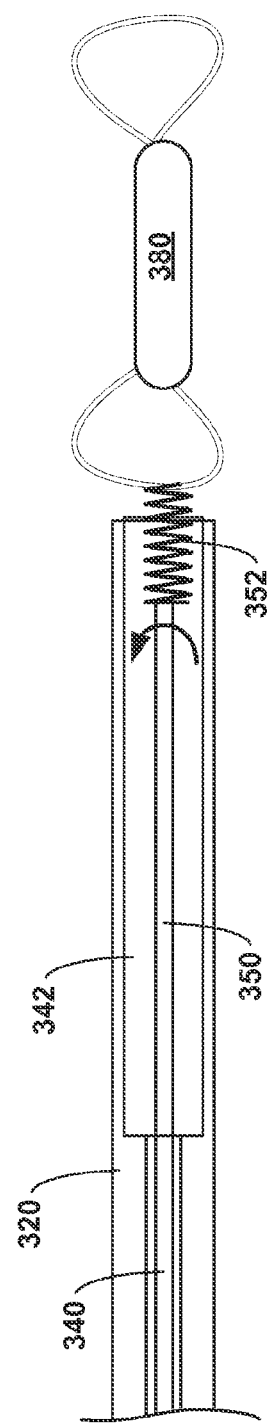
FIG. 10C
FIG. 10D

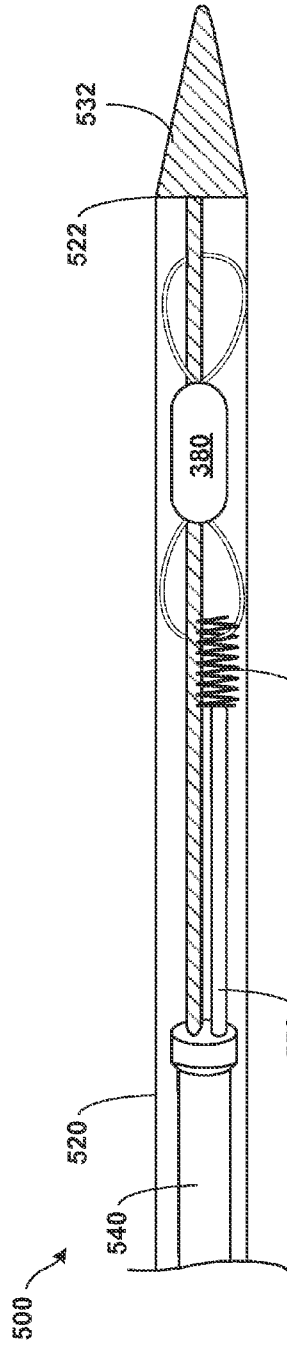
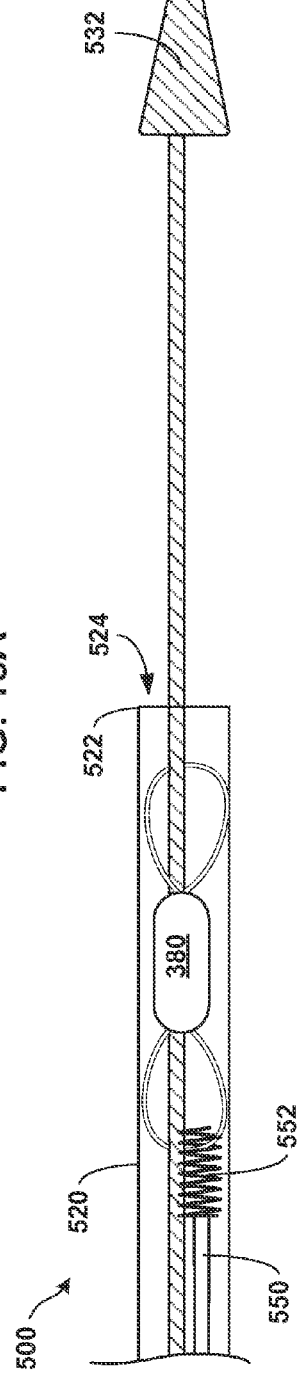
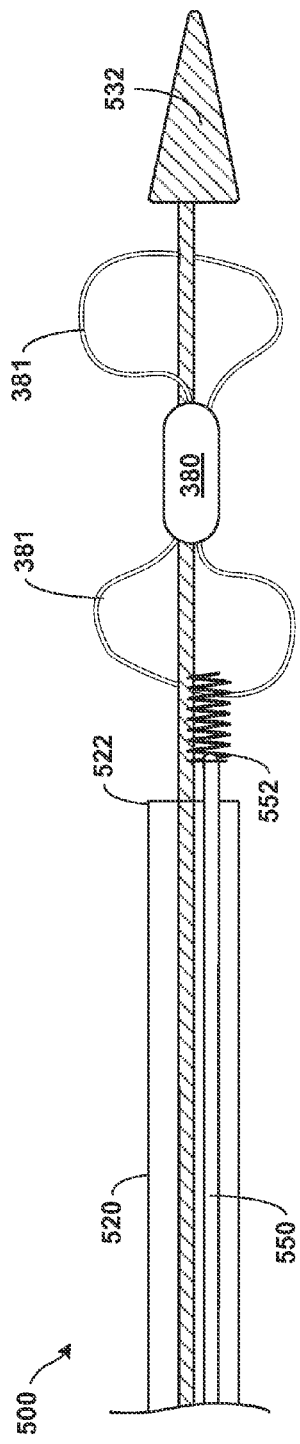
FIG. 15A
FIG. 15B
FIG. 15C

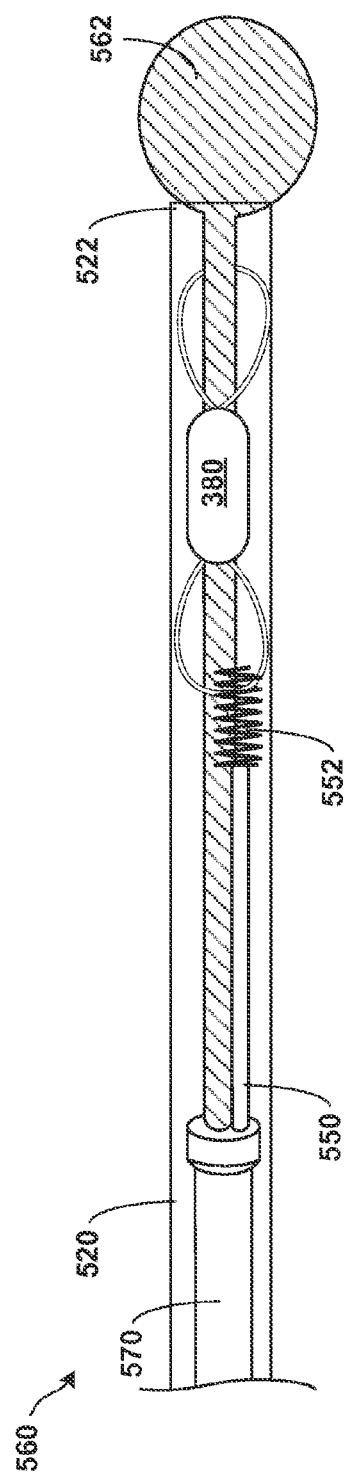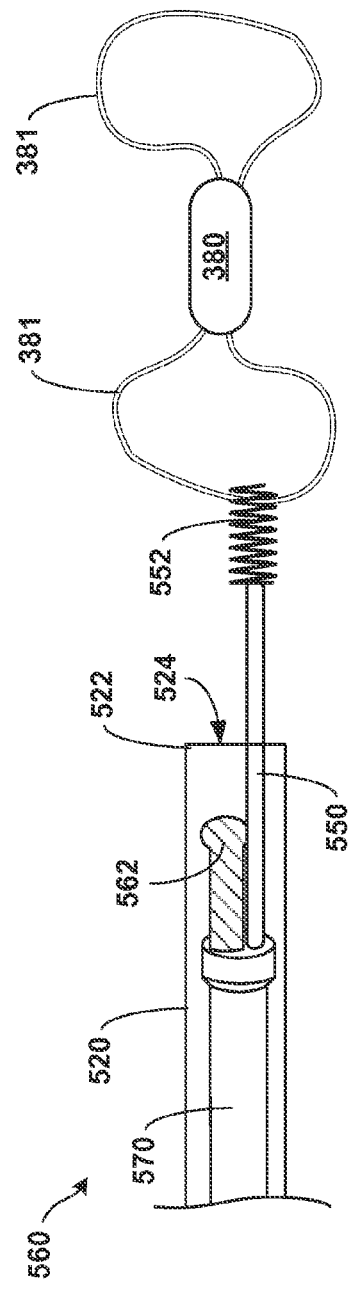

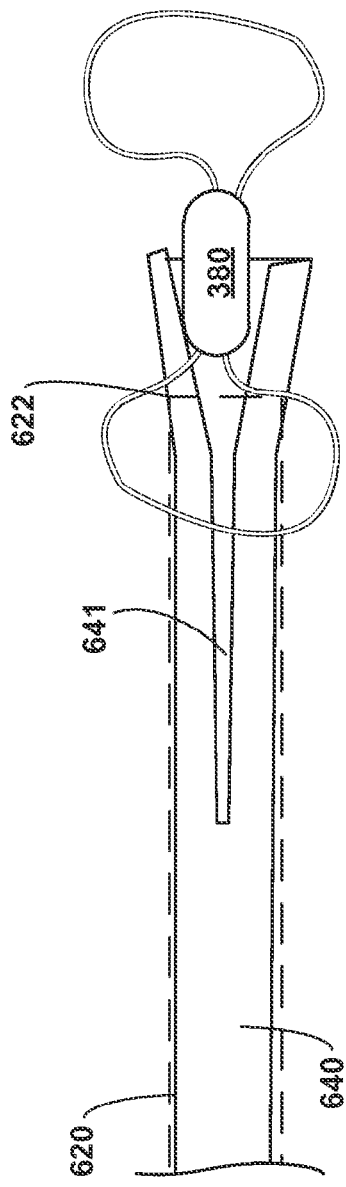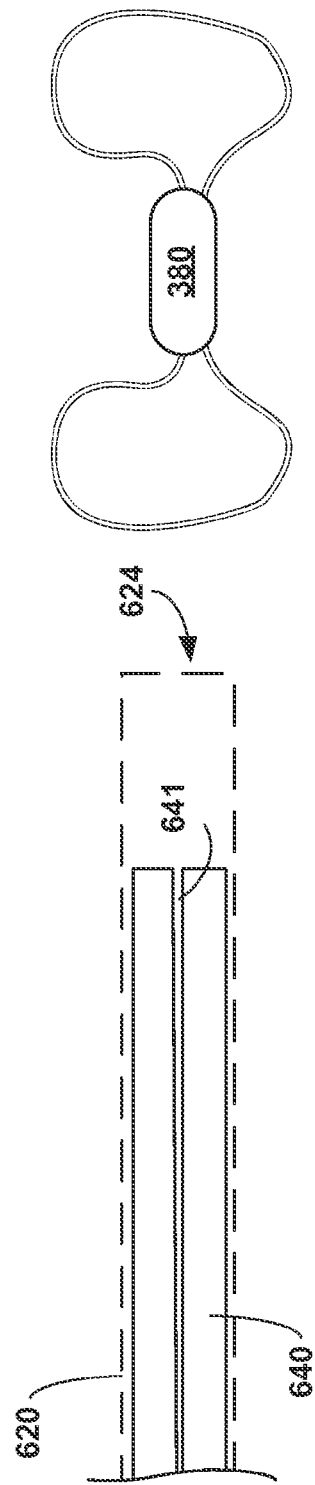
FIG. 17D
FIG. 17E

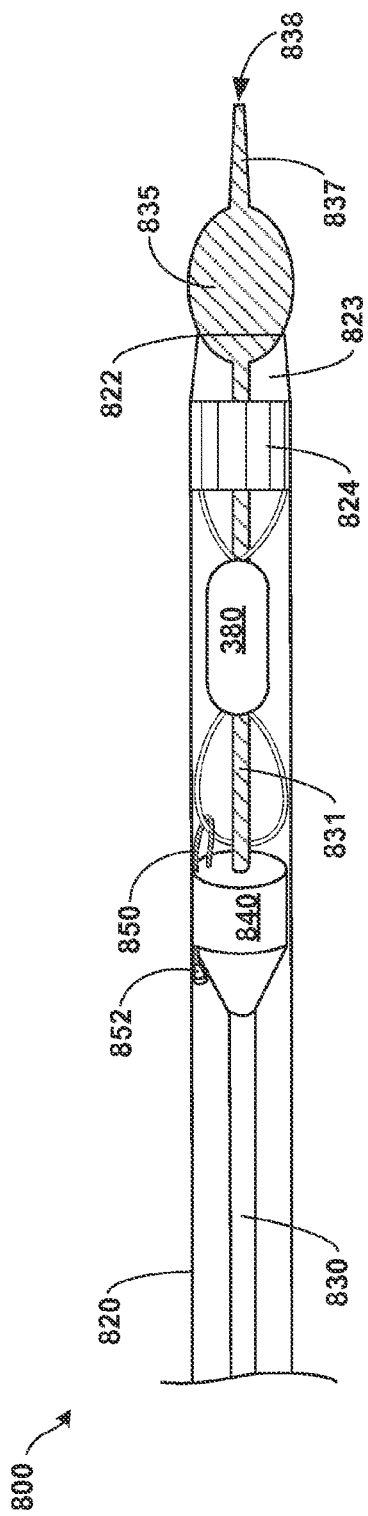
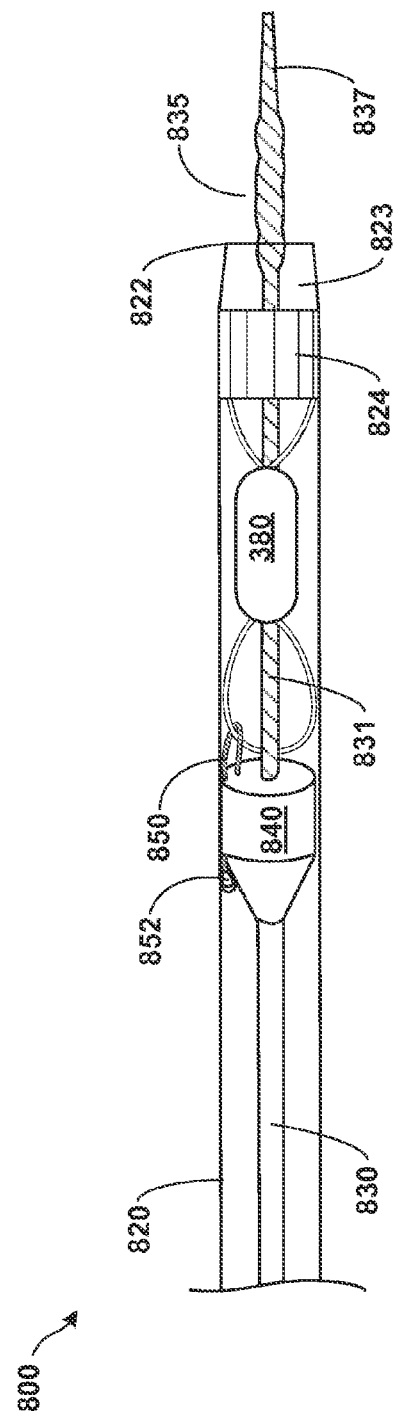
FIG. 23A
FIG. 23B

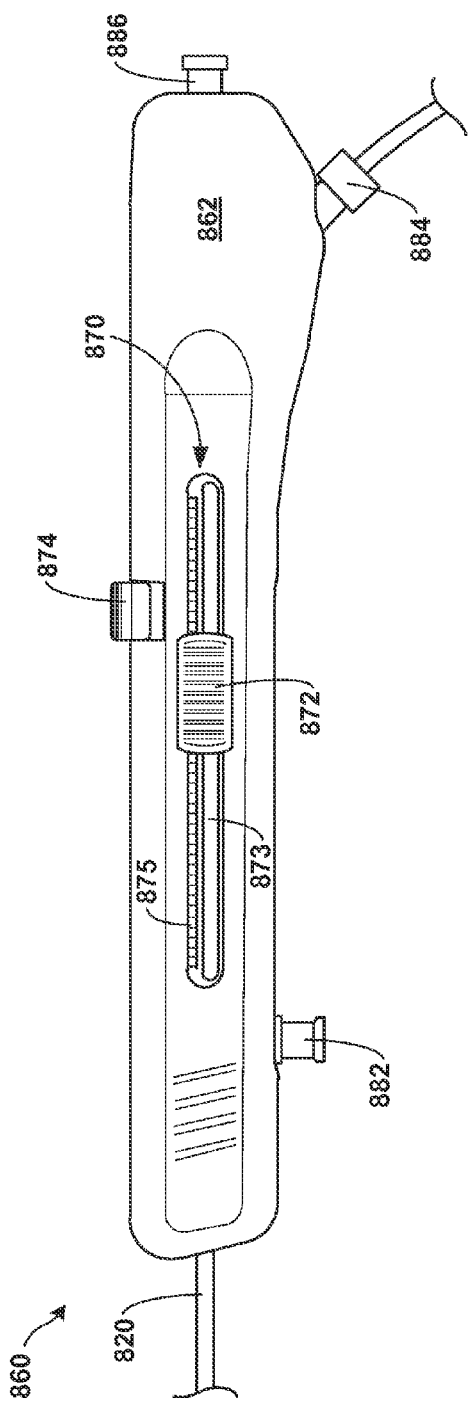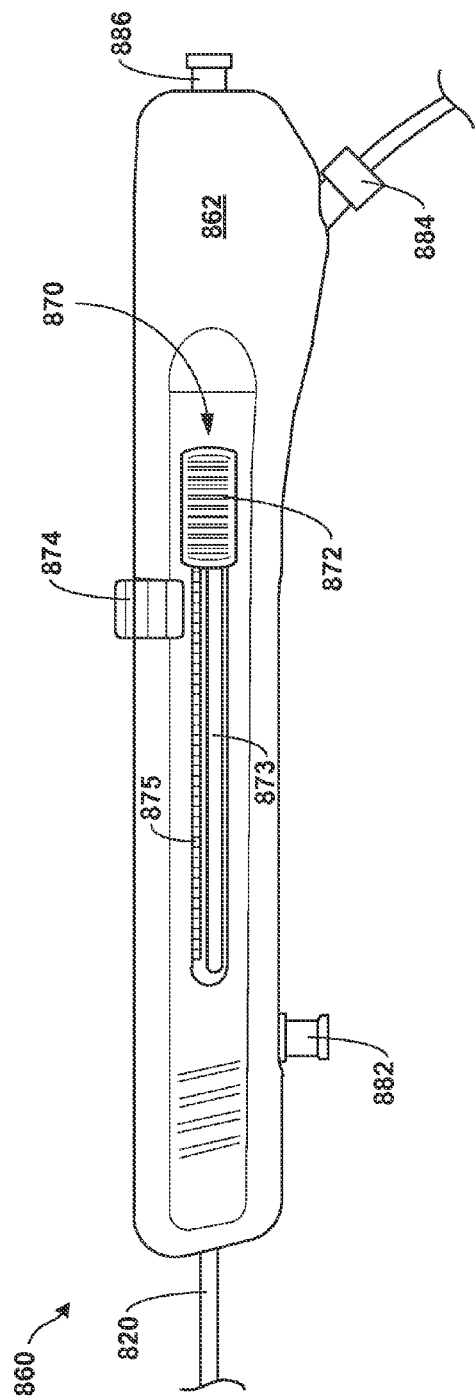
FIG. 24B
FIG. 24C

IMPLANTABLE MEDICAL DEVICE DEPLOYMENT WITHIN A VESSEL

This application claims the benefit of U.S. Provisional Patent Application No. 61/615,712, filed Mar. 26, 2012, the entire content of which is incorporated by reference herein.

TECHNICAL FIELD

This disclosure relates to delivery and deployment techniques for implantable medical devices.

BACKGROUND

Various implantable medical devices (IMDs) may be used for therapeutically treating or monitoring one or more physiological conditions of a patient. Such IMDs may be adapted to monitor or treat conditions or functions relating to heart, blood vessels, muscle, nerve, brain, stomach, endocrine organs or other organs and their related functions. Advances in design and manufacture of miniaturized IMDs have resulted in IMDs capable of therapeutic as well as diagnostic functions such as pacemakers, cardioverters, defibrillators, biochemical sensors, pressure sensors, various endovascular IMDs and the like. Such IMDs may have electronic functions and may be associated with electrical leads or may be wireless, with the ability to transmit data electronically either to another IMD implanted in the patient or to another device located externally of the patient, or both. Other IMDs may have purely mechanical and/or pharmaceutical functions, such as stents.

Although implantation of some IMDs requires a surgical procedure (e.g., pacemakers, defibrillators, etc.) other IMDs may be small enough to be delivered and placed at an intended deployment site in a relatively noninvasive manner, such as by a delivery catheter introduced percutaneously. Delivery also may be accomplished by advancing a catheter intravascularly through an exposed vasculature during a surgical procedure.

SUMMARY

In different examples, this disclosure describes techniques for remote deployment of IMDs.

In one example, this disclosure is directed to a kit for intravascular implantation of an implantable medical device within a patient, the kit comprising an elongated inner sheath with a distal end, a first coupling module slidably connected to the inner sheath, an elongated outer sheath forming an inner lumen with a distal opening and a proximal opening, the outer sheath sized to traverse a vasculature of the patient. The proximal opening is configured to receive the distal end of the inner sheath. The inner lumen is sized to receive the inner sheath and to contain the implantable medical device. The kit further comprises a mating coupling module secured to a proximal end of the outer sheath. The mating coupling module is configured to connect to the first coupling module such that the inner sheath is axially aligned with the outer sheath. The inner sheath is slidable within the outer sheath while the first coupling module is connected to the mating coupling module.

In another example, this disclosure is directed to a method for intravascular implantation of an implantable medical device within a patient comprising positioning a distal end of an elongated outer sheath via a vasculature of the patient proximate to a target site within the patient. The outer sheath forms an inner lumen with a distal opening and a proximal opening. The method further includes connecting a first coupling module that is slidably connected to an elongated inner sheath with a mating coupling module secured to a proximal end of the outer sheath. The mating coupling module is configured to connect to the first coupling module such that the inner sheath is axially aligned with the outer sheath. The inner sheath has a distal end. An implantable medical device is positioned in the inner lumen of the outer sheath. The method further includes pushing the implantable medical device through the inner lumen of the outer sheath and out of the distal opening with the inner sheath to deploy the implantable medical device proximate to the target site within the patient.

In a different example, this disclosure is directed to a kit for intravascular implantation of an implantable medical device within a patient, the kit comprising an elongated outer sheath forming an inner lumen with a distal opening and a proximal opening, the outer sheath sized to traverse a vasculature of the patient. The kit further includes an elongated inner sheath with a tapered distal end. The tapered distal end is configured to substantially fill the inner lumen of the outer sheath and close-off the distal opening of the outer sheath. The inner sheath is slidable within the inner lumen of the outer sheath. The inner sheath is selectably removable from the inner lumen of the outer sheath by sliding the inner sheath out of the proximal opening of the outer sheath. The kit further includes an elongated deployment receptacle including a deployment bay at a distal end of the deployment receptacle. The deployment receptacle is slidable within the inner lumen of the outer sheath when the inner sheath is not within the inner lumen of the outer sheath. The deployment bay is configured to carry an implantable medical device through the inner lumen of the outer sheath and facilitate deployment of the implantable medical device out of the distal opening of the outer sheath.

In another example, this disclosure is directed to a method for intravascular implantation of an implantable medical device within a patient comprising positioning a distal end of an elongated outer sheath via a vasculature of the patient proximate to a target site within the patient. The outer sheath forms an inner lumen with a distal opening and a proximal opening. The method further includes inserting an elongated deployment receptacle including a deployment bay at a distal end of the deployment receptacle into the proximal opening of the outer sheath. An implantable medical device is positioned within deployment bay, sliding the deployment receptacle through the inner lumen of the outer sheath until the deployment bay is adjacent to the distal opening of the outer sheath, and deploying the implantable medical device from the deployment bay proximate to the target site within the patient.

In a different example, this disclosure is directed to a kit for intravascular implantation of an implantable medical device within a patient, the kit comprising an elongated outer sheath forming an inner lumen with a distal opening, the outer sheath sized to traverse a vasculature of the patient. The kit further includes an elongated inner sheath with an inflatable member at a distal portion of the inner sheath. The inflatable member is selectively inflatable from a proximal end of the inner sheath. The inflatable member is configured to substantially fill the inner lumen and close-off the distal opening of the outer sheath when inflated. The inner sheath is slidable within the inner lumen of the outer sheath. The inner sheath further includes a stopper proximally located relative to the inflatable member. The inflatable member is remotely controllable from a proximal end of the inner sheath to retract in a proximal direction towards the stopper.

The kit is configured such that the inflatable member can be retracted in a proximal direction towards the stopper and past an implantable medical device positioned within a distal portion of the outer sheath.

In another example, this disclosure is directed to a method for intravascular implantation of an implantable medical device within a patient comprising positioning a distal end of an assembly including an elongated outer sheath and an elongated inner sheath via a vasculature of the patient proximate to a target site within the patient. The outer sheath forms an inner lumen with a distal opening. The inner sheath includes an inflatable member at a distal portion of the inner sheath. The inflatable member is selectively inflatable from a proximal end of the inner sheath. The inflatable member is inflated to substantially fill the inner lumen and close-off the distal opening of the outer sheath. The inner sheath further includes a stopper proximally located relative to the inflatable member. The inner sheath is slidable within the inner lumen of the outer sheath. The method further includes deflating the inflatable member, and retracting the inflatable member in a proximal direction towards the stopper and past an implantable medical device that is positioned within a distal portion of the outer sheath.

In a different example, this disclosure is directed to a kit for intravascular implantation of an implantable medical device within a patient, the kit comprising an elongated outer sheath forming an inner lumen with a distal opening, the outer sheath sized to traverse a vasculature of the patient. The kit further includes an elongated inner sheath with an enlarged distal portion. The enlarged distal portion is configured to substantially fill the inner lumen and close-off the distal opening of the outer sheath. The enlarged distal portion is slidable relative to the outer sheath. The inner sheath further includes a tether with a helical element that is remotely controllable from a proximal end of the inner sheath to release the implantable medical device from a distal portion of the outer sheath.

In another example, this disclosure is directed to a method for intravascular implantation of an implantable medical device within a patient comprising positioning a distal end of an assembly including an elongated outer sheath and an elongated inner sheath via a vasculature of the patient proximate to a target site within the patient. The outer sheath forms an inner lumen with a distal opening. The inner sheath includes enlarged distal portion. The enlarged distal portion substantially fills the inner lumen to close-off the distal opening of the outer sheath. The enlarged distal portion is slidable relative to the outer sheath. The inner sheath further includes a tether with a helical element. The method further includes releasing an implantable medical device from a distal portion of the outer sheath by remotely rotating the helical element such that the helical element releases a looped element of the implantable medical device.

In a different example, this disclosure is directed to a kit for intravascular implantation of an implantable medical device within a patient, the kit comprising an elongated outer sheath forming a first inner lumen with a distal opening, the outer sheath sized to traverse a vasculature of the patient. The kit further includes an elongated inner sheath forming a second inner lumen. An outer diameter of the inner sheath is smaller than the diameter of the first inner lumen such that the inner sheath fits within the first inner lumen. The inner sheath is slidable within the first inner lumen. The second inner lumen at a distal end of the inner sheath is configured to carry an implantable medical device. The inner sheath forms a slit at a distal end of the inner sheath to facilitate deployment of the implantable medical device out of the distal opening of the outer sheath.

In another example, this disclosure is directed to a method for intravascular implantation of an implantable medical device within a patient comprising positioning a distal end of an assembly including an elongated outer sheath and an elongated inner sheath via a vasculature of the patient proximate to a target site within the patient. The outer sheath forms an inner lumen with a distal opening. The inner sheath forms a second inner lumen. An outer diameter of the inner sheath is smaller than the diameter of the first inner lumen such that the inner sheath fits within the first inner lumen. The inner sheath is slidable within the first inner lumen. Assembly further includes an implantable medical device carried within the second inner lumen at a distal end of the inner sheath. The inner sheath forms a slit at a distal end of the inner sheath to facilitate deployment of the implantable medical device out of the distal opening of the outer sheath. The method further includes sliding the distal end of the inner sheath out of the first inner lumen to expose a portion of the inner sheath and a portion of the implantable medical device out of the distal end of the outer sheath.

In a different example, this disclosure is directed to a method for intravascular implantation of an implantable medical device within a patient comprising positioning a distal end of an elongated outer sheath forming an inner lumen with a distal opening adjacent a target site within a vasculature of a patient, partially deploying an implantable medical device from the distal opening. The implantable medical device includes an expandable fixation element expandable from a collapsed position to an expanded position, wherein at least a portion of the expandable fixation element assumes the expanded position when the implantable medical device is partially deployed from the distal opening. The method further comprises advancing the distal end of the outer sheath within the vasculature with the implantable medical device partially deployed from the distal opening, monitoring at least one of the vasculature and the portion of the expandable fixation element for deflection to determine when the size of the portion of the expandable fixation element corresponds to the size of the vasculature.

In a different example, this disclosure is directed to a kit for intravascular implantation of an implantable medical device within a patient, the kit comprising an elongated outer sheath forming an inner lumen with a distal opening, the outer sheath sized to traverse a vasculature of the patient. The kit further includes an elongated inner sheath with a stopper configured engage a proximal side of the implantable medical device to preclude the implantable medical device from being located at a more proximal position than the stopper within the inner lumen of the outer sheath. The inner sheath further includes a tether configured to form a loop on a distal side of the stopper, the loop being configured to engage a looped element of the implantable medical device to couple the implantable medical device to the inner sheath. The stopper is slidable relative to the outer sheath between a position that is proximally located relative to the distal opening of the outer sheath and a position in which at least a portion of the stopper is distally located relative to the distal opening of the outer sheath. The tether is configured to release the looped element of the implantable medical device from the inner sheath by opening the tether loop when the at least a portion of the stopper is located distally relative to the distal opening of the outer sheath.

In another example, this disclosure is directed to a kit for intravascular implantation of an implantable medical device within a patient, the kit comprising an elongated outer sheath forming an inner lumen with a distal opening. The outer sheath sized to traverse a vasculature of the patient. The inner lumen is sized to hold the implantable medical device. The kit further includes an elongated inner sheath with a distal end. The inner sheath is located within the inner lumen of the outer sheath, and a deployment handle located at proximal ends of the outer sheath and the inner sheath. The deployment handle includes a sheath retraction mechanism that facilitates selectively retracting the outer sheath relative to the inner sheath to facilitate remote deployment of the implantable medical device out of the distal opening of the inner lumen of the outer sheath.

In another example, this disclosure is directed to a method for intravascular implantation of an implantable medical device within a patient comprising positioning a distal end of an assembly including an elongated outer sheath and an elongated inner sheath via a vasculature of the patient proximate to a target site within the patient. The outer sheath forms an inner lumen with a distal opening. The inner sheath includes a stopper configured to engage a proximal side of the implantable medical device to preclude the implantable medical device from being located at a more proximal position than the stopper within the inner lumen of the outer sheath. The inner sheath further includes a tether forming a loop on a distal side of the stopper, the loop being in engagement with a looped element of the implantable medical device to couple the implantable medical device to the inner sheath within the inner lumen of the outer sheath. The method further comprises retracting the outer sheath relative to the inner sheath such that the implantable medical device exits the inner lumen via the distal opening.

BRIEF DESCRIPTION OF DRAWINGS

FIGS. 10A-10D illustrate example techniques for intravascular delivery of an IMD through a sheath using a deployment receptacle.

FIGS. 15A-15F illustrate example techniques for intravascular delivery of an IMD using a delivery catheter with a slidable inner sheath including an enlarged distal portion and a tether.

FIGS. 16A-16B illustrate example techniques for intravascular delivery of an IMD using a delivery catheter with a slidable inner sheath including an inflatable distal portion and a tether.

FIGS. 17A-17E illustrate example techniques for intravascular delivery of an IMD using an inner sheath being configured to carry an IMD at its distal end, the inner sheath forming a slit at its distal end to facilitate deployment of the IMD.

DETAILED DESCRIPTION

Figure 1:
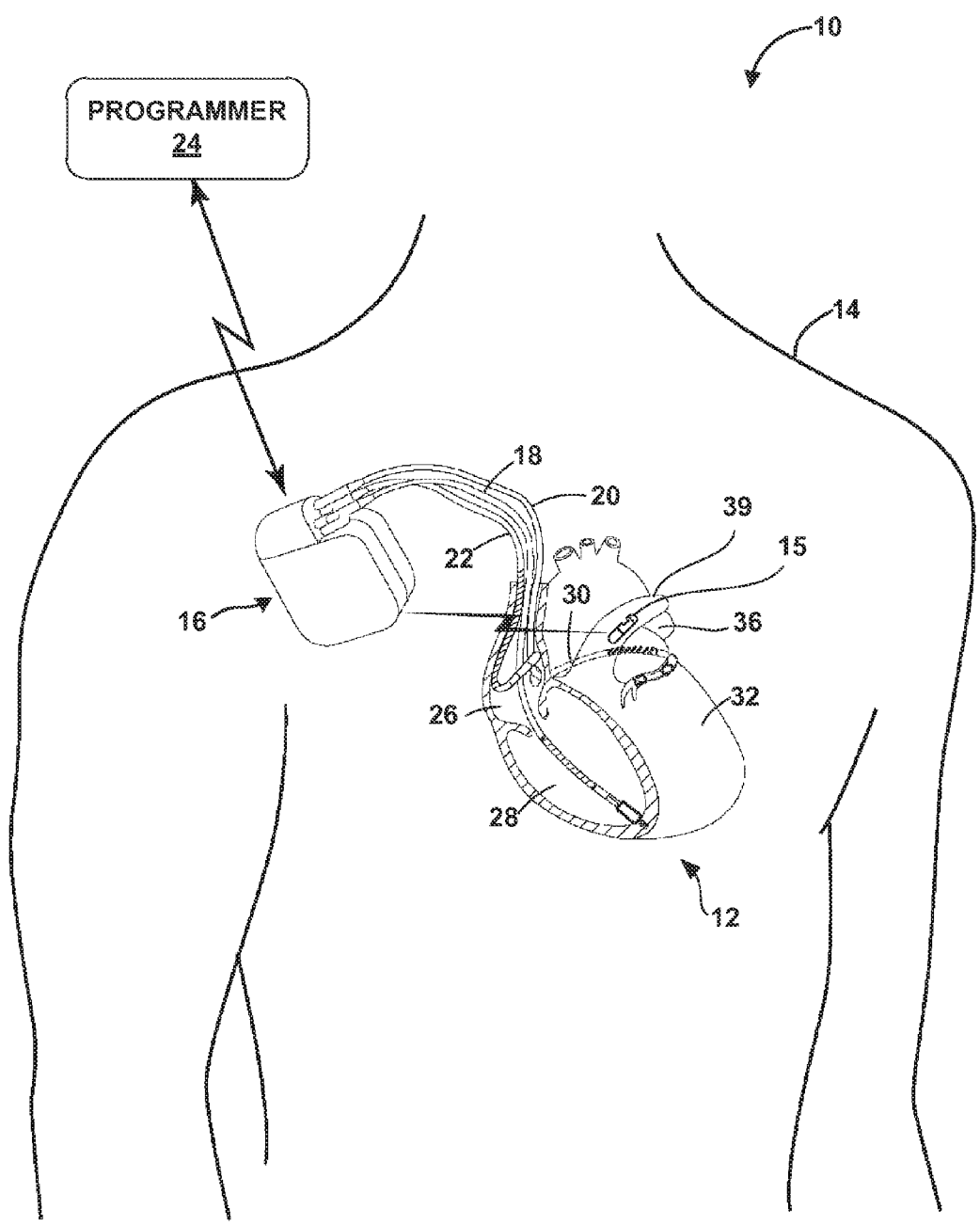
FIG. 1 is a conceptual drawing illustrating an example system that includes an implantable medical device (IMD) coupled to implantable medical leads and a leadless sensor.

FIG. 1 is a conceptual diagram illustrating an example medical system 10 that may be used for sensing of physiological parameters of patient 14 and/or to provide therapy to heart 12 of patient 14. Medical system 10 includes an IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily, a human patient.

IMD 16 may include electronics and other internal components necessary or desirable for executing the functions associated with the device. In one example, IMD 16 includes one or more processors, memory, a signal generator, sensing module and telemetry modules, and a power source. In general, memory of IMD 16 may include computer-readable instructions that, when executed by a processor of the IMD, cause it to perform various functions attributed to the device herein. For example, a processor of IMD 16 may control the signal generator and sensing module according to instructions and/or data stored on memory to deliver therapy to patient 14 and perform other functions related to treating condition(s) of the patient with IMD 16.

The signal generator of IMD 16 may generate electrical stimulation that is delivered to patient 12 via electrode(s) on one or more of leads 18, 20, and 22, in order to provide, e.g., cardiac sensing, pacing signals, or cardioversion/defibrillation shocks.

The sensing module of IMD 16 may monitor electrical signals from electrode(s) on leads 18, 20, and 22 of IMD 16 in order to monitor electrical activity of heart 12, such as electrocardiogram depolarizations of heart 12. In one example, the sensing module may include a switch module to select which of the available electrodes on leads 18, 20, and 22 of IMD 16 are used to sense the heart activity. Additionally, the sensing module of IMD 16 may include multiple detection channels, each of which includes an amplifier, as well as an analog-to-digital converter for digitizing the signal received from a sensing channel for, e.g., electrogram signal processing by a processor of the IMD.

A telemetry module of IMD 16 may include any suitable hardware, firmware, software or any combination thereof for communicating with another device, such as programmer 24. Under the control of a processor of IMD 16, the telemetry module may receive downlink telemetry from and send uplink telemetry to programmer 24 with the aid of an antenna, which may be internal and/or external.

The various components of IMD 16 may be coupled to a power source, which may include a rechargeable or non-rechargeable battery. A non-rechargeable battery may be capable of holding a charge for several years, while a rechargeable battery may be inductively charged from an external device, e.g., on a daily or weekly basis.

Leads 18, 20, 22 extend into the heart 12 of patient 14 to facilitate sensing of electrical activity of heart 12 and/or delivery of electrical stimulation to heart 12 by IMD 16, or to allow other sensors or transducers attached to the leads to make measurements. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

Figure 5:
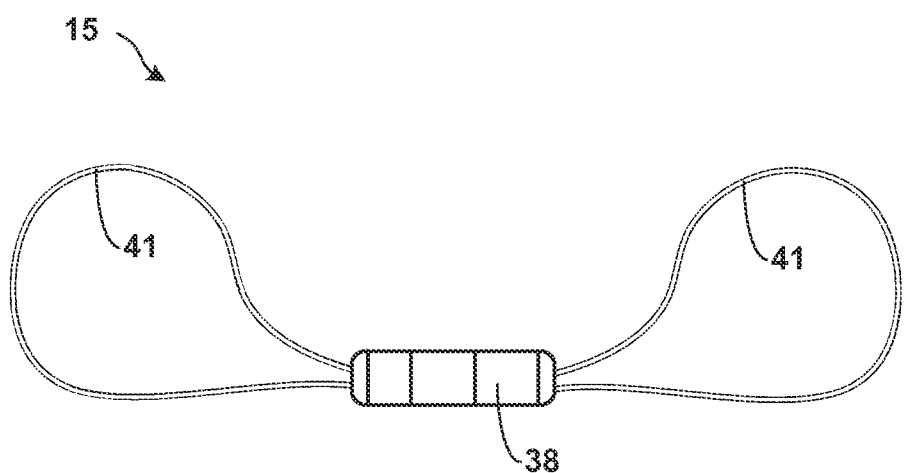
FIG. 5 illustrates a leadless IMD including an expandable fixation element configured for securing the leadless IMD within a vasculature.

System 10 also includes IMD 15, which includes a vascular sensor 38 (FIG. 5). While referred to as including a vascular sensor, IMD 15 could be within a chamber of the heart, or generally within the circulatory system. In the illustrated example, IMD 15 is implanted in pulmonary artery 39. In one example, IMD 15 is configured to sense blood pressure of patient 14. For example, IMD 15 may be arranged in pulmonary artery 39 and be configured to sense the pressure of blood flowing from the right ventricle outflow tract (RVOT) from right ventricle 28 through the pulmonary valve to pulmonary artery 39. IMD 15 may therefore directly measure the pulmonary artery diastolic pressure (PAD) of patient 14. The PAD value is a pressure value that can be employed in patient monitoring. For example, PAD may be used as a basis for evaluating congestive heart failure in a patient.

In other examples, however, IMD 15 may be employed to measure blood pressure values other than PAD. For example, IMD 15 may be arranged in right ventricle 28 of heart 14 to sense RV systolic or diastolic pressure. As shown in FIG. 1, IMD 15 is positioned in the main trunk of pulmonary artery 39. In other examples, a sensor, such as IMD 15 may be either positioned in the right or left pulmonary artery beyond the bifurcation of the pulmonary artery.

Moreover, the placement of IMD 15 is not restricted necessarily to the pulmonary side of the circulation. It could potentially be placed in the systemic side of the circulation—e.g., under certain conditions and with appropriate safety measures, it could even be placed in the left atrium, left ventricle, or aorta. Additionally, IMD 15 is not restricted to placement within the cardiovascular system. For example, the sensor might be placed in the renal circulation. IMD 15 placed in the renal circulation may be beneficial, for example, in circumstances in which IMD 16 is configured to treat heart failure based on some estimate of the degree of renal insufficiency in the patient derived from the monitoring of pressure or some other indication of renal circulation by the sensor. In this or other non-cardiovascular examples, the sensor may still communicate with IMD 16, or one or more sensors on leads 18, 20, or 22.

In some examples, IMD 15 includes a pressure sensor configured to respond to the absolute pressure inside pulmonary artery 39 of patient 14. IMD 15 may be, in such examples, any of a number of different types of pressure sensors. One form of pressure sensor that may be useful for measuring blood pressure is a capacitive pressure sensor. Another example pressure sensor is an inductive sensor. In some examples, IMD 15 may also comprise a piezoelectric or piezoresistive pressure transducer. In some examples, IMD 15 may comprise a flow sensor.

Figure 2:
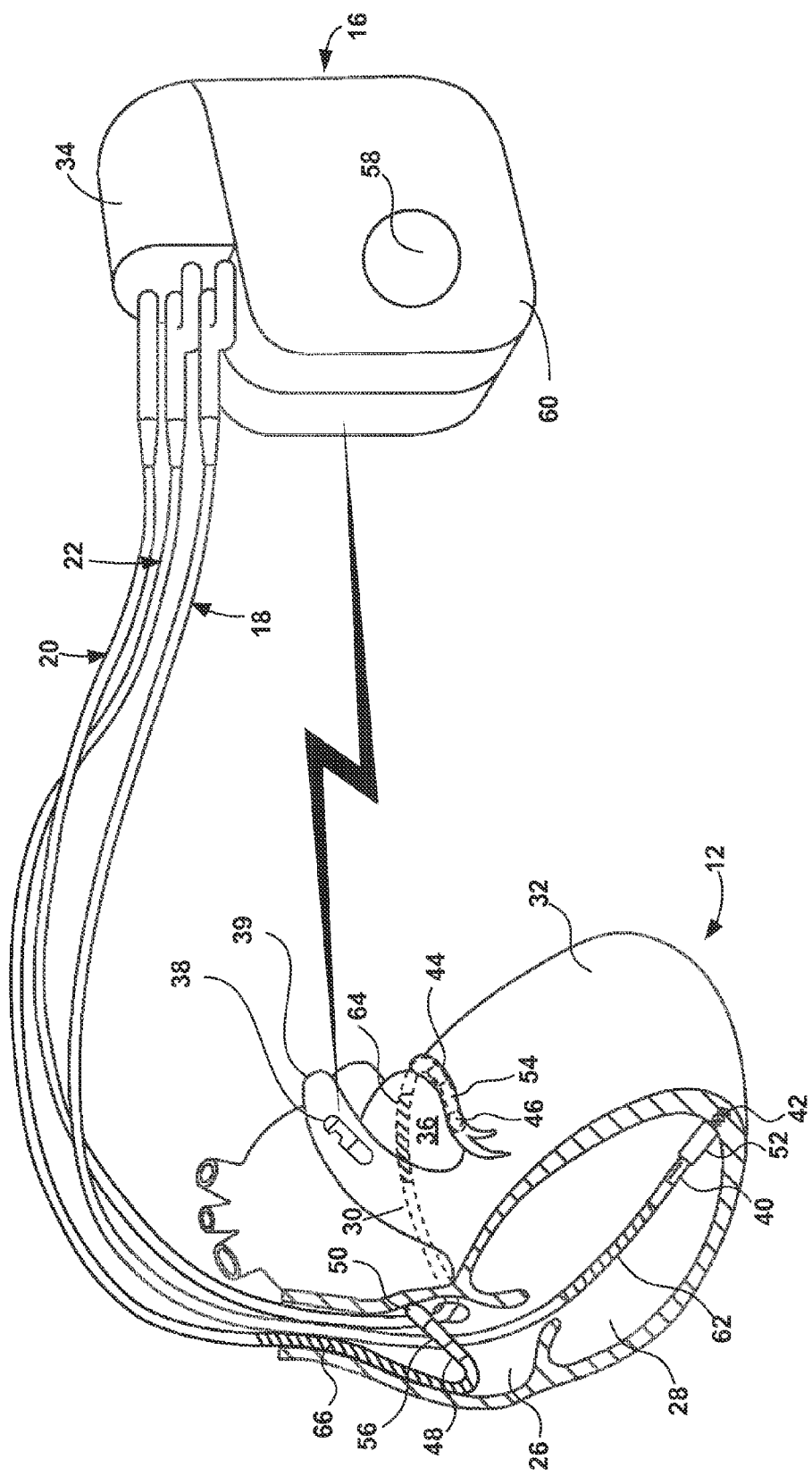
FIG. 2 is a conceptual drawing illustrating, in greater detail, the example IMD, leads, and sensor of FIG. 1 in conjunction with a heart.

In one example, IMD 15 comprises a leadless pressure sensor including capacitive pressure sensing elements configured to measure blood pressure within pulmonary artery 39. As illustrated in FIGS. 1 and 2, IMD 15 may be in wireless communication with IMD 16 or one or more sensors on leads 18, 20, or 22, e.g., in order to transmit blood pressure measurements to the IMD. IMD 15 may employ, e.g., radio frequency (RF) or other telemetry techniques for communicating with IMD 16 and other devices, including, e.g., programmer 24. In another example, IMD 15 may include a tissue conductance communication (TCC) system by which the device employs tissue of patient 14 as an electrical communication medium over which to send and receive information to and from IMD 16 and other devices.

In some examples, IMD 15 may be implanted within other body lumens, such as other vasculature of patient 14. Additionally or alternatively to including a pressure sensor, IMD 15 may also include sensors such as, but not limited to an electrocardiogram sensor, a fluid flow sensor, a tissue oxygen sensor, an accelerometer, a glucose sensor, a potassium sensor, a thermometer and/or other sensors. In some examples, system 10 may include a plurality of sensors 38, e.g., to provide sensing of one or more physiological conditions of patient 14 at a variety of locations.

Referring again to FIG. 1, system 10 may, in some examples, additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, physiological therapy/monitoring system 10 may include temporary or permanent epicardial or subcutaneous leads, instead of or in addition to leads 18, 20 and 22. Such leads may be used for one or more of cardiac sensing, pacing, or cardioversion/defibrillation. Moreover, it is conceivable that some sort of biodegradable fixation element could be used to hold IMD 15 to the epicardium, while a chronic fixation element fixes the IMD 15 permanently in that location. Once fixed permanently, the biodegradable fixation element would dissolve in a controlled fashion, leaving the IMD 15 permanently attached to the epicardium.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 detects fibrillation employing any of a number of known fibrillation detection techniques.

In some examples, IMD 16 may also be solely a monitoring device, attached to various sensors, or even a monitoring device that only communicates with one or more devices 38 in various locations of the heart, or other vasculature, or even other organs. Such a device could be used, for example, to provide an integrated physiologic monitoring system that monitors, e.g., heart failure and one or more of its comorbidities (e.g. diabetes, renal function, etc.). Further, IMD 16 could be a combined monitoring and therapy system with multiple sensor and or "remote" therapy devices, 38. For example, IMD 16 could control a devices, which may have similar outer housing dimensions, and may be implanted similarly to IMD 15, but which are configured to act as leadless pacemakers, in the right and left ventricles, (or on the left ventricular epicardium), as a means of providing cardiac resynchronization. IMD 16 could then also communicate with other sensors 38 in other vessels/organs, that serve primarily as sensors of flow, pressure, or other parameters, for the purpose of additional monitoring and control of heart failure. Heart failure is rapidly becoming viewed as a multi-system disease, which may affect the heart, lungs, kidneys, and pancreatic function.

Programmer 24 shown in FIG. 1 may be a handheld computing device, computer workstation, or networked computing device. Programmer 24 may include electronics and other internal components necessary or desirable for executing the functions associated with the device. In one example, programmer 24 includes one or more processors and memory, as well as a user interface, telemetry module, and power source. In general, memory of programmer 24 may include computer-readable instructions that, when executed by a processor of the programmer, cause it to perform various functions attributed to the device herein. Memory, processor(s), telemetry, and power sources of programmer 24 may include similar types of components and capabilities described above with reference to similar components of IMD 16. The programmer may also be a dedicated wireless system that communicates with IMD 16 remotely, say, from the patient's bedside table, while the patient sleeps.

In one example, programmer 24 includes a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. The user may also interact with programmer 24 remotely via a networked computing device. Or, the "programmer" may be a fully automated monitoring base station for use in the patient's home, with little or no capability for the user to provide input or programming of the implanted device. A physician could also log into the programmer 24 from a remote location via the internet, cell phone technology, or other satellite-based communication, and program the implanted device(s).

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, arrhythmic episodes, or sensor trends). As another example, the user may use programmer 24 to retrieve information from IMD 16 regarding other sensed physiological parameters of patient 14, such as intracardiac or intravascular pressure, activity, posture, respiration, or thoracic impedance. The sensed physiological parameters may be based on information received from IMD 15. As another example, the user may use programmer 24 to retrieve information from IMD 16 regarding the performance or integrity of IMD 16 or other components of system 10, such as leads 18, and 22, or a power source of IMD 16. In some examples, this information may be presented to the user as an alert.

The user may use programmer 24 to program a therapy progression, select electrodes used to deliver electrical stimulation to heart 12 (e.g., in the form of pacing pulses or cardioversion or defibrillation shocks), select waveforms for the electrical stimulation, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication, e.g. via telemetry modules in each of the devices using any number of known techniques. Examples of communication techniques may include, for example, low frequency or RF telemetry, but other techniques are also contemplated. In some examples, programmer 24 may include a programming head that may be placed proximate to the patient's body near the IMD 16 implant site in order to improve the quality or security of communication between IMD 16 and programmer 24. Other example medical systems need not have IMD 16 or provide therapy. For example, a medical system may only include IMD 15, which may communicate directly with an eternal device, e.g., programmer 24.

FIG. 2 is a conceptual diagram illustrating IMD 16 and leads 18, 20 and 22 of medical system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of setscrews, connection pins, snap connectors, or another suitable mechanical coupling mechanism. Leads 18, 20 22 include electrodes for delivery of stimulation and/or sensing and may additionally include one or more sensors as mentioned above with respect to FIG. 1.

Each of the leads 18, 20, 22 includes an elongated insulative lead body, which may carry a number of concentric coiled conductors separated from one another by tubular insulative sheaths. Other lead configurations may also be used. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other embodiments, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The sensed electrical signals may be processed as a cardiac electrogram (EGM) signal by IMD 16.

Any combination of electrodes 40, 42, 44, 46, 48, 50, 58, 62, 64 and 66 may be considered a sensing configuration that has one or more electrodes. In some examples, a sensing configuration may be a bipolar electrode combination on the same lead, such as electrodes 40 and 42 of lead 18. In any sensing configuration, the polarity of each electrode in the sensing configuration may be configured as appropriate for the application of the sensing configuration.

In some examples, IMD 16 delivers pacing pulses via bipolar combinations of electrodes 40, 42, 44, 46, 48 and 50 to cause depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver cardioversion or defibrillation pulses to heart 12 via any combination of elongated electrodes 62, 64, 66, and housing electrode 58. Electrodes 58, 62, 64, 66 may also be used to deliver cardioversion pulses, e.g., a responsive therapeutic shock, to heart 12. Electrodes 62, 64, 66 may be fabricated from any suitable electrically conductive material, such as, but not limited to, platinum, platinum alloy or other materials known to be usable in implantable defibrillation electrodes.

The configuration of medical system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26.

Figure 3:
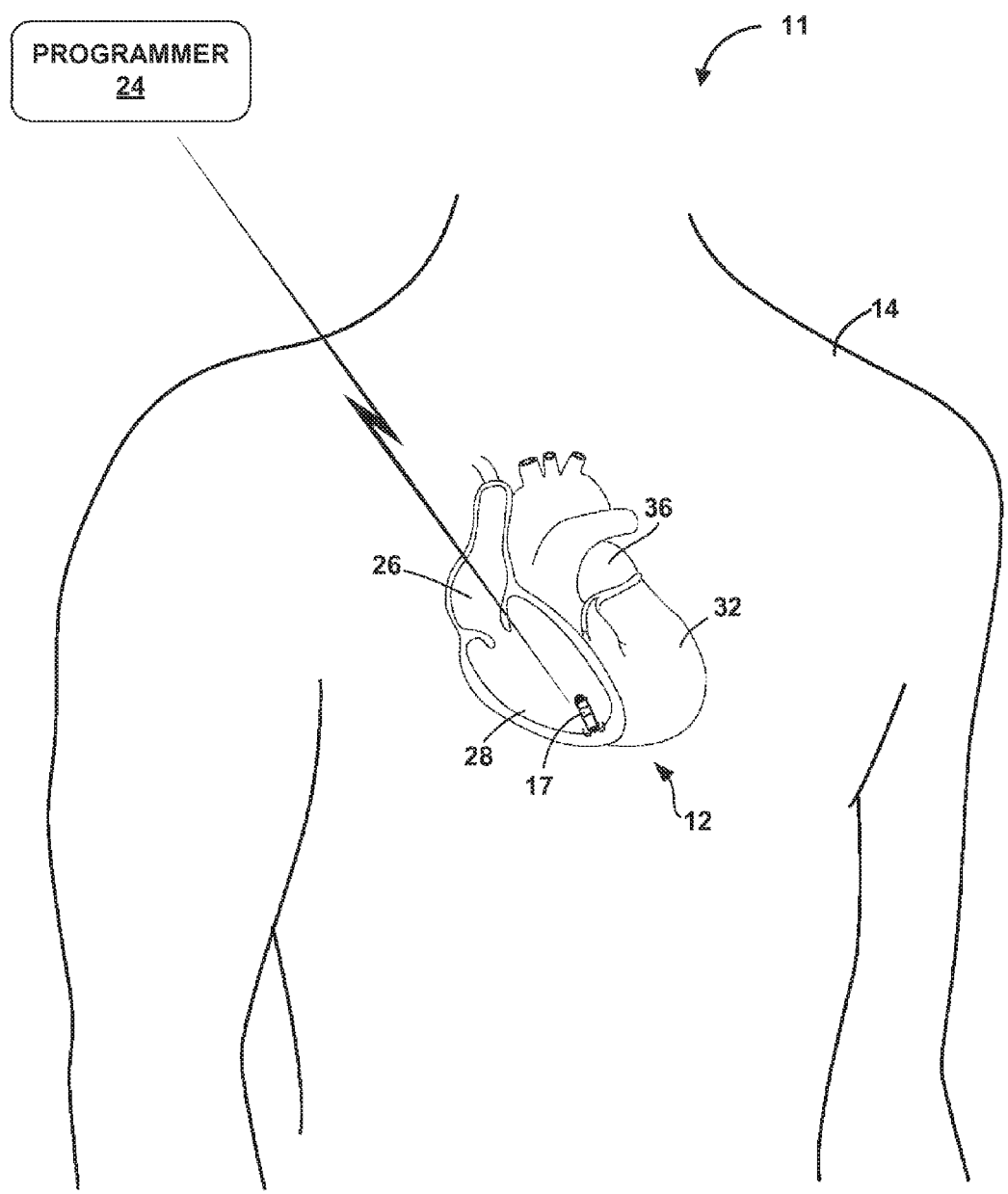
FIG. 3 is a conceptual diagram illustrating an example therapy system comprising a leadless IMD that may be used to monitor one or more physiological parameters of a patient and/or provide therapy to the heart of a patient.

FIG. 3 is a conceptual diagram illustrating an example medical system 11 that may be used to monitor one or more physiological parameters of patient 14 and/or to provide therapy to heart 12 of patient 14. Medical system 11 includes IMD 17, which is coupled to programmer 24. IMD 17 may be an implantable leadless pacemaker that provides electrical signals to heart 12 via one or more electrodes (not shown in FIG. 3) on its outer housing. Additionally or alternatively, IMD 17 may sense electrical signals attendant to the depolarization and repolarization of heart 12 via electrodes on its outer housing. In some examples, IMD 17 provides pacing pulses to heart 12 based on the electrical signals sensed within heart 12.

IMD 17 includes a set of active fixation tines to secure IMD 17 to a patient tissue. In other examples, IMD 17 may be secured with other techniques such as a helical screw or with an expandable fixation element. In the example of FIG. 3, IMD 17 is positioned wholly within heart 12 proximate to an inner wall of right ventricle 28 to provide right ventricular (RV) pacing. Although IMD 17 is shown within heart 12 and proximate to an inner wall of right ventricle 28 in the example of FIG. 3, IMD 17 may be positioned at any other location outside or within heart 12. For example, IMD 17 may be positioned outside or within right atrium 26, left atrium 36, and/or left ventricle 32, e.g., to provide right atrial, left atrial, and left ventricular pacing, respectively.

Depending on the location of implant, IMD 17 may include other stimulation functionalities. For example, IMD 17 may provide atrioventricular nodal stimulation, fat pad stimulation, vagal stimulation, or other types of neurostimulation. In other examples, IMD 17 may be a monitor that senses one or more parameters of heart 12 and may not provide any stimulation functionality. In some examples, medical system 11 may include a plurality of leadless IMDs 17, e.g., to provide stimulation and/or sensing at a variety of locations.

As mentioned above, IMD 17 includes a set of active fixation tines. The active fixation tines in the set are deployable from a spring-loaded position in which distal ends of the active fixation tines point away from the IMD to a hooked position in which the active fixation tines bend back towards the IMD. The active fixation tines allow IMD 17 to be removed from a patient tissue followed by redeployment, e.g., to adjust the position of IMD 17 relative to the patient tissue. For example, a clinician implanting IMD 17 may reposition IMD 17 during an implantation procedure if the original deployment of the active fixation tines provides an insufficient holding force to reliably secure IMD 17 to the patient tissue. As another example, the clinician may reposition IMD 17 during an implantation procedure if testing of IMD 17 indicates an unacceptably high capture threshold, which may be caused by, e.g., the specific location of IMD 17 or a poor electrode-tissue connection.

FIG. 3 further depicts programmer 24 in wireless communication with IMD 17. In some examples, programmer 24 comprises a handheld computing device, computer workstation, or networked computing device. Programmer 24 includes a user interface that presents information to and receives input from a user. The user may also interact with programmer 24 remotely via a networked computing device.

A user, such as a physician, technician, surgeon, electrophysiologist, other clinician, or patient, interacts with programmer 24 to communicate with IMD 17. For example, the user may interact with programmer 24 to retrieve physiological or diagnostic information from IMD 17. A user may also interact with programmer 24 to program IMD 17, e.g., select values for operational parameters of the IMD 17. For example, the user may use programmer 24 to retrieve information from IMD 17 regarding the rhythm of heart 12, trends therein over time, or arrhythmic episodes.

As an example, the user may use programmer 24 to retrieve information from IMD 17 regarding other sensed physiological parameters of patient 14 or information derived from sensed physiological parameters, such as intracardiac or intravascular pressure, intracardiac or intravascular fluid flow, activity, posture, tissue oxygen levels, respiration, tissue perfusion, heart sounds, cardiac electrogram (EGM), intracardiac impedance, or thoracic impedance. In some examples, the user may use programmer 24 to retrieve information from IMD 17 regarding the performance or integrity of IMD 17 or other components of system 17, or a power source of IMD 17. As another example, the user may interact with programmer 24 to program, e.g., select parameters for, therapies provided by IMD 17, such as pacing and, optionally, neurostimulation.

IMD 17 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 17 implant site in order to improve the quality or security of communication between IMD 17 and programmer 24.

Figure 4:
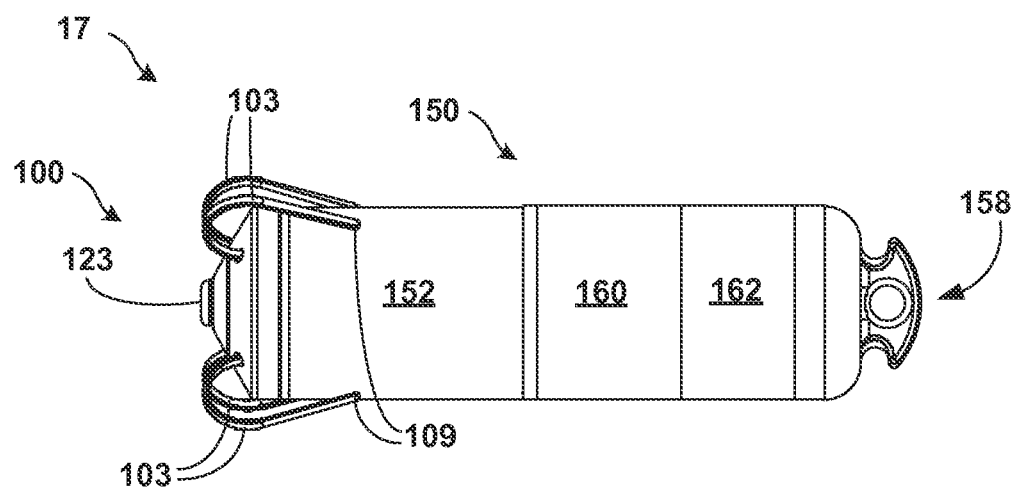
FIG. 4 illustrates the leadless IMD of FIG. 3 in further detail.

FIG. 4 illustrates leadless IMD 17 of FIG. 3 in further detail. In the example of FIG. 4, leadless IMD 17 includes tine fixation subassembly 100 and electronic subassembly 150. Tine fixation subassembly 100 includes active fixation tines 103 and is configured to deploy anchor leadless IMD 17 to a patient tissue, such as a wall of heart 12.

Electronic subassembly 150 includes electrode 123, control electronics 152, which controls the sensing and/or therapy functions of IMD 17, and battery 160, which powers control electronics 152. As one example, control electronics 152 may include sensing circuitry, a stimulation generator and a telemetry module. As one example, battery 160 may comprise features of the batteries disclosed in U.S. patent application Ser. No. 12/696,890, titled IMPLANTABLE MEDICAL DEVICE BATTERY and filed Jan. 29, 2010, the entire contents of which are incorporated by reference herein.

The housings of control electronics 152 and battery 160 are formed from a biocompatible material, such as a stainless steel or titanium alloy. In some examples, the housings of control electronics 152 and battery 160 may include a parylene coating. Electronic subassembly 150 further includes anode 162, which may include a titanium nitride coating. The entirety of the housings of control electronics 152 and battery 160 are electrically connected to one another, but only anode 162 is uninsulated. Alternatively, anode 162 may be electrically isolated from the other portions of the housings of control electronics 152 and battery 160. In other examples, the entirety of the housing of battery 160 or the entirety of the housing of electronic subassembly 150 may function as an anode instead of providing a localized anode such as anode 162.

Delivery tool interface 158 is located at the proximal end of electronic subassembly 150. Delivery tool interface 158 is configured to connect to a delivery device, such as a catheter used to position IMD 17 during an implantation procedure. For example, delivery tool interface 158 represents a looped element of IMD 17 and may be engaged by a catheter during delivery as discussed herein with respect to a variety of different examples.

Active fixation tines 103 are deployable from a spring-loaded position in which distal ends 109 of active fixation tines 103 point away from electronic subassembly 150 to a hooked position in which active fixation tines 103 bend back towards electronic subassembly 150. For example, active fixation tines 103 are shown in a hooked position in FIG. 4. Active fixation tines 103 may be fabricated of a shape memory material, which allows active fixation tines 103 to bend elastically from the hooked position to the spring-loaded position. As an example, the shape memory material may be shape memory alloy such as Nitinol.

In some examples, all or a portion of tine fixation subassembly 100, such as active fixation tines 103, may include one or more coatings. For example, tine fixation subassembly 100 may include a radiopaque coating to provide visibility during fluoroscopy. In one such example, active fixation tines 103 may include one or more radiopaque markers. As another example, active fixation tines 103 may be coated with a tissue growth promoter or a tissue growth inhibitor. A tissue growth promoter may be useful to increase the holding force of active fixation tines 103, whereas a tissue growth inhibitor may be useful to facilitate removal of IMD 17 during an explantation procedure, which may occur many years after the implantation of IMD 17.

As one example, IMD 17 and active fixation tines 103 may comprise features of the active fixation tines disclosed in U.S. Provisional Pat. App. No. 61/428,067, titled, "IMPLANTABLE MEDICAL DEVICE FIXATION" and filed Dec. 29, 2010, the entire contents of which are incorporated by reference herein.

FIG. 5 illustrates leadless IMD 15, which includes sensor element 38 and expandable fixation element 41. Expandable fixation element 41 is configured for securing leadless IMD 15 within a vasculature.

Expandable fixation element 41 is configured such that the outer diameter of expandable fixation element 41 is expandable to provide an interference fit with the inner diameter of pulmonary artery 39, or other body lumen. In some examples, expandable fixation element 41 may be partially deployable. As an example, the distal end of expandable fixation element 41 may be deployed from a catheter and expanded to provide an interference fit with the body lumen while the proximal end of expandable fixation element 41 may remain in a collapsed position within the distal end of the catheter.

Expandable fixation element 41 allows IMD 15 to be retracted before fully deploying IMD 15, e.g., to adjust the position of IMD 15 with a vasculature to a location in the vasculature providing a tighter (or looser) interference fit. For example, a clinician implanting IMD 15 may reposition IMD 15 during an implantation procedure if partial deployment of expandable fixation element 41 provides an insufficient holding force indicating that full deployment of expandable fixation element 41 may not reliably secure IMD 15 within the vasculature. As another example, a clinician may select an expandable fixation element with a size better suited for the vasculature than expandable fixation element 41 that provided an insufficient holding force.

Sensor element 38 includes control electronics that control the sensing and/or therapy functions of IMD 15 and a battery that powers the control electronics. As one example, the control electronics may include sensing circuitry and a telemetry module. Moreover, the battery may comprise features of the batteries disclosed in U.S. patent application Ser. No. 12/696,890, titled IMPLANTABLE MEDICAL DEVICE BATTERY and filed Jan. 29, 2010, the contents of which were previously incorporated by reference herein. The housing of sensor element 38 may be formed from a biocompatible material, such as stainless steel and/or titanium alloys.

Expandable fixation element 41 may be fabricated of a shape memory material that allows expandable fixation element 41 to bend elastically from the collapsed position to the expanded position. As an example, the shape memory material may be shape memory alloy such as Nitinol. As an example, expandable fixation element 41 may store less potential energy in the expanded position and thus be naturally biased to assume the expanded position when in the collapsed position. In this manner, expandable fixation element 41 may assume an expanded position when no longer constrained by a catheter or other delivery device.

In some examples, expandable fixation element 41 may resemble a stent. Techniques for a partially deployable stents that may be applied to expandable fixation element 41 are disclosed in U.S. Pat. Pub. No. 2007/0043424, titled, "RECAPTURABLE STENT WITH MINIMUM CROSSING PROFILE" and dated Feb. 22, 2007, the entire contents of which are incorporated by reference herein, as well as U.S. Pat. Pub. No. 2009/0192585, titled, "DELIVERY SYSTEMS AND METHODS OF IMPLANTATION FOR PROSTETIC HEART VALVES" and dated Jul. 30, 2009, the entire contents of which are also incorporated by reference herein.

In some examples, all or a portion of expandable fixation element 41, may include one or more coatings. For example, expandable fixation element 41 may include a radiopaque coating to provide visibility during fluoroscopy. As another example, expandable fixation element 41 may be coated with a tissue growth promoter or a tissue growth inhibitor.

Figure 6:
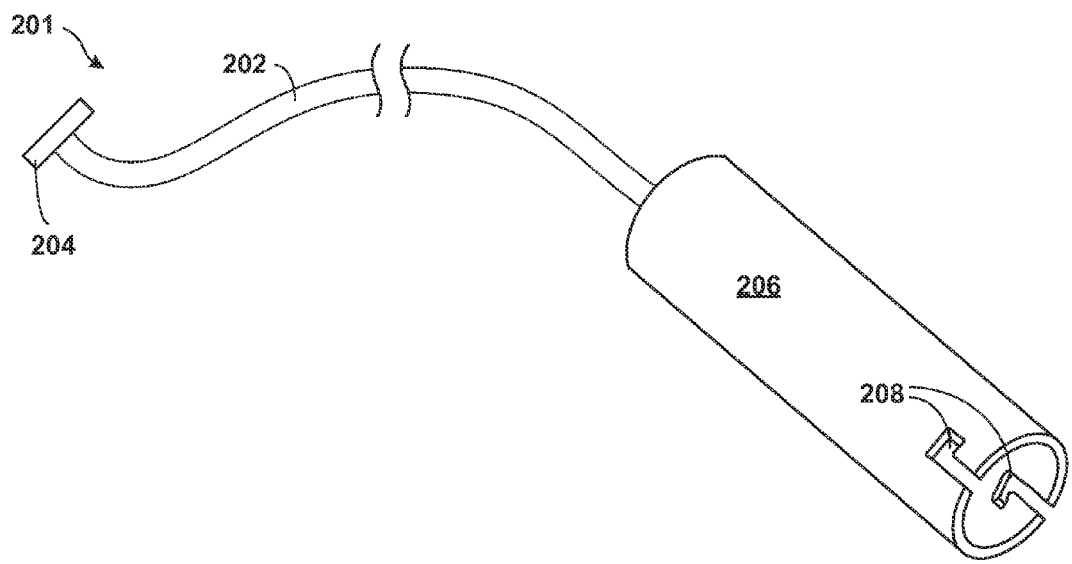
FIGS. 6-8E illustrate an example system for intravascular delivery of an IMD during an implantation procedure.
Figure 7:
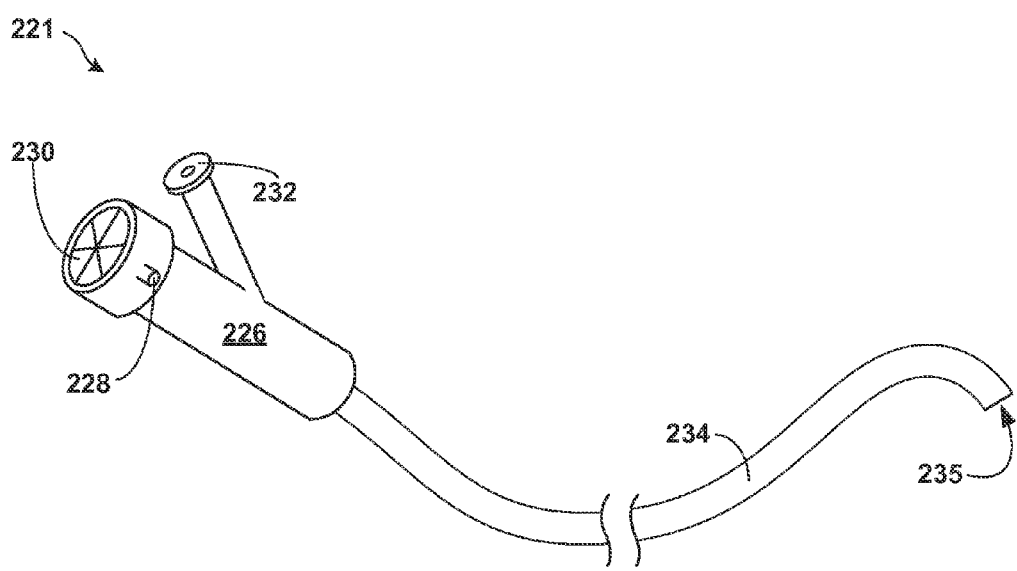

FIGS. 6-8E illustrate a system for intravascular delivery of an IMD during an implantation procedure. As referred to herein, intravascular IMD delivery not only includes delivering IMD through a vasculature to a target site within a vasculature, but also includes delivering IMD through a vasculature to other target sites such as target sites within the heart and other transvascular IMD deliveries. The kit of the IMD delivery system includes assembly 201 and assembly 221, shown in FIGS. 6 and 7 respectively. As shown in FIG. 6, assembly 201 includes elongated inner sheath 202 and coupling module 206, which is slidably connected to inner sheath 202. As shown in FIG. 7, assembly 221 includes elongated outer sheath 234 and coupling module 226.

Outer sheath 234 of assembly 221 forms an inner lumen 227 (FIG. 8A) with proximal opening 233 (FIG. 8A) and distal opening 235 (FIG. 7). Outer sheath 234 is sized to traverse a vasculature of a patient during a surgical procedure to facilitate positioning distal opening 235 proximate a target site within the patient. In different examples, outer sheath 234 may be steerable or be configured to traverse a guidewire to be directed to the target site from the access point of the vasculature. In any event, outer sheath 234 includes sufficient longitudinal stiffness to facilitate manipulation from its proximal end, but also include sufficient radial flexibility to facilitate following the patient's vasculature from an access point, such as a femoral artery, to a position proximate the target site within the patient.

In one example, outer sheath 234 may have an inner diameter of about 0.15 inch and an outer diameter of about 0.18 inch. It may be extruded from polyether block amide copolymer (PEBA) having 55 shore D durometer or, alternatively, may be formed as a reinforced tube having an inner polytetrafluoroethylene (PTFE) liner, an intermediate reinforcing layer of braided stainless steel and an outer jacket of 55D durometer PEBA. In other examples, other flexible polymers may be used such as nylons and polyethylenes. The distal end of outer sheath 234 preferably includes a radiopaque ring that may be formed by incorporating barium sulfate or other suitable radiopaque material such as tungsten into or at the end of outer sheath 234.

During an implantation procedure, the distal end of outer sheath 234 is positioned proximate a target site for implantation of the IMD. Inner lumen 227 is configured to receive the distal end of inner sheath 202, as well as IMD 214, and inner sheath 202 is used to push the IMD through the entirety outer sheath 234 to the target site. In this manner, an IMD is passed through the entirety of the inner lumen 227 before exiting distal opening 235 of outer sheath 234 during the implantation procedure.

In assembly 221, coupling module 226 is secured to the proximal end of outer sheath 234. Coupling module 226 includes valve 230, which is configured to prevent bodily fluids from passing through inner lumen 227 and leaking out of proximal opening 233. Coupling module 226 further includes Luer fitting 232 that facilitates flushing outer sheath 234.

Coupling module 226 is configured to connect to coupling module 206 of assembly 201 such that inner sheath 202 is axially aligned with outer sheath 234. For example, coupling modules 206, 226 include quick connect features for mating coupling module 226 with coupling module 206 such that inner sheath 202 is in coaxial alignment with outer sheath 234. In the example, shown in FIG. 6, the quick connect features of coupling module 206 are grooves 208, which are configured to receive protrusions 228 of coupling module 226 in a rotating snap-fit configuration. It should be noted, however, that the particular techniques used for mating coupling module 206 with coupling module 226 are not germane to this disclosure, and any suitable connecting features, such as snap-fit or threaded features may be used in other examples.

As previously mentioned, elongated inner sheath 202 is slidably connected to inner sheath 202 as part of assembly 201. This allows inner sheath 202 to enter proximal opening 233 of inner lumen 227 of outer sheath 234 once coupling module 206 is mated to coupling module 226 such that inner sheath 202 is in coaxial alignment with outer sheath 234. In one example, outer sheath 234 may have an inner diameter of about 0.15 inches and the distal end of inner sheath may have an outer diameter of about 0.12-0.14 inches at its distal end. In some examples, inner sheath 202 may have a smaller profile along its length than at its distal end, e.g., a tighter fitting distal cap to enable a good pushing surface with lower proximal friction due to the smaller profile along the length of inner sheath 202. In addition or alternately, inner sheath 202 may be shaped with a lower contact friction design such as a triangular to star like profile to minimize drag friction with outer sheath 234. In different examples, inner sheath may have a solid profile, a hollow tubular profile or a combination thereof.

In some examples, inner sheath may be formed from 70D durometer PEBA. In other examples, other flexible polymers may be used such as nylons and polyethylenes.

Inner sheath 202 includes finger grip 204, which allow a clinician to slidably move sheath 202 relative to coupling module 206 and outer sheath 234 during an implantation procedure. In some examples, inner lumen 227 of outer sheath 234 and/or the outer surface of inner sheath 202 may include a friction-reducing coating to reduce the force required to move inner sheath within inner lumen 227 of outer sheath 234. Coupling module 206 further includes seal 210 (FIGS. 8A-8C), which creates a seal between coupling module 206 and inner sheath 202 while allowing inner sheath 202 to slide in a longitudinal direction.

FIGS. 8A-8E illustrate techniques for intravascular implantation of IMD 214 using a kit including assemblies 201, 221. FIGS. 8A-8E illustrate assemblies 201, 221 as well as IMD 214. IMD 214 includes expandable fixation element 215, which is deployable from a collapsed position to an expanded position secure the IMD 214 proximate a target site within a patient.

While FIGS. 8A-8E illustrate implantation techniques using IMD 214, in different examples, IMD 214 may be substantially similar to IMD 17 (FIG. 4) or IMD 15 (FIG. 5). As one example, the intravascular IMD delivery system of FIGS. 6-8E may be used to deliver IMD 17 to a position within a heart of a patient, such as a position proximate to an inner wall of the right ventricle, within the right atrium, the left atrium, and/or left ventricle. As another example, the intravascular IMD delivery system of FIGS. 6-8E may be used to deliver IMD 15 to an intravascular position such as a pulmonary artery or other vasculature of the patient.

As shown in FIGS. 8A-8E, coupling module 206 of assembly 201 is configured to mate to coupling module 226 of assembly 221 to facilitate intravascular implantation of IMD 214 within a patient. During an implantation procedure, the clinician would position the distal end of outer sheath 234 proximate to a target site within the patient via a vasculature accessed during a surgical procedure. For example, outer sheath 234 may be advanced into an entry vessel, such as the femoral artery, and then manipulated and navigated through the patient's vasculature until the distal end of outer sheath 234 proximate to a target site within the patient. The clinician may use imaging techniques, such as fluoroscopy, to monitor the position of outer sheath 234, inner sheath 202, and IMD 214 throughout the implantation procedure. Assemblies 201, 221 and/or IMD 214 may include radiopaque portions or markers to facilitate visualization.

Once the distal end of outer sheath 234 is proximate to a target site within the patient, as shown in FIG. 8A, a clinician positions assembly 201 adjacent to assembly 221 such that coupling module 206 faces coupling module 221. Then, as shown in FIG. 8B, coupling module 206 is mated to coupling module 226 such that inner sheath 202 is in coaxial alignment with outer sheath 234.

Coupling module 206 forms inner lumen 207, which is configured to hold IMD 214 when coupling module 206 is not connected coupling module 226. When coupling module 206 is mated to coupling module 226, coupling module 206 presses open the leaflets of valve 230 such that inner lumen 207 of coupling module 206 opens to inner lumen 227 of outer sheath 234.

In this manner, valve 230 is configured to open to allow inner sheath 202 to enter inner lumen 227 of outer sheath 234. In addition, coupling module 206 forms a seal with coupling module 226 when coupling module 206 is connected to coupling module 226. Even though valve 230 is open when coupling module 206 is connected to coupling module 226, the seal between coupling module 206 and coupling module 226 and seal 210 between inner sheath 202 coupling module 206 combine to prevent bodily fluids from continuously exiting the patient through inner lumen 227 of outer sheath 234.

Figure 8C:
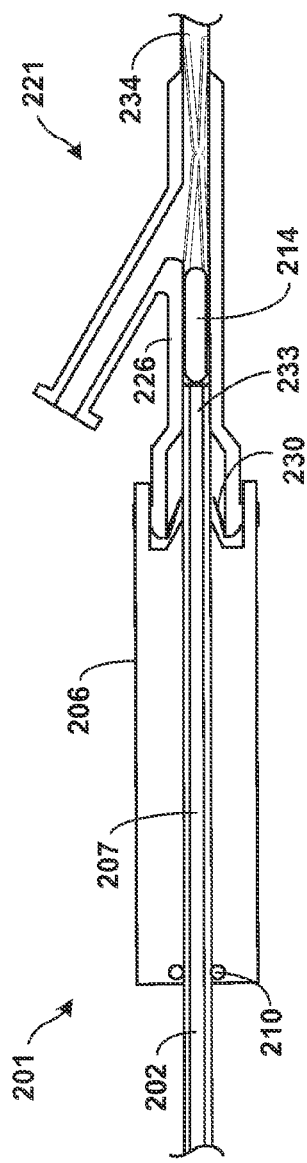

As shown in FIG. 8C, a clinician uses inner sheath 202 to push IMD 214 into proximal opening 233 of inner lumen 227 of outer sheath 234. For example, IMD 214 may be preloaded within inner lumen 207 of coupling module 206 in assembly 201 before coupling module 206 is mated to coupling module 226. In the example in which IMD 214 includes a pressure sensor, such as a pressure transducer, preloading IMD 214 within inner lumen 207 by the manufacturer may serve to protect the transducer from damage, such as damage caused by handling. By pushing on finger grip 204 (FIG. 6), the clinician may slide inner sheath 202 in a longitudinal direction to push IMD 214 out of inner lumen 207 of coupling module 206 and into inner lumen 227 of outer sheath 234.

Figure 8D:
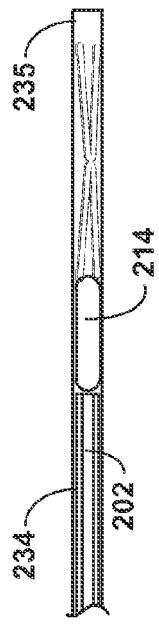
Figure 8E:
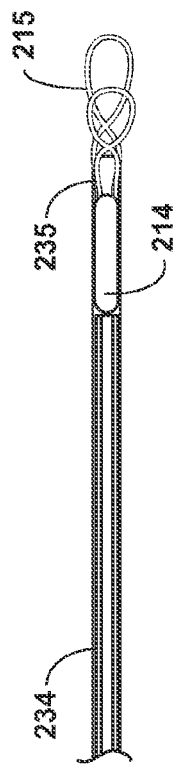

As shown in FIG. 8D, the clinician may continue push IMD 214 through inner lumen 227 of outer sheath 234 advancing IMD 214 through the patient's vasculature as navigated by outer sheath 234. FIG. 8D illustrates inner sheath 202 pushing IMD 214 up to distal opening 235 of outer sheath 234. FIG. 8E illustrates inner sheath 202 pushing IMD 214 through distal opening 235 of outer sheath 234. As shown in FIG. 8E, expandable fixation element 215 of IMD 214 is expanded from a collapsed position to an expanded position as IMD 214 through distal opening 235. In the expanded position, expandable fixation element 215 will secure IMD 214 within the patient, e.g., as described with respect to IMD 17 (FIG. 4) or IMD 15 (FIG. 5).

The IMD delivery system of FIGS. 6-8E may provide one or more advantages. As one example, intravascular delivery of larger implants may often necessitate large bore delivery sheaths to be tracked through complex anatomy, which can require a clinician to use a variety of specialized tools. As compared to an intravascular delivery system in which an IMD is delivered to a target site simultaneously with the delivery system, e.g., the IMD is contained in the distal end of the delivery system as the delivery system is routed to the target site, the IMD delivery system of FIGS. 6-8E may simplify routing of the delivery system to the target site. For example, with the IMD delivery system of FIGS. 6-8E, the clinician first routes outer sheath 234 to the target site. As clinicians often have experience routing intravascular sheaths, the process and instruments used to route outer sheath 234 may be familiar to the clinician. Furthermore, with the IMD delivery system of FIGS. 6-8E, only after first routing outer sheath 234 to the target site, does the clinician then introduce the IMD. This may reduce the chance for damage to the IMD as compared to a delivery system in which the IMD is transported proximate to the target site within the distal portion of the delivery system.

FIGS. 9A-9D illustrate example techniques for intravascular delivery of a sheath. As one example, the techniques illustrated in FIGS. 9A-9D may be used for intravascular delivery of outer sheath 234. In such an example, outer sheath 320 of FIGS. 9A-9D may be considered to be substantially similar to outer sheath 234. For example, outer sheath 320 may be included in an assembly with coupling module 206, and outer sheath 320 may be used to deliver an IMD as described with respect to FIGS. 8A-8E. However, the techniques illustrated in FIGS. 9A-9D are not the only manner in which outer sheath 234 may be delivered within a patient and any technique known to those in the art for intravascular delivery of a sheath may be used to position outer sheath 234.

Figure 9A:
FIGS. 9A-9D illustrate example techniques for intravascular delivery of a sheath.

As represented by FIG. 9A, guidewire 310 is first routed from an access point through a vasculature of the patient until distal end 312 of guidewire 310 is positioned proximate to a target site within the patient. In different examples, the target site may be within a pulmonary artery of the patient, within another vasculature of the patient, or a position within a heart of a patient, such as a position proximate to an inner wall of the right ventricle, right atrium, left atrium, and/or left ventricle. Guidewire 310 may be routed using any techniques known to those in the art. For example, clinician may use imaging techniques, such as fluoroscopy, to monitor the position of guidewire 310.

Figure 9B:
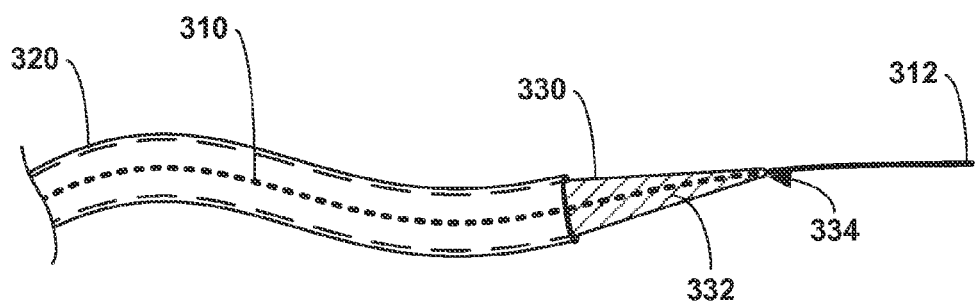
Figure 9C:
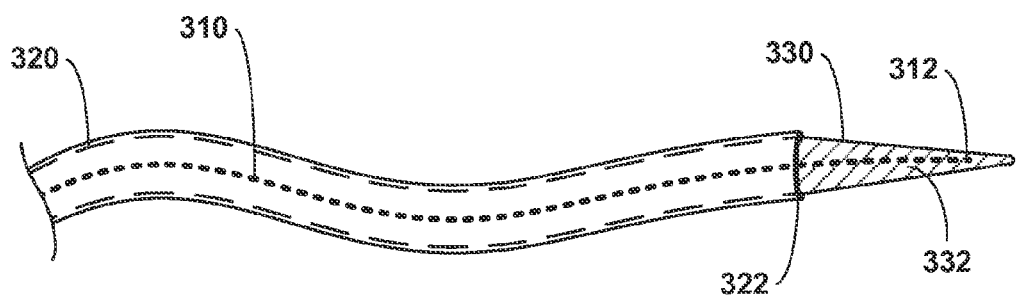

As represented by FIG. 9B, after distal end 312 of guidewire 310 is positioned proximate to a target site within the patient, the clinician routes an assembly including outer sheath 320 and inner sheath 330 over the proximal end guidewire 310 and pushes the assembly along guidewire 310 until distal opening 322 of outer sheath 320 is proximate the target site within the patient.

Elongated outer sheath 320 is sized to traverse the vasculature of the patient. Outer sheath 320 forms inner lumen 324, which has distal opening 322. In some examples, inner lumen 324 may extend the length of outer sheath 320 and also provide a proximal opening.

Elongated inner sheath 330 includes tapered distal end 332. In one example, tapered distal end 332 may have a conical shape. Tapered distal end 332 is configured to substantially fill inner lumen 324 of outer sheath 320 to close-off distal opening 322 of outer sheath 320. Inner sheath 330 includes guidewire lumen 334, which may extend throughout the length of inner sheath 330. The diameter of guidewire lumen 334 at distal tip 332 corresponds to the diameter of guidewire 310. In some examples, guidewire lumen 334 may be greater at other portions of inner sheath 330 than at distal tip 332, and such a configuration may limit friction between guidewire 310 and inner sheath 330. In other examples, guidewire lumen 334 may have a consistent diameter throughout the length of inner sheath 330. In one example, distal tip 332 may be formed from 35D durometer PEBA or a blend of 40D durometer PEBA and barium sulfate, bismuth compounds (trioxide, oxychloride), tungsten and/or polymer fillers. In other examples, other flexible polymers may be used such as nylons and polyethylenes. In any case, these and other polymer fillers may be selected to provide desirable material properties, such as stiffness, flexibility, reduce friction and/or increase radiopacity.

In the assembly of outer sheath 320 and inner sheath 330, tapered distal end 332 extends beyond distal opening 322 of outer sheath 320; however, inner sheath 330 may be advanced and retracted relative to outer sheath 320 by the clinician during the implantation procedure, if desired, as inner sheath 330 is slidable within inner lumen 324 of outer sheath 320.

Figure 9D:
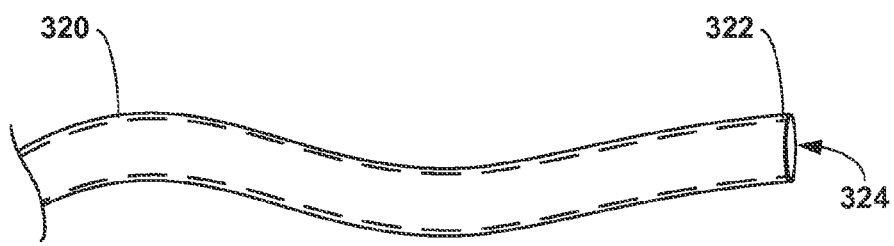

After the assembly of outer sheath 320 and inner sheath 330 is advanced along guidewire 310 until distal opening 322 of outer sheath 320 is proximate the target site within the patient (FIG. 9C), guidewire 310 and inner sheath 330 are withdrawn from outer sheath 320 (FIG. 9D). For example, a clinician may simply pull on guidewire 310 and inner sheath 330 from a proximal end of outer sheath 320 to slide guidewire 310 and inner sheath 330 out of the proximal opening of outer sheath 320. In another example, a clinician may remove inner sheath 330 and leave the guidewire 312 in place to enable the tracking of ancillary devices.

FIGS. 10A-10D illustrate example techniques for intravascular delivery of IMD 380 through outer sheath 320 using deployment receptacle 340. Specifically, FIGS. 10A-10D illustrate distal portions of outer sheath 320 and elongated deployment receptacle 340. As previously mentioned, outer sheath 320 may be considered to be substantially similar to outer sheath 234. For example, outer sheath 320 may be included in an assembly with coupling module 206. In such an example, deployment receptacle 340 may be slidably coupled to coupling module 226 in a mating assembly, and the distal end of deployment receptacle 340 may be positioned proximate a target site within a patient in a similar manner that inner sheath 202 is positioned proximate a target site within a patient as described with respect to FIGS. 8A-8E.

Deployment receptacle 340 includes deployment bay 342 at a distal end of deployment receptacle 340. Deployment bay 342 is configured to carry IMD 380 through inner lumen 324 of outer sheath 320. Deployment receptacle 340 is slidable within inner lumen 324 of outer sheath 320 when inner lumen 324 is open, e.g., when inner sheath 330 is not within inner lumen 324 of outer sheath 320.

IMD 380 includes expandable fixation element 381, which is deployable from a collapsed position to an expanded position secure the IMD 380 proximate a target site within a patient. While FIGS. 10A-10D illustrate implantation techniques using IMD 380, in different examples, IMD 380 may be substantially similar to IMD 17 (FIG. 4) or IMD 15 (FIG. 5). As one example, the techniques of FIGS. 10A-10D may be used to deliver IMD 17 to a position within a heart of a patient, such as a position proximate to an inner wall of the right ventricle, within the right atrium, the left atrium, and/or left ventricle. As another example, the techniques of FIGS. 10A-10D may be used to deliver IMD 15 to an intravascular position such as a pulmonary artery or other vasculature of the patient.

Deployment receptacle 340 facilitates deployment of IMD 380 out of distal opening 322 of outer sheath 320. In particular, deployment receptacle 340 includes tether 350, which has helical element 352 on its distal end. Tether 350 is remotely controllable from a proximal end of deployment receptacle 340 to release IMD 380 from deployment bay 342. Tether 350 is stiff enough to facilitate pushing IMD 380 out of deployment bay 342 as well as pushing IMD 380 into deployment bay 342.

Specifically, a clinician, from the proximal end of deployment receptacle 340, may remotely push tether 350 distally relative to deployment bay 342 to push IMD 380 out distal opening 343 of deployment bay 342. This maintains the position of IMD 380 within the patient during deployment, which facilitates precise positioning of IMD 380. In one example, clinician actually retracts outer sheath 320 proximally to push tether 350 distally relative to deployment bay 342 to push IMD 380 out distal opening 343 of deployment bay 342. Then the clinician may, again from the proximal end of deployment receptacle 340, remotely rotate tether 350 such that helical element 352 releases a looped element of IMD 380 to deploy IMD 380. Specifically, in the example illustrated in FIG. 10C, as expandable fixation element 381 is the looped element of IMD 380, and rotating helical element 352 releases expandable fixation element 381 from deployment receptacle 340.

During an implantation procedure, the clinician would position the distal end of outer sheath 320 proximate to a target site within the patient via a vasculature accessed during a surgical procedure. For example, outer sheath 320 may be advanced into an entry vessel, such as the femoral artery, and then manipulated and navigated through the patient's vasculature until the distal end of outer sheath 320 proximate to a target site within the patient. The clinician may use imaging techniques, such as fluoroscopy, to monitor the position of outer sheath 320, deployment receptacle 340, and IMD 380 throughout the implantation procedure. In some examples, may be outer sheath 320 routed to the target site using the techniques described with respect to FIGS. 9A-9D; however, any technique known to those in the art for intravascular delivery of a sheath may be position outer sheath 234 such that the distal end of outer sheath 320 is proximate the target site within the patient.

Once the distal end of outer sheath 320 proximate to a target site within the patient, as represented by FIG. 10A, a clinician delivers IMD 380 to the target site by pushing deployment receptacle 340 through inner lumen 324 of outer sheath 320. In one example, the clinician may align distal opening 343 of deployment receptacle 340 with the proximal opening of inner lumen 324 of outer sheath 320. As an example, IMD 380 may be preloaded within deployment bay 342 before deployment receptacle 340 is inserted into outer sheath 320. In the example in which IMD 380 includes a pressure sensor, such as a pressure transducer, preloading IMD 380 within deployment bay 342 by the manufacturer may serve to protect the transducer from damage, such as damage caused by handling. The clinician continues to push deployment receptacle 340 through inner lumen 324 of outer sheath 320 at least until distal opening 343 of deployment receptacle 340 reaches distal opening 322 of outer sheath 320.

As represented by FIG. 10B, once deployment bay 342 is positioned proximate the target site, the clinician deploys IMD 380 from deployment receptacle 340. Specifically, a clinician, from the proximal end of deployment receptacle 340, may remotely push tether 350 distally relative to deployment bay 342 to push IMD 380 out distal opening 343 of deployment bay 342. As shown in FIG. 10B, a portion of expandable fixation element 381 of IMD 380 is expanded from a collapsed position to an expanded position as IMD 380 passes out of distal opening 343 of deployment bay 342. In the expanded position, expandable fixation element 381 will secure IMD 380 within the patient, e.g., as described with respect to IMD 17 (FIG. 4) or IMD 15 (FIG. 5).

As represented by FIG. 10C, once IMD 380 is fully removed from deployment bay 342, expandable fixation element 381 of IMD 380 is expanded assumes the expanded position. In order to fully deploy IMD 380 from deployment receptacle 340, the clinician remotely rotates tether 350 such that helical element 352 releases expandable fixation element 381, as represented by FIG. 10D. At this point, IMD 380 is fully deployed proximate to the target site, e.g., within a vasculature of the patient. IMD 380 is engaged to the vasculature of the patient because the expandable fixation element 381 elastically compressed within deployment receptacle 340 and expands to engage vasculature of the patient once released from deployment receptacle 340.

The clinician may optionally recapture IMD 380 by first grabbing a looped element of IMD 380, e.g., expandable fixation element 381, with helical element 352, and then using tether 350 to pull IMD 380 into deployment bay 342. In one example, tether 350 is held in a fixed location while outer sheath 320 is advanced distally to pull IMD 380 into deployment bay 342. In this manner, deployment receptacle 340 may be used to adjust the position of IMD 380 after full deployment, or to remove IMD 380 from the patient after full deployment. As one example, the clinician may decide to remove IMD 380 from the patient after full deployment if electronic testing of IMD 380 produces unsatisfactory results. As another example, the clinician may decide to remove IMD 380 from the patient after full deployment if the clinician determines that expandable fixation element 381 is improperly sized to locate IMD 380 at the target site. In such an example, IMD 380 may be replaced with an IMD including an expandable fixation element with a proper size. As another example, a clinician may use deployment receptacle 340 to remove IMD 380 during a subsequent surgical procedure, e.g., once IMD 380 has met or exceeded its projected lifespan. During such a subsequent surgical procedure, IMD 380 could be replaced with a new IMD using the same outer sheath used during the removal of IMD 380.

FIGS. 11A-11D illustrate example techniques for intravascular delivery of sheath 420 using inner sheath 430, which includes a distal portion with inflatable member 432. As one example, the techniques illustrated in FIGS. 11A-11D may be used for intravascular delivery of outer sheath 234. In such an example, outer sheath 420 of FIGS. 11A-11D may be considered to be substantially similar to outer sheath 234. For example, outer sheath 420 may be included in an assembly with coupling module 206, and outer sheath 420 may be used to deliver an IMD as described with respect to FIGS. 8A-8E.

Figure 11A:
FIGS. 11A-11D illustrate example techniques for intravascular delivery of an outer sheath using an inner sheath with a distal inflatable member.

As represented by FIG. 11A, guidewire 410 is first routed from an access point through a vasculature of the patient until distal end 412 of guidewire 410 is positioned proximate to a target site within the patient. In different examples, the target site may be within a pulmonary artery of the patient, within another vasculature of the patient, or a position within a heart of a patient, such as a position proximate to an inner wall of the right ventricle, right atrium, left atrium, and/or left ventricle. Guidewire 410 may be routed using any techniques known to those in the art. For example, clinician may use imaging techniques, such as fluoroscopy, to monitor the position of guidewire 410.

Figure 11B:
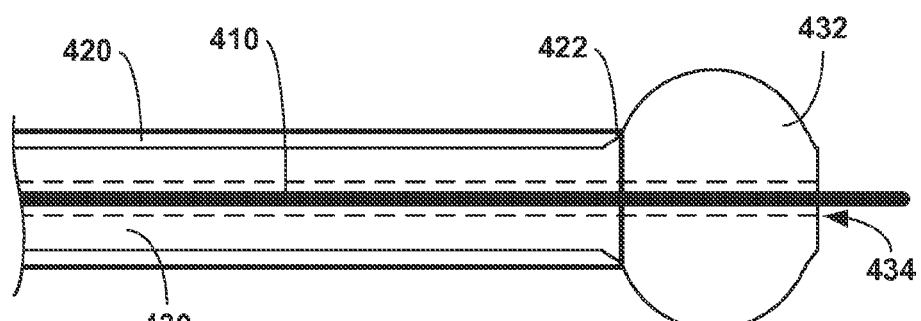

As represented by FIG. 11B, after distal end 412 of guidewire 410 is positioned proximate to a target site within the patient, the clinician routes an assembly including outer sheath 420 and inner sheath 430 over the proximal end guidewire 410 and pushes the assembly along guidewire 410 until distal opening 422 of outer sheath 420 is proximate the target site within the patient.

Elongated outer sheath 420 is sized to traverse the vasculature of the patient. Outer sheath 420 forms inner lumen 424, which has distal opening 422. In some examples, inner lumen 424 may extend the length of outer sheath 420 and also provide a proximal opening.

Elongated inner sheath 430 includes inflatable member 432. Inflatable member 432 is selectively inflatable from a proximal end of inner sheath 430. When inflated inflatable member 432 is configured to substantially fill inner lumen 424 of outer sheath 420 and close-off distal opening 422 of outer sheath 420.

Inner sheath 430 includes guidewire lumen 434, which may extend throughout the length of inner sheath 430. The diameter of guidewire lumen 434 at the distal portion of inner sheath 430 corresponds to the diameter of guidewire 410. In some examples, guidewire lumen 434 may be greater at other portions of inner sheath 430 than at the distal portion of inner sheath 430. Such a configuration may limit friction between guidewire 410 and inner sheath 430. In other examples, guidewire lumen 434 may have a consistent diameter throughout the length of inner sheath 430.

In the assembly of outer sheath 420 and inner sheath 430, inflatable member 432 extends beyond distal opening 422 of outer sheath 420; however, inner sheath 430 may be advanced and retracted relative to outer sheath 420 by the clinician during the implantation procedure, if desired, as inner sheath 430 is slidable within inner lumen 424 of outer sheath 420. For example, inflatable member 432 may be remotely deflated by the clinician. Once inflatable member 432 is deflated, the clinician may pull into inflatable member 432 into inner lumen 424 of outer sheath 420 by pulling on the proximal end of inner sheath 430.

Figure 11C:
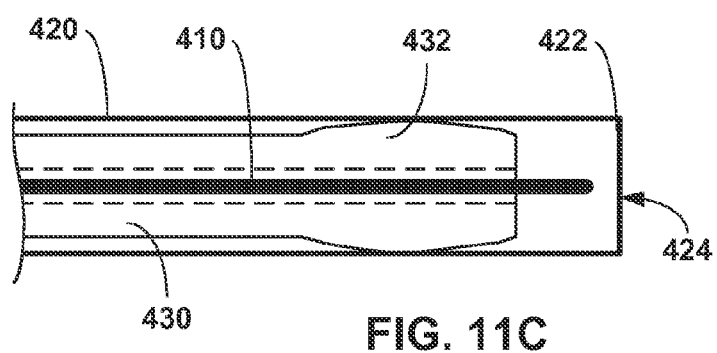
Figure 11D:
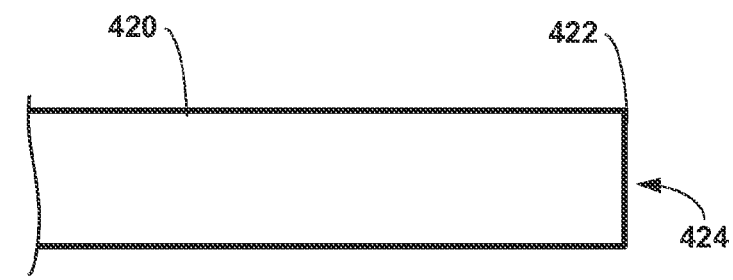

After the assembly of outer sheath 420 and inner sheath 430 is advanced along guidewire 410 until distal opening 422 of outer sheath 420 is proximate the target site within the patient (FIG. 11B), the clinician remotely deflates inflatable member 432 retracts inner sheath 430 and guidewire 410 into distal opening 422 of outer sheath 420 (FIG. 11C). Then guidewire 410 and inner sheath 430 are withdrawn from outer sheath 420 (FIG. 11D). For example, a clinician may simply pull on guidewire 410 and inner sheath 430 from a proximal end of outer sheath 420 to slide guidewire 410 and inner sheath 430 out of the proximal opening of outer sheath 420.

Inflatable member 432 serves to improve deliverability by protecting the distal edge of outer sheath 420. In addition, inflatable member 432 may enhance trackability by providing a distal force input on the assembly of outer sheath 420 and inner sheath 430. For example, inflatable member 432 can be inflated in the blood stream to allow blood flow to carry the assembly of outer sheath 420 and inner sheath 430 through the patient anatomy and ultimately to the target implant site. In addition, vessel sizing can be done by occluding a vasculature proximate to the target site and applying a localized contrast injection in combination with fluoroscopy.

Figure 12A:
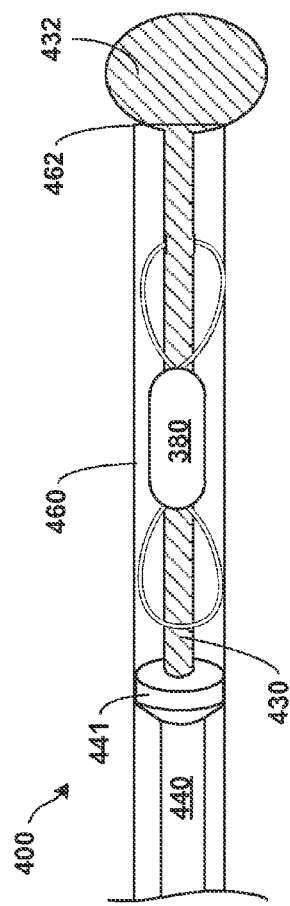
FIGS. 12A-12C illustrate example techniques for intravascular delivery of an IMD using a delivery catheter with a distal inflatable member.
Figure 12B:
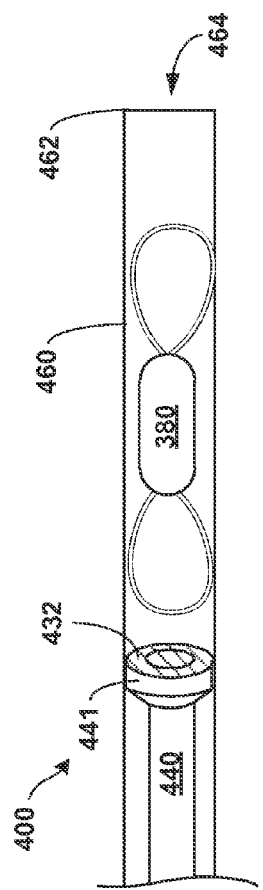
Figure 12C:
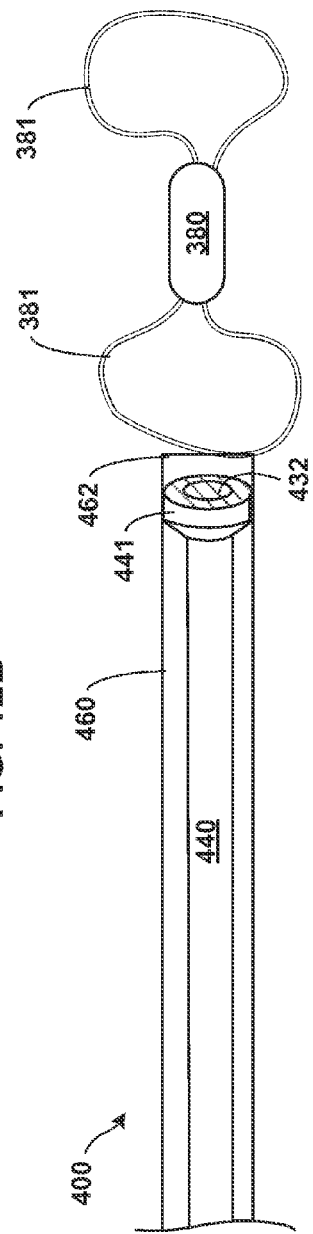

FIGS. 12A-12C illustrate example techniques for intravascular delivery of IMD 380 using delivery catheter 400. Delivery catheter 400 includes elongated outer sheath 460, which forms inner lumen 464 with distal opening 462. Delivery catheter 400 further includes inner sheath 440 with inflatable member 432 at its distal end. Delivery catheter 400 and outer sheath 460 is sized to traverse a vasculature of the patient, and delivery catheter 400 is configured to carry IMD 380 within a distal portion of inner lumen 464 of outer sheath 460 while traversing the vasculature of the patient. Inner sheath 440 is slidable within inner lumen 464 of outer sheath 460.

Inflatable member 432 may be constructed of a compliant polymer material or be constructed of less-compliant polymers, if so desired. The polymer material may have a low-pressure rating, as high-pressure capability is not required. The diameter of inflatable member 432 may controlled by inflation media volume. For example, inner sheath 440 may include an inflation lumen extending a length of inner sheath 440. The distal end of the inflation lumen terminates at inflatable member 432, whereas the proximal end of the inflation lumen terminates at an inflation control mechanism, like a syringe. The inflation media is normally, but not necessarily, a liquid, such as a saline solution; in other examples the inflation media may be a gas, such as air.

IMD 380 includes expandable fixation element 381, which is deployable from a collapsed position to an expanded position secure the IMD 380 proximate a target site within a patient. While FIGS. 12A-12C illustrate implantation techniques using IMD 380, in different examples, IMD 380 may be substantially similar to IMD 17 (FIG. 4) or IMD 15 (FIG. 5). As one example, the techniques of FIGS. 12A-12C may be used to deliver IMD 17 to a position within a heart of a patient, such as a position proximate to an inner wall of the right ventricle, within the right atrium, the left atrium, and/or left ventricle. As another example, the techniques of FIGS. 12A-12C may be used to deliver IMD 15 to an intravascular position such as a pulmonary artery or other vasculature of the patient.

During an implantation procedure, a clinician first positions delivery catheter 400 such that the distal end of outer sheath 460 is proximate to a target site within the patient via a vasculature accessed during a surgical procedure, as represented by FIG. 12A. For example, delivery catheter 400 may be advanced into an entry vessel, such as the femoral artery, and then manipulated and navigated through the patient's vasculature until the distal end of outer sheath 460 proximate to a target site within the patient. In different examples, delivery catheter 400 may be steerable or be configured to traverse a guidewire to be directed to the target site from the access point of the vasculature. The clinician may use imaging techniques, such as fluoroscopy, to monitor the position of outer sheath 460, inner sheath 440, and IMD 380 throughout the implantation procedure. In some examples, delivery catheter 400 may have an internal lumen for contrast injections.

Delivery catheter 400 further includes stopper 441, which is proximally located relative to inflatable member 432. Inflatable member 432 is remotely controllable from a proximal end of delivery catheter 400 to retract in a proximal direction towards inner sheath 440. Once the distal end of outer sheath 460 is proximate to a target site within the patient, the clinician may deflate inflatable member 432 and draw inflatable member 432 back towards stopper 441 prior to deployment of IMD 380. As represented by FIG. 12B, inflatable member 432 is retractable to a position within inner lumen 464 of outer sheath 460 that is proximal to IMD 380. Retracting inflatable member 432 to a position that is proximal to IMD 380 prior to deployment of IMD 380 prevents the opportunity for post-deployment interaction between inflatable member 432 and IMD 380. For example, if inflatable member 432 were not refracted to a position that is proximal to IMD 380 prior to deployment of IMD 380, inflatable member might catch on IMD 380 after IMD 380 were deployed, which could move or even dislodge IMD 380 from the target site within the patient.

Stopper 441 includes an enlarged distal end that facilitates deployment of IMD 380 out of distal opening 462 of outer sheath 460. Enlarged distal end 441 may include a recess to receive a deflated inflatable member 432. In any event, inner sheath 440 is remotely controllable from a proximal end of inner sheath 430 to release IMD 380 from the distal end of outer sheath 460. Once inflatable member 432 retracted to a position within inner lumen 464 of outer sheath 460 that is proximal to IMD 380, the clinician deploys IMD 380 from outer sheath 460. Specifically, a clinician, from the proximal end of inner sheath 440, may remotely move inner sheath 440 distally relative to deployment bay 442 to push IMD 380 out distal opening 462 of outer sheath 460. As shown in FIG. 12C, expandable fixation element 381 of IMD 380 is expanded from a collapsed position to an expanded position as IMD 380 passes out distal opening 462 of outer sheath 460. In one example, inner sheath 440 is held in a fixed location while outer sheath 460 is retracted proximally to release IMD 380 from distal opening 462 and allow the expansion of IMD 380 at the target location. In the expanded position, expandable fixation element 381 will secure IMD 380 within the patient, e.g., as described with respect to IMD 17 (FIG. 4) or IMD 15 (FIG. 5).

Delivery catheter 400 may provide one or more advantages. For example, inflatable member 432 may provide improved deliverability of delivery catheter 400 in the inflated state in that inflatable member 432 may cross tricuspid and pulmonary valves without issue or risk of damaging leaflets, e.g., to reach a target site within a pulmonary artery. Inflatable member 432 may also allow delivery catheter 400 to negotiate the chordae in the right ventricle without hanging up on the chordae. Furthermore, inflatable member 432 may be used to measure the size of a vasculature, which may be useful to find a target site having a vessel size corresponding to the size of expandable fixation element 381. As one example, a clinician may find a target site by applying a localized contrast injection while viewing delivery catheter 400 under fluoroscopy. Once a vasculature is fully occluded by inflatable member 432, the clinician would then know the size of the vasculature corresponds to the diameter of inflatable member 432. In some examples, the clinician may selectively inflatable member 432 to a size associated with a desired size of the vasculature and advance delivery catheter 400 within the vessel until a vasculature is fully occluded.

Figure 13A:
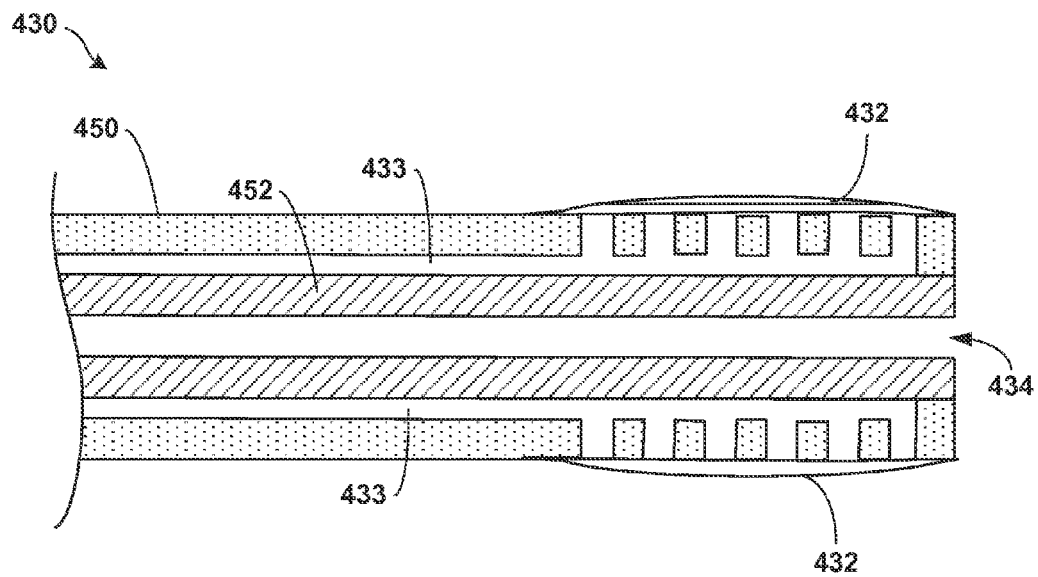
FIGS. 13A-13B illustrate the distal end of an inner sheath with an inflatable member as shown in FIGS. 12A-12C in further detail.
Figure 13B:
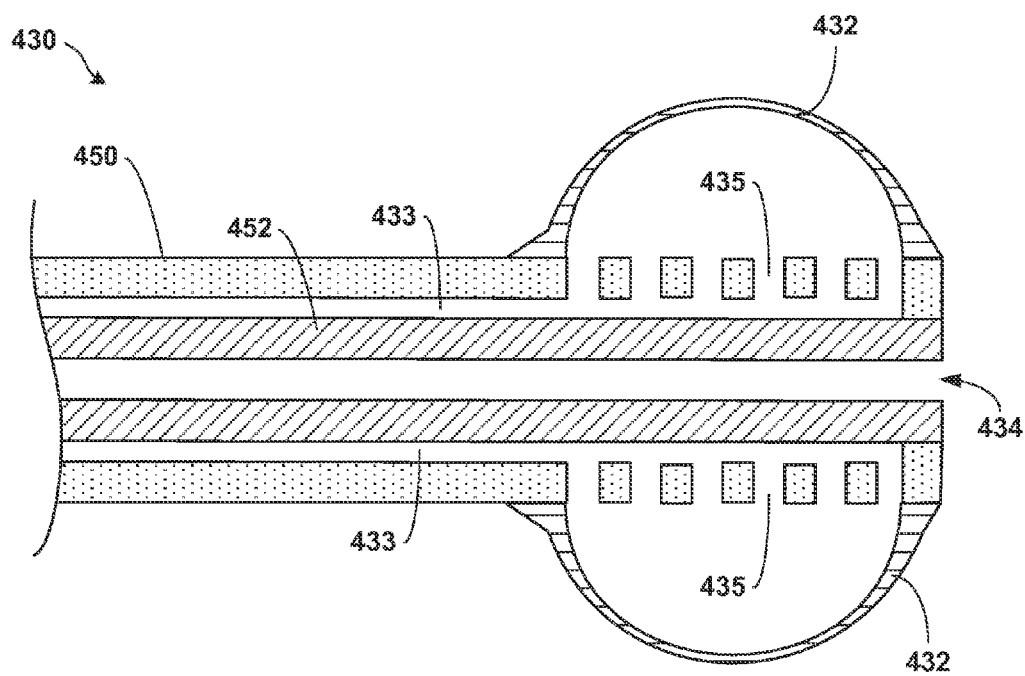

Inflatable member 432 is shown in further detail in FIGS. 13A-13B. Specifically, FIG. 13A is a cross-sectional illustration of inflatable member 432 in a deflated configuration, whereas FIG. 13B is a cross-sectional illustration of inflatable member 432 in an inflated configuration.

As shown in FIGS. 13A-13B, inner sheath 430 includes two coaxial lumens. Tube 452 provides central lumen 434 may serve as a guidewire lumen, and may also be suitable for contrast injections. Tube 450 surrounds tube 452 and provides annular inflation lumen 433. The distal end of annular inflation lumen 433 terminates at inflatable member 432, whereas the proximal end of annular inflation lumen 433 terminates at an inflation control mechanism, like a syringe. Inflatable member 432 is secured to the outside of tube 450 at the distal end of tube 450. Tube 450 includes apertures 435, which allow the inflation media to pass from within inflation lumen 433 to inflatable member 432. In other examples, tube 450 may include a single aperture in place of apertures 435. The area between the distal ends of tubes 450, 452 is sealed to direct the inflation media inflatable member 432. As mentioned previously, the inflation media is normally, but not necessarily, a liquid, such as a saline solution.

Figure 14:
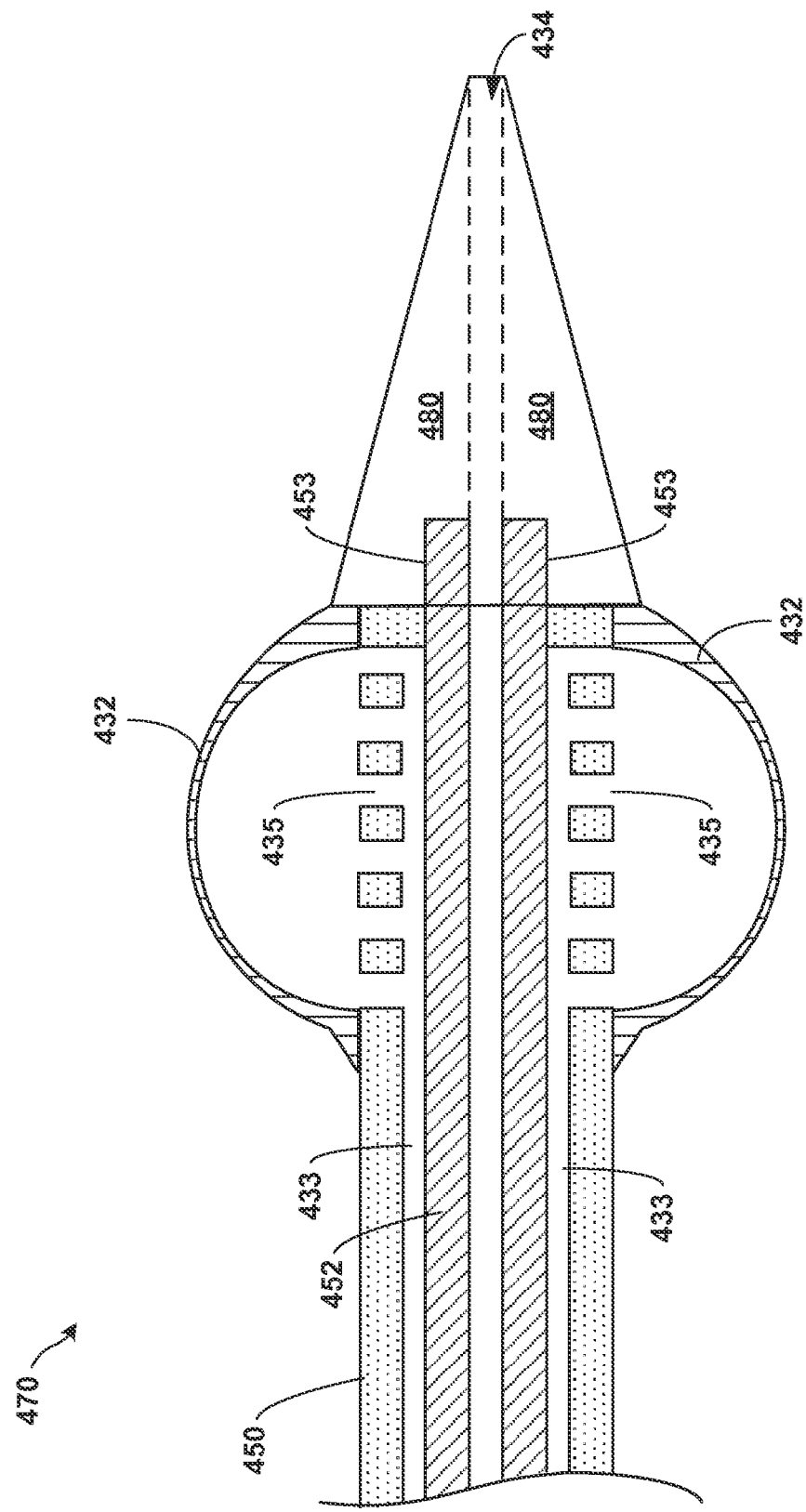
FIG. 14 illustrates the distal end of an inner sheath with an inflatable member and a distal tapered flexible tip.

FIG. 14 illustrates the distal end of inner sheath 470, which provides an alternative design as compared to inner sheath 430. Specifically, inner sheath 470 includes tapered flexible tip 480, which is located distally relative to inflatable member 432. Tapered flexible tip 480 is mounted to the distal end of tube 452, distally relative to inflatable member 432. Central lumen 434 extends through tube 452 and through tapered flexible tip 480. The other components and features of the distal end of inner sheath 470 are substantially similar to those of inner sheath 430. For brevity, these components and features are not discussed with respect to inner sheath 470.

Tapered flexible tip 480 is formed from a compliant biocompatible material, such as silicon. Tapered flexible tip 480 may serve to help a delivery catheter, such as delivery catheter 400, navigate a guidewire to negotiate the vasculature of a patient. For example, tapered flexible tip 480 may lead inflatable member 432 around bends, vascular branches and through valves such as tricuspid and pulmonary valves, the chordae in the right ventricle and other obstacles during positioning of a delivery catheter. Thus, tapered flexible tip 480 may improve the deliverability of delivery catheter by preventing hang-ups during insertion of the delivery catheter. In some examples, the material of tapered flexible tip 480 may be doped with radiopaque materials (such as barium sulfate) to aid a clinician during implant.

FIGS. 15A-15F illustrate exemplary techniques for intravascular delivery of IMD 380 using delivery catheter 500. Delivery catheter 500 includes elongated outer sheath 520 and elongated inner sheath 540. Delivery catheter 500 and outer sheath 520 are sized to traverse a vasculature of the patient, and delivery catheter 500 is configured to carry IMD 380 within a distal portion of inner lumen 524 of outer sheath 520 while traversing the vasculature of the patient. Inner sheath 540 is slidable within outer sheath 520 and includes enlarged distal portion 532 and tether 550. Enlarged distal portion 532 provides a tapered distal end. Alternatively, an enlarged distal portion may be selected from the examples shown previously with respect to FIGS. 13-14. In some examples, inner sheath 540 and enlarged distal portion 532 may include a lumen (not shown) configured to receive a guidewire and/or deliver contrast injections during an implantation procedure.

IMD 380 includes expandable fixation element 381, which is deployable from a collapsed position to an expanded position secure the IMD 380 proximate a target site within a patient. While FIGS. 15A-15F illustrate implantation techniques using IMD 380, in different examples, IMD 380 may be substantially similar to IMD 17 (FIG. 5) or IMD 15 (FIG. 5). As one example, the techniques of FIGS. 15A-15F may be used to deliver IMD 17 to a position within a heart of a patient, such as a position proximate to an inner wall of the right ventricle, within the right atrium, the left atrium, and/or left ventricle. As another example, the techniques of FIGS. 15A-15F may be used to deliver IMD 15 to an intravascular position such as a pulmonary artery or other vasculature of the patient.

During an implantation procedure, a clinician first positions delivery catheter 500 such that the distal end of outer sheath 520 is proximate to a target site within the patient via a vasculature accessed during a surgical procedure, as represented by FIG. 15A. For example, delivery catheter 500 may be advanced into an entry vessel, such as the femoral artery, and then manipulated and navigated through the patient's vasculature until the distal end of outer sheath 520 proximate to a target site within the patient. In different examples, delivery catheter 500 may be steerable or be configured to traverse a guidewire to be directed to the target site from the access point of the vasculature. The clinician may use imaging techniques, such as fluoroscopy, to monitor the position of outer sheath 520, inner sheath 540, and IMD 380 throughout the implantation procedure. In some examples, delivery catheter 500 may have an internal lumen for contrast injections. Enlarged distal portion 532 is configured to substantially fill inner lumen 524 of outer sheath 520 and close-off distal opening 522 of outer sheath 520 while delivery catheter 500 is advanced to a location proximate a target site within a patient. As one example, enlarged distal portion 532 may provide a tapered distal end with a profile larger than a cross section of inner lumen 524 of outer sheath 520 such that the tapered distal end cannot pass through inner lumen 524.

After positioning the distal end of outer sheath 520 is proximate to a target site within the patient, the clinician moves enlarged distal portion 532 distally relative to distal opening 522 of outer sheath 520 to allow room for IMD 380 to deploy from distal opening 522 of outer sheath 520 (FIG. 15B). In some examples, the clinician may retract sheath 520 proximally to expose and allow fixation of IMD 380 to seat in a vessel wall. Thereafter, tip 532 is retracted while helix 552 insures that IMD 380 is not dislodged from the vessel wall while tip 532 is retracted past the implant.

Inner sheath 540 facilitates deployment of IMD 380 out of distal opening 522 of outer sheath 520. In particular, inner sheath 540 includes tether 550, which has helical element 552 on its distal end. Tether 550 is remotely controllable from a proximal end of inner sheath 540 to release IMD 380 from the distal end of outer sheath 520. Specifically, a clinician, from the proximal end of inner sheath 540, may remotely push tether 550 distally relative to the distal end of outer sheath 520 to push IMD 380 out distal opening 522 of outer sheath 520, e.g., by holding tether 550 in place and retracting outer sheath 520 (FIG. 15C). As shown in FIG. 15C, a portion of expandable fixation element 381 of IMD 380 is expanded from a collapsed position to an expanded position as IMD 380 passes out of distal opening 522 of the distal end of outer sheath 520. In the expanded position, expandable fixation element 381 will secure IMD 380 within the patient, e.g., as described with respect to IMD 17 (FIG. 4) or IMD 15 (FIG. 5).

Figure 15D:
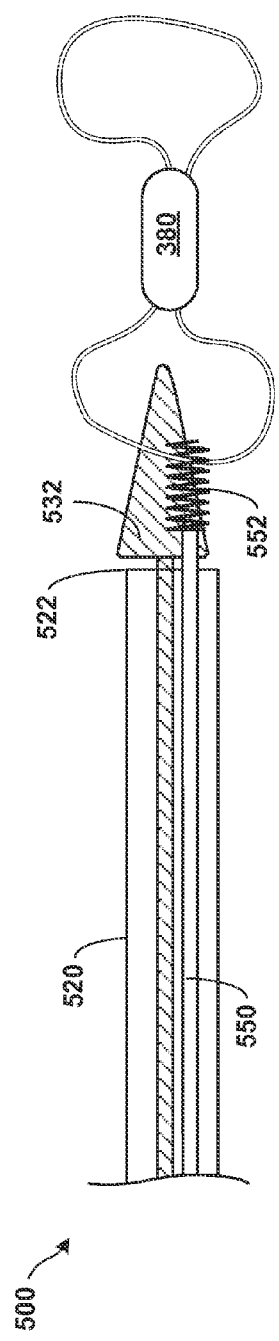
Figure 15E:
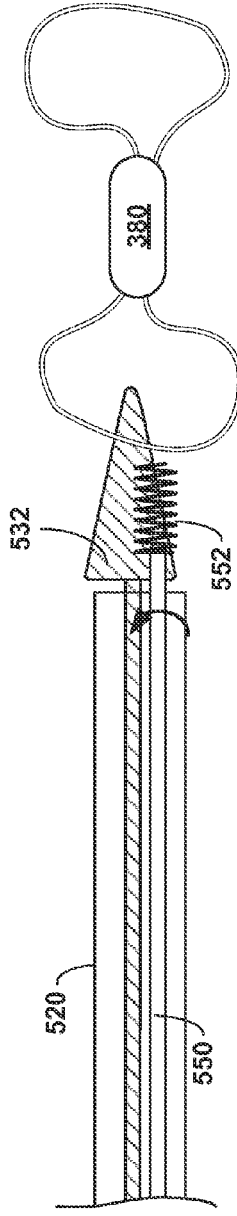

Then the clinician may, again from the proximal end of inner sheath 540, move enlarged distal portion 532 proximally towards distal opening 522 of outer sheath 520, past IMD 380 and helical element 552 while helical element 552 remains engaged to the looped fixation element of IMD 380 (FIG. 15D). In this manner, IMD 380 is not fully deployed when enlarged distal portion 532 is retracted past IMD 380. Once the clinician retracts enlarged distal portion 532 proximally past IMD 380 and helical element 552, the clinician may, again from the proximal end of inner sheath 540, remotely rotate tether 550 such that helical element 552 releases a looped element of IMD 380 to deploy IMD 380 (FIG. 15E). Specifically, in the example illustrated in FIG. 15E, expandable fixation element 381 is the looped element of IMD 380, and rotating helical element 552 releases expandable fixation element 381 from inner sheath 540.

At this point, IMD 380 is fully deployed proximate to the target site, e.g., within a vasculature of the patient. However, the clinician may optionally recapture IMD 380 by first grabbing a looped element of IMD 380, e.g., expandable fixation element 381, with helical element 552, and then using tether 550 to pull IMD 380 into the distal end of outer sheath 520. In this manner, tether 550 may be used to adjust the position of IMD 380 after full deployment, or to remove IMD 380 from the patient after full deployment. As one example, the clinician may decide to remove IMD 380 from the patient after full deployment if electronic testing of IMD 380 produces unsatisfactory results. As another example, the clinician may decide to remove IMD 380 from the patient after full deployment if the clinician determines that expandable fixation element 381 is improperly sized to locate IMD 380 at the target site. In such an example, IMD 380 may be replaced with an IMD including an expandable fixation element with a proper size. As another example, a clinician may use delivery catheter 500 to remove IMD 380 during a subsequent surgical procedure, e.g., once IMD 380 has met or exceeded its projected lifespan. During such a subsequent surgical procedure, IMD 380 could be replaced with a new IMD using the same outer sheath used during the removal of IMD 380.

Figure 15F:
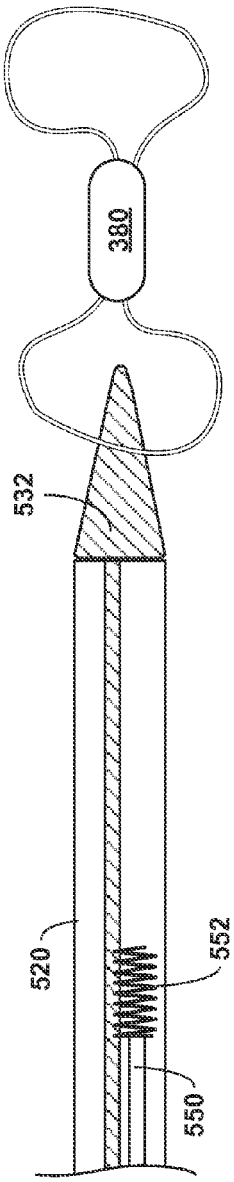

After IMD 380 is fully deployed proximate to the target site, the clinician retracts tether 550 and enlarged distal portion 532 into inner lumen 524 of outer sheath 520 and withdraws delivery catheter 500 (FIG. 15F).

FIGS. 16A-16B illustrate example techniques for intravascular delivery of IMD 380 using delivery catheter 560. Delivery catheter 560 includes elongated outer sheath 520 and elongated inner sheath 570. Delivery catheter 560 and outer sheath 520 are sized to traverse a vasculature of the patient, and delivery catheter 560 is configured to carry IMD 380 within a distal portion of inner lumen 524 of outer sheath 520 while traversing the vasculature of the patient. Inner sheath 570 is slidable within outer sheath 520 and includes enlarged distal portion 562 and tether 552.

Delivery catheter 560 is substantially similar to delivery catheter 500, except that enlarged distal portion 562 includes an inflatable member. In some examples, inner sheath 570 and enlarged distal portion 562 may include a lumen (not shown) configured to receive a guidewire and/or deliver contrast injections during an implantation procedure. For example, the inflatable member of enlarged distal portion 562 may be functionally similar to inflatable member 432 (FIGS. 13A-13B) and may optionally include a tapered flexible tip, such as tapered flexible tip 480 (FIG. 14). The other components and features of delivery catheter 560 are substantially similar to those of delivery catheter 500. For brevity, these components and features are discussed in limited detail with respect to delivery catheter 560.

During an implantation procedure, a clinician first positions delivery catheter 560 such that the distal end of outer sheath 520 is proximate to a target site within the patient via a vasculature accessed during a surgical procedure, as represented by FIG. 16A. For example, delivery catheter 560 may be advanced into an entry vessel, such as the femoral artery, and then manipulated and navigated through the patient's vasculature until the distal end of outer sheath 520 proximate to a target site within the patient. In different examples, delivery catheter 560 may be steerable or be configured to traverse a guidewire to be directed to the target site from the access point of the vasculature. The clinician may use imaging techniques, such as fluoroscopy, to monitor the position of outer sheath 520, inner sheath 570, and IMD 380 throughout the implantation procedure.

Enlarged distal portion 562 is configured to substantially fill inner lumen 524 of outer sheath 520 and close-off distal opening 522 of outer sheath 520 while the inflatable member of enlarged distal portion 562 is inflated. The inflatable member of enlarged distal portion 562 is generally inflated while delivery catheter 560 is advanced to a location proximate a target site within a patient. After positioning the distal end of outer sheath 520 is proximate to a target site within the patient, the clinician deflates the inflatable member of enlarged distal portion 562 and retracts enlarged distal portion 562 proximally into inner lumen 524 of outer sheath 520 to a position that is proximal to IMD 380 within inner lumen 524 of outer sheath 520.

Inner sheath 570 facilitates deployment of IMD 380 out of distal opening 522 of outer sheath 520. In particular, inner sheath 570 includes tether 550, which has helical element 552 on its distal end. Tether 550 is remotely controllable from a proximal end of inner sheath 570 to release IMD 380 from the distal end of outer sheath 520. Specifically, a clinician, from the proximal end of inner sheath 570, may remotely push tether 550 distally relative to the distal end of outer sheath 520 to push IMD 380 out distal opening 522 of outer sheath 520 (FIG. 16B). As shown in FIG. 16B, expandable fixation element 381 of IMD 380 is expanded from a collapsed position to an expanded position as IMD 380 passes out of distal opening 522 of the distal end of outer sheath 520. In the expanded position, expandable fixation element 381 will secure IMD 380 within the patient, e.g., as described with respect to IMD 17 (FIG. 4) or IMD 15 (FIG. 5).

Once the clinician retracts enlarged distal portion 562 proximally past IMD 380 and helical element 552, the clinician may, again from the proximal end of inner sheath 570, remotely rotate tether 550 such that helical element 552 releases a looped element of IMD 380 to deploy IMD 380.

At this point, IMD 380 is fully deployed proximate to the target site, e.g., within a vasculature of the patient. However, the clinician may optionally recapture IMD 380 by first grabbing a looped element of IMD 380, e.g., expandable fixation element 381, with helical element 552, and then using tether 550 to pull IMD 380 into the distal end of outer sheath 520. In this manner, tether 550 may be used to adjust the position of IMD 380 after full deployment, or to remove IMD 380 from the patient after full deployment.

FIGS. 17A-17E illustrate exemplary techniques for intravascular delivery of IMD 380 with a kit including outer sheath 620 and inner sheath 640. Inner sheath 640 is configured to carry IMD 380 at its distal end. Inner sheath 640 forms a slit at its distal end to facilitate deployment of IMD 380. Specifically, FIGS. 17A-17E illustrate distal portions of outer sheath 620 and elongated inner sheath 640. In some examples, outer sheath 620 may be considered to be substantially similar to outer sheath 234. For example, outer sheath 620 may be included in an assembly with coupling module 206. In such an example, inner sheath 640 may be slidably coupled to coupling module 226 in a mating assembly, and the distal end of inner sheath 640 may be positioned proximate a target site within a patient in a similar manner that inner sheath 202 is positioned proximate a target site within a patient as described with respect to FIGS. 8A-8E.

While FIGS. 17A-17E illustrate implantation techniques using IMD 380, in different examples, IMD 380 may be substantially similar to IMD 17 (FIG. 4) or IMD 15 (FIG. 5). As one example, the techniques of FIGS. 17A-17E may be used to deliver IMD 17 to a position within a heart of a patient, such as a position proximate to an inner wall of the right ventricle, within the right atrium, the left atrium, and/or left ventricle. As another example, the techniques of FIGS. 17A-17E may be used to deliver IMD 15 to an intravascular position such as a pulmonary artery or other vasculature of the patient.

The distal end of inner sheath 640 is configured to carry IMD 380 through inner lumen 624 of outer sheath 620, and inner sheath 640 is slidable within inner lumen 624 of outer sheath 620. Inner sheath 640 facilitates deployment of IMD 380 out of distal opening 622 of outer sheath 620. In particular, inner sheath 640 forms slit 641, which allows inner sheath 640 to uncurl to expose the IMD 380 when the distal end of inner sheath 640 passes out of distal opening 622 of outer sheath 620. The distal end of inner sheath 640 is elastically deformed within inner lumen 624 such that the distal end of inner sheath 640 is biased to uncurl and expose IMD 380 when the distal end of inner sheath 640 passes out of distal opening 622 of outer sheath 620.

Figure 17A:
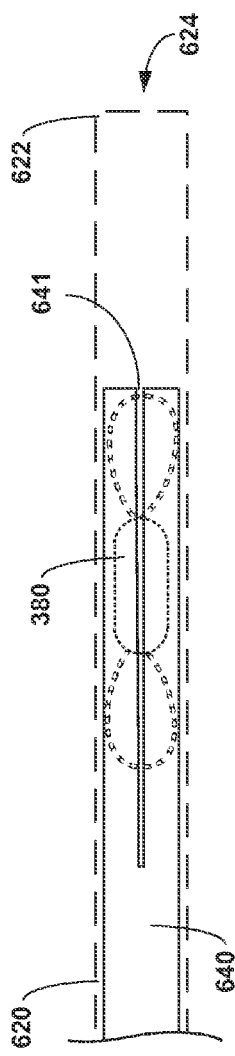

During an implantation procedure, a clinician may first position outer sheath 620 such that distal opening 622 of outer sheath 620 is proximate to a target site within the patient via a vasculature accessed during a surgical procedure, as represented by FIG. 17A. For example, outer sheath 620 may be advanced into an entry vessel, such as the femoral vein and then manipulated and navigated through the patient's vasculature distal opening 622 of outer sheath 620 is proximate to a target site within the patient. In different examples, outer sheath 620 may be steerable or be configured to traverse a guidewire to be directed to the target site from the access point of the vasculature. The clinician may use imaging techniques, such as fluoroscopy, to monitor the position of outer sheath 620, inner sheath 640, and IMD 380 throughout the implantation procedure.

After locating distal opening 622 of outer sheath 620 proximate to a target site within the patient, the clinician may remotely push inner sheath 640 distally relative to outer sheath 620 to expose the distal end of inner sheath 640 and IMD 380, e.g., by holding inner sheath 640 in place and retracting outer sheath 620. IMD 380 includes expandable fixation element 381, which is deployable from a collapsed position to an expanded position secure the IMD 380 proximate a target site within a patient. When exposed, a portion of expandable fixation element 381 may assume the expanded position, as shown in FIG. 17B.

Figure 17B:
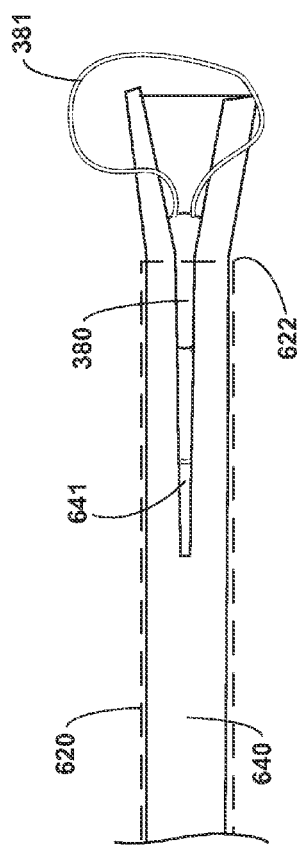

As shown in FIG. 17B, IMD 380 is partially deployed from inner sheath 640. Only a portion of expandable fixation element 381 has assumed the expanded position. At this point, the clinician may retract the distal end of inner sheath 640 into inner lumen 624 of outer sheath 620 to return the IMD 380 to inner lumen 624 of outer sheath 620. When the distal end of inner sheath 640 and IMD 380 are returned to inner lumen 624 of outer sheath 620, the distal end of inner sheath 640 curls and the expanded portion of expandable fixation element 381 resumes collapsed position to fit within inner lumen 624 of outer sheath 620.

As one example, the clinician may partially deploy IMD 380 and perform electronic testing of IMD 380, as sensing elements of IMD 380, such as a pressure sensor, may be exposed when IMD 380 is partially deployed. The clinician may decide to remove IMD 380 from the patient after partial deployment if testing results are unsatisfactory or if the clinician determines that expandable fixation element 381 is improperly sized to locate IMD 380 at the target site. In such an example, IMD 380 may be replaced with an IMD including an expandable fixation element with a proper size.

Figure 17C:
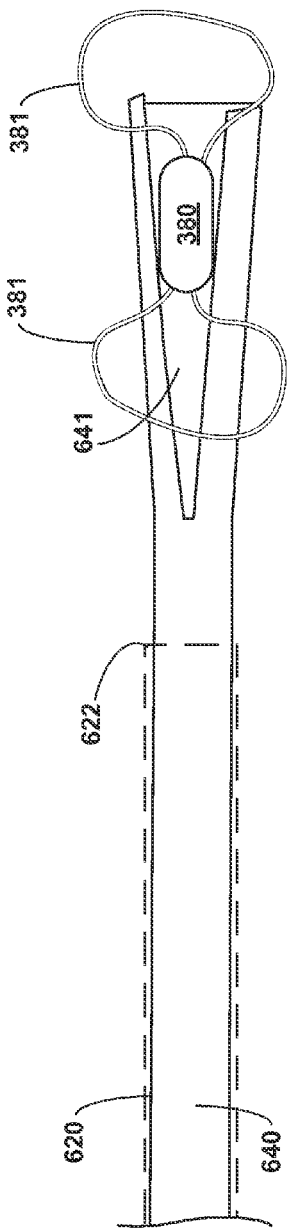

As represented by FIG. 17C, once IMD 380 is fully exposed, at least a portion of expandable fixation element 381 of IMD 380 has assumed the expanded position. In order to fully deploy IMD 380 from inner sheath 640, the clinician then retracts inner sheath 640 into inner lumen 624 of outer sheath 620 after the portion of expandable fixation element 381 assumes the expanded position (FIG. 17D). This causes the distal end of outer sheath 620 to interact with expandable fixation element 381 to slide IMD 380 out of inner lumen 624 of outer sheath 620 (FIG. 17E). In an example, the clinician may hold inner sheath 640 in place while advancing outer sheath 620 to cause the distal end of outer sheath 620 to interact with expandable fixation element 381 to slide IMD 380 out of inner lumen 624 of outer sheath 620.

Figure 18A:
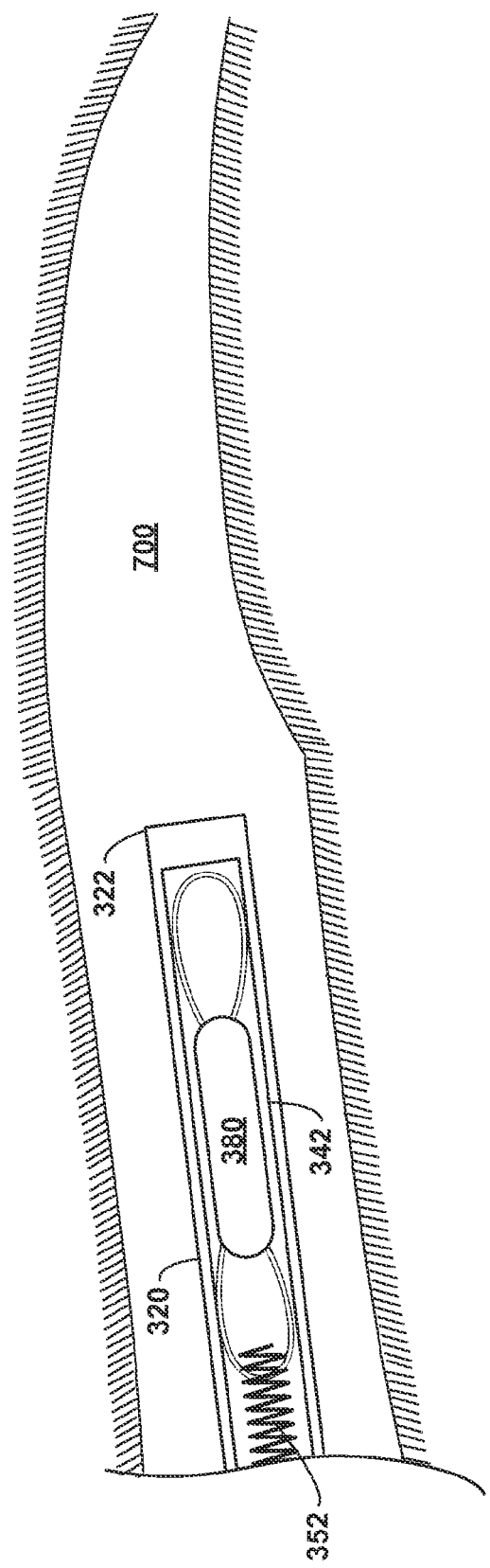
FIGS. 18A-18C illustrate example techniques for measuring the size of a vasculature using a partially deployed IMD within the deployment receptacle of FIGS. 10A-10D.
Figure 18B:
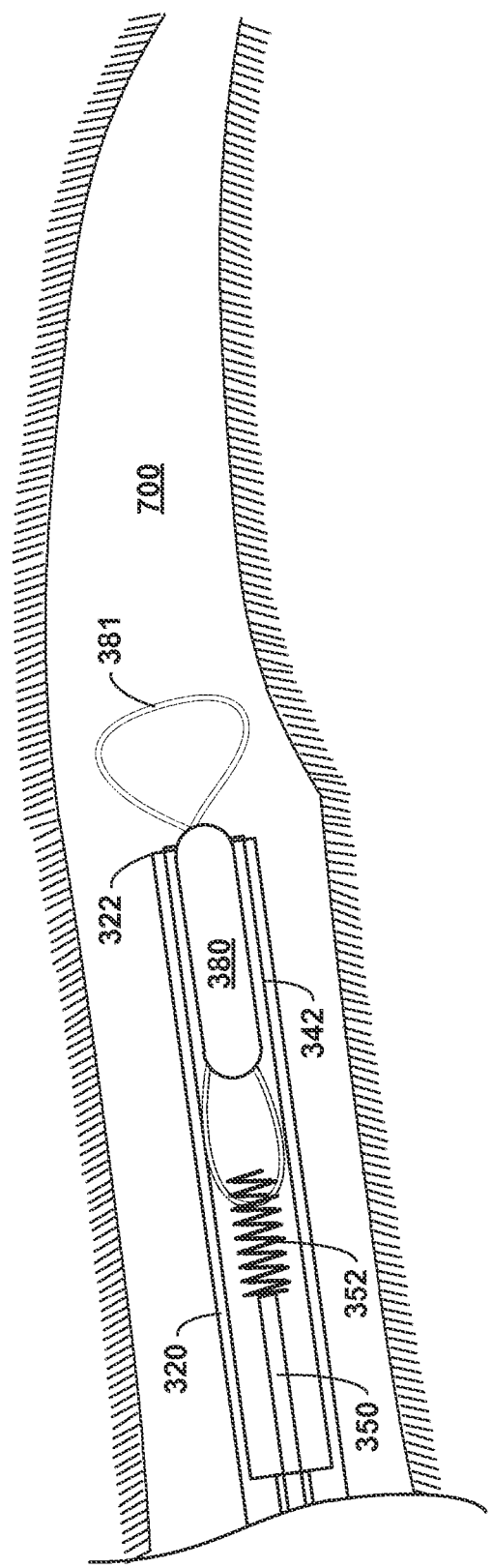
Figure 18C:
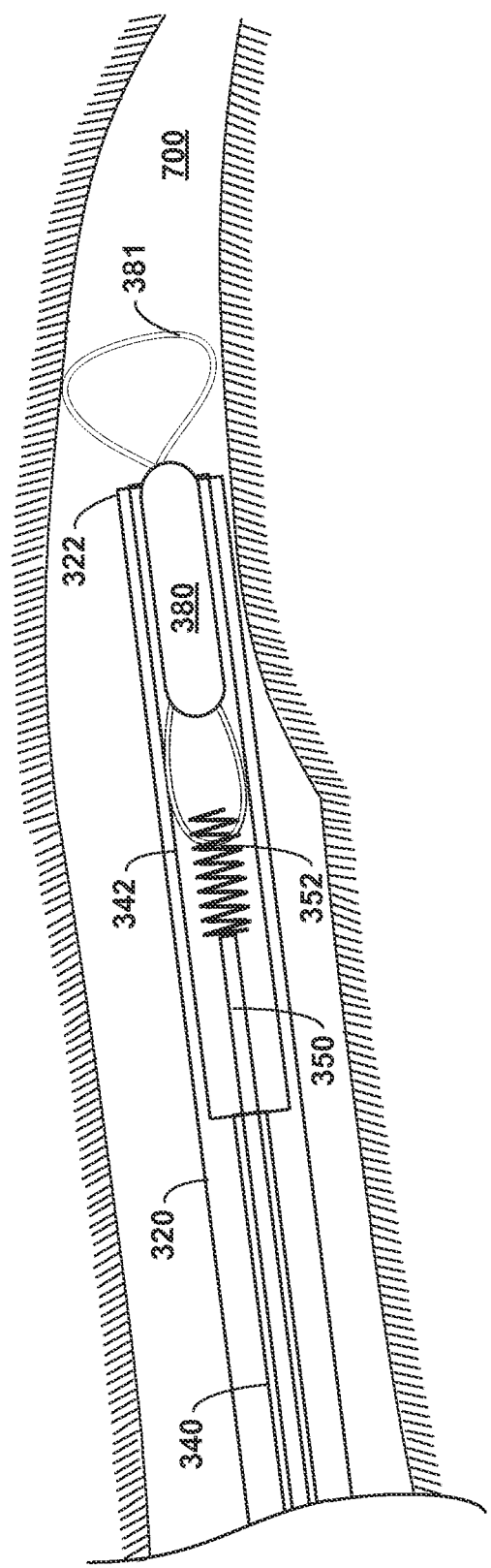

FIGS. 18A-18C illustrate techniques for measuring the size of vasculature 700 using deployment receptacle 340 of FIGS. 10A-10D with IMD 380 partially deployed from deployment receptacle 340. As shown in FIG. 18A, the distal end of deployment receptacle 340, which includes deployment bay 342, is delivered adjacent a target site within vasculature 700 through outer sheath 320. As one example, vasculature 700 may be a pulmonary artery or other vasculature of the patient.

Tether 350 with helical element 352 is then used to partially deploy IMD 380 from distal opening 322 of outer sheath 320. As shown in FIG. 18B, a portion of expandable fixation element 381 assumes the expanded position when IMD 380 is partially deployed from the distal opening.

Outer sheath 320, deployment receptacle 340 and the partially deployed IMD 380 is then advanced within the vasculature (FIG. 18C). A clinician monitors the process of outer sheath 320, deployment receptacle 340 and the partially deployed IMD 380. Specifically, the clinician monitors vasculature 700 and/or the expanded portion of expandable fixation element 381 for deflection to determine when the size of the expanded portion of expandable fixation element 381 corresponds to the size of vasculature 700. For example, vasculature 700 may be tapered, and IMD 380 may be configured to best fit when the size of the expanded portion of expandable fixation element 381 corresponds to the size of vasculature 700. In this manner, the expanded portion of expandable fixation element 381 may be used to measure the size of vasculature 700 to determine a target side for deployment of IMD 380 within vasculature 700. Deflection by either vasculature 700 or the expanded portion of expandable fixation element 381 may indicate the size of the expanded portion of expandable fixation element 381 corresponds to the size of vasculature 700.

In an example, the clinician may use fluoroscopy to view vasculature 700 and/or the expanded portion of expandable fixation element 381 while advancing outer sheath 320, deployment receptacle 340 and the partially deployed IMD 380 within vasculature 700. The clinician may also inject a contrast dye within vasculature 700 to aid in the monitoring of the expanded portion of expandable fixation element 381 and vasculature 700.

Once the clinician determines when the size of the expanded portion of expandable fixation element 381 corresponds to the size of vasculature 700, the clinician may deploy IMD 380 within vasculature 700 in accordance with the techniques described with respect to FIGS. 10A-10D.

Figure 19:
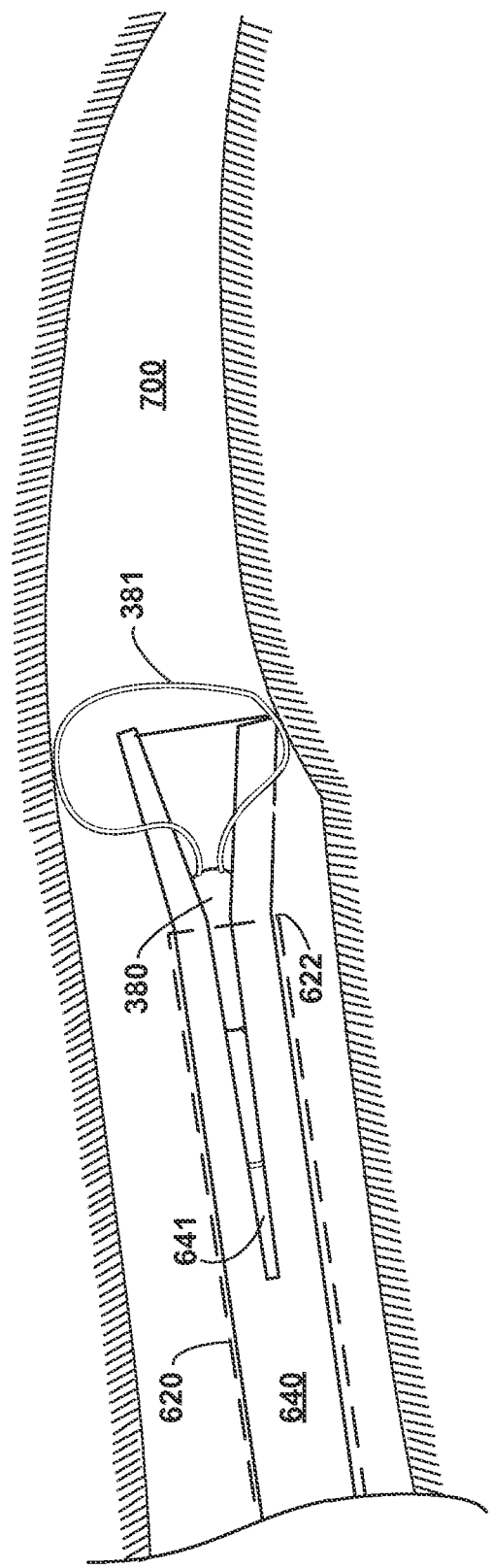
FIG. 19 illustrates example techniques for measuring the size of a vasculature using a partially deployed IMD within the inner sheath of FIGS. 17A-17E.

FIG. 19 illustrates techniques for measuring the size of vasculature 700 using outer sheath 620 and inner sheath 640 of FIGS. 17A-17E with IMD 380 partially deployed from inner sheath 640. The distal end of inner sheath 640 is delivered adjacent a target site within vasculature 700 through outer sheath 320. As one example, vasculature 700 may be a pulmonary artery or other vasculature of the patient.

Inner sheath 640 is then used to partially deploy IMD 380 from distal opening 622 of outer sheath 620. As shown in FIG. 19, a portion of expandable fixation element 381 assumes the expanded position when IMD 380 is partially deployed from distal opening 622 of outer sheath 620.

Outer sheath 620, inner sheath 640 and the partially deployed IMD 380 is then advanced within the vasculature. A clinician monitors the process of outer sheath 620, inner sheath 640 and the partially deployed IMD 380. Specifically, the clinician monitors vasculature 700 and/or the expanded portion of expandable fixation element 381 for deflection to determine when the size of the expanded portion of expandable fixation element 381 corresponds to the size of vasculature 700. For example, vasculature 700 may be tapered, and IMD 380 may be configured to best fit when the size of the expanded portion of expandable fixation element 381 corresponds to the size of vasculature 700. In this manner, the expanded portion of expandable fixation element 381 may be used to measure the size of vasculature 700 to determine a target side for deployment of IMD 380 within vasculature 700. Deflection by either vasculature 700 or the expanded portion of expandable fixation element 381 may indicate the size of the expanded portion of expandable fixation element 381 corresponds to the size of vasculature 700.

In an example, the clinician may use fluoroscopy to view vasculature 700 and/or the expanded portion of expandable fixation element 381 while advancing outer sheath 620, inner sheath 640 and the partially deployed IMD 380 within vasculature 700. The clinician may also inject a contrast dye within vasculature 700 to aid in the monitoring of the expanded portion of expandable fixation element 381 and vasculature 700.

Once the clinician determine when the size of the expanded portion of expandable fixation element 381 corresponds to the size of vasculature 700, the clinician may deploy IMD 380 within vasculature 700 in accordance with the techniques described with respect to FIGS. 17A-17E.

Figure 20:
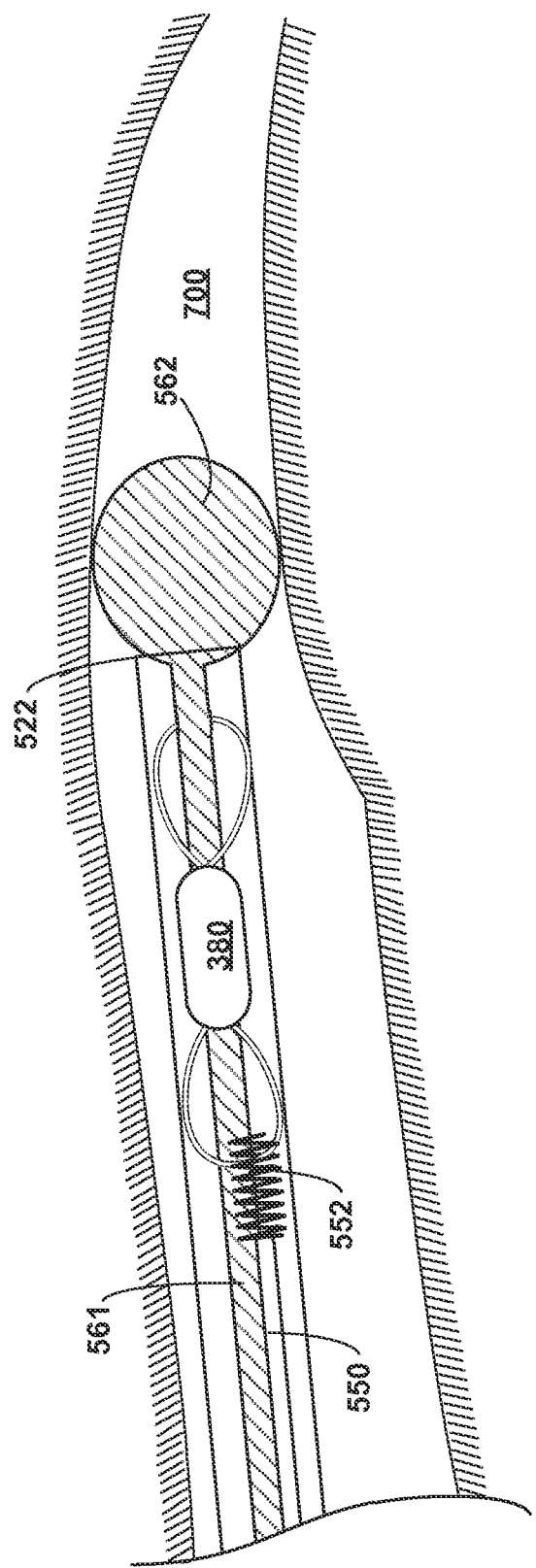
FIG. 20 illustrates example techniques for measuring the size of a vasculature using the delivery catheter with an inner sheath including an inflatable distal portion of FIGS. 16A-16B.

FIG. 20 illustrates techniques for measuring the size of vasculature 700 using delivery catheter 500 of FIGS. 16A-16B. As described previously, delivery catheter 500 includes inner sheath 540 with inflatable distal portion 562. As shown in FIG. 20, the distal end of outer sheath 520 is delivered adjacent a target site within vasculature 700. As one example, vasculature 700 may be a pulmonary artery or other vasculature of the patient.

Inflatable distal portion 562 may be inflated during the insertion of delivery catheter 500 as described with respect to FIGS. 16A-16B. Inflatable distal portion 562 may be used to measure the size of vasculature 700. For example, a clinician may monitor vasculature 700 during the insertion of delivery catheter 500; once vasculature 700 is occluded by inflatable distal portion 562, the clinician will know that the size of vasculature 700 at that location corresponds to the inflated size of inflatable distal portion 562. In some examples, the clinician may adjust the inflated size of inflatable distal portion 562 to measure the size of vasculature 700. In other examples, the clinician may maintain the inflated size of inflatable distal portion 562 to find the location within vasculature 700 that corresponds to the inflated size of inflatable distal portion 562. In any event, once the clinician has found a suitable target site within vasculature 700, the clinician may deploy IMD 380 from delivery catheter 500 in accordance with the techniques described with respect to FIGS. 16A-16B.

Figure 21:
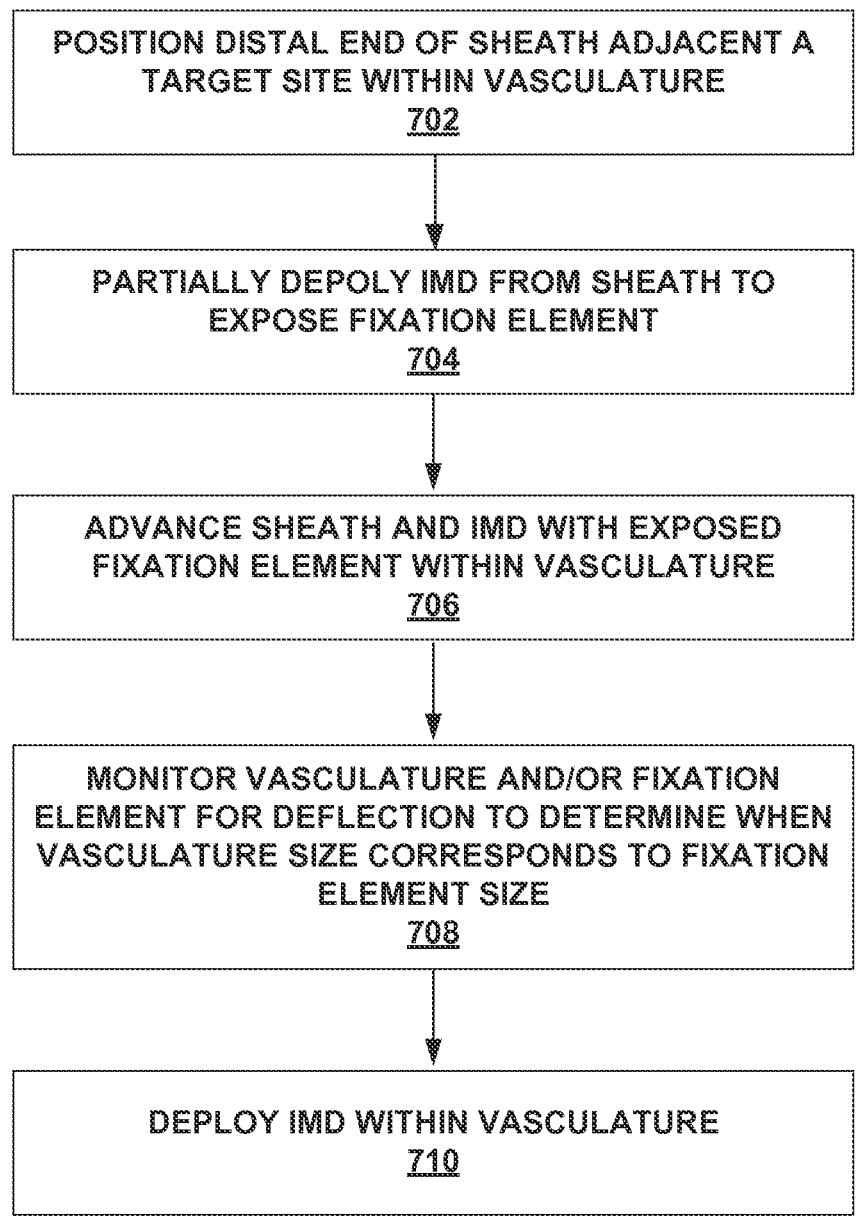
FIG. 21 is a flowchart illustrating example techniques for measuring the size of a vasculature using a partially deployed IMD.

FIG. 21 is a flowchart illustrating techniques for measuring the size of a vasculature using a partially deployed IMD. For example, the techniques of FIG. 21 may be performed using deployment receptacle 340 of FIGS. 10A-10D or using outer sheath 620 and inner sheath 640 of FIGS. 17A-17E. In a further example, the techniques of FIG. 21 may be performed using the system for intravascular delivery of an IMD described with respect to FIGS. 6-8E.

First, a distal end of an elongated outer sheath forming an inner lumen with a distal opening is positioned adjacent a target site within a vasculature of a patient (702). Then an IMD is partially deployed from the distal opening of the outer sheath (704). The IMD includes an expandable fixation element expandable from a collapsed position to an expanded position, and at least a portion of the expandable fixation element assumes the expanded position when the implantable medical device is partially deployed from the distal opening.

After the IMD is partially deployed from the distal opening of the outer sheath, the distal end of the outer sheath with the implantable medical device partially deployed from the distal opening is advanced within the vasculature (706). While advancing the distal end of the outer sheath with the implantable medical device partially deployed from the distal opening, at least one of the vasculature and the portion of the expandable fixation element is monitored for deflection to determine when the size of the portion of the expandable fixation element corresponds to the size of the vasculature (708). Monitoring at least one of the vasculature and the portion of the expandable fixation element for deflection may include using fluoroscopy to view at least one of the vasculature and the portion of the expandable fixation element while advancing the distal end of the outer sheath within the vasculature. In addition, monitoring at least one of the vasculature and the portion of the expandable fixation element for deflection may also include injecting a contrast dye within the vasculature.

After determining the size of the portion of the expandable fixation element corresponds to the size of the vasculature, the techniques may include fully releasing the implantable medical device to deploy the implantable medical device within the vasculature (710).

In examples in which the IMD includes a pressure sensor, the techniques may further include monitoring pressure within the vasculature with the pressure sensor with the implantable medical device partially deployed from the distal opening to test the functionality of IMD at that location, and after verifying the functionality of implantable medical device at that location, fully releasing the implantable medical device to deploy the implantable medical device within the vasculature. For example, such a testing may include receiving an indication of the monitored pressure from the IMD with an external programmer, such as programmer 24 (FIG. 1).

Figure 22:
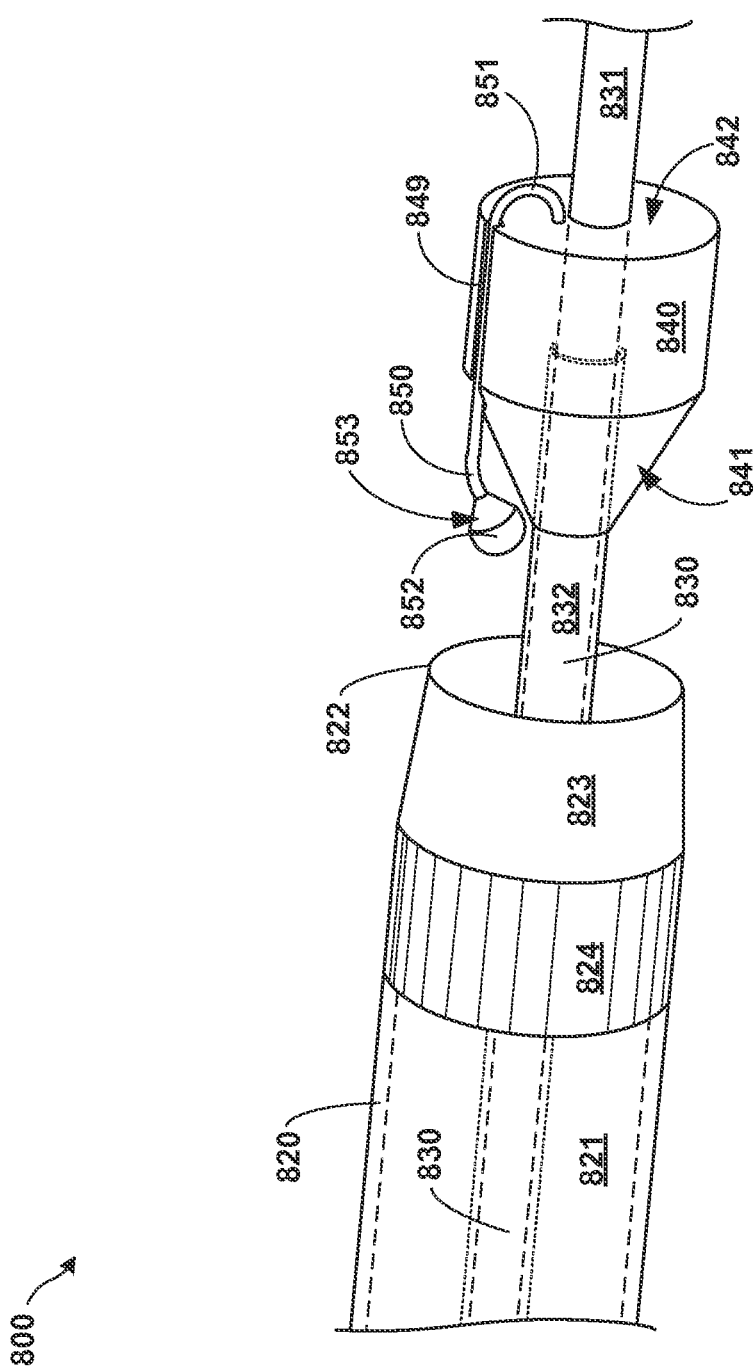
FIGS. 22-24C illustrate example techniques for intravascular delivery of an IMD using a delivery catheter that includes a tether forming a loop to engage a looped element of the IMD.
Figure 23C:
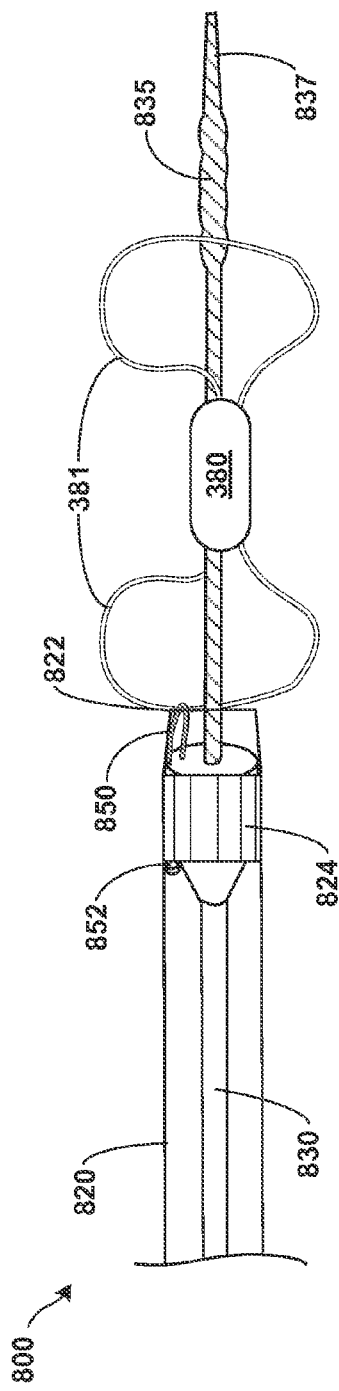
Figure 23D:
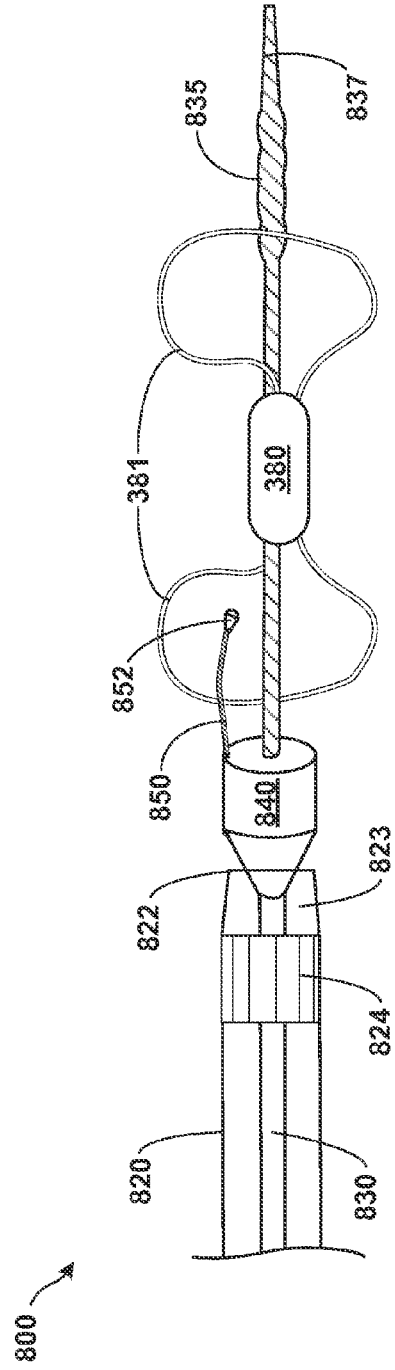
Figure 24A:
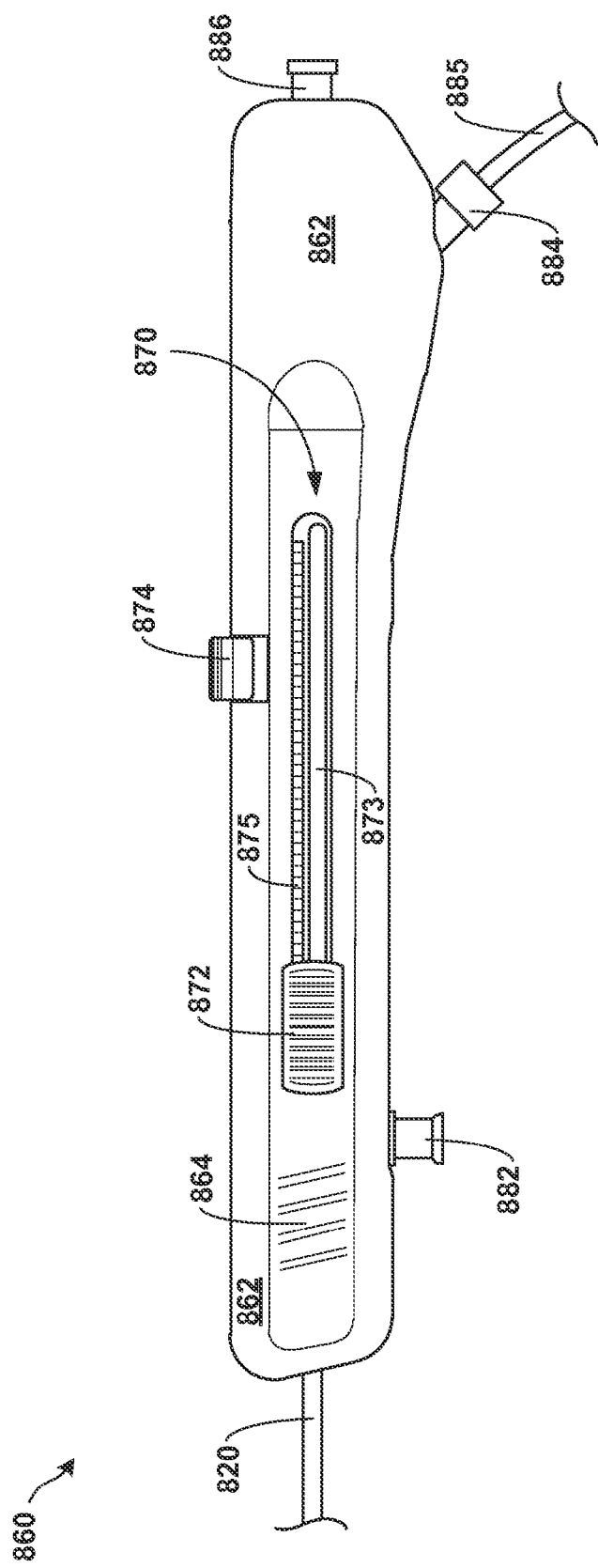

FIGS. 22-24C illustrate example techniques for intravascular delivery of IMD 380 using delivery catheter 800. Delivery catheter 800 includes tether 850, which forms loop 851 to engage a looped element of the IMD 380, such as an expandable fixation element of IMD 380. FIG. 22 illustrates a portion of delivery catheter 800 near the distal end of delivery catheter 800 whereas FIGS. 23A-23D illustrate deployment of IMD 380 from the distal end of delivery catheter 800. FIGS. 24A-24C illustrate deployment handle 860 at the proximal end of delivery catheter 800. Deployment handle 860 may be operated by a clinician during an implantation procedure to remotely deploy IMD 380 from the distal end of delivery catheter 800 as shown in FIGS. 23A-23D. In particular, deployment handle 860 may be used to retract outer sheath 820 to expose IMD 380 while inner sheath 830 holds IMD 380 at a target location within the patient.

As shown in FIG. 22, delivery catheter 800 includes elongated outer sheath 820 forming inner lumen 821 with distal opening 822. Outer sheath 820 is sized to traverse a vasculature of the patient. Delivery catheter 800 further includes elongated inner sheath 830. Elongated inner sheath 830 includes stopper 840, which is configured to engage a proximal side of IMD 380 to preclude IMD 380 from being located at a more proximal position than stopper 840 within inner lumen 821 of outer sheath 820. In one example, stopper 840 may substantially fill inner lumen 821 of outer sheath 820. In different examples, distal side 842 of stopper 840 may have a concave shape or be substantially flat.

Inner sheath 830 further includes tether 850, which is configured to form loop 851 on distal side 842 of stopper 840. Loop 851 is configured to engage a looped element of IMD 380 (not shown in FIG. 22) to couple IMD 380 to inner sheath 830. In different examples, tether 850 may be formed from a suture-like thread material or from a shape memory alloy such as Nitinol.

As described in further detail with respect to FIGS. 23A-24C, inner sheath 830 and stopper 840 are slidable relative to outer sheath 820. In particular, stopper 840 is slidable between a position that is proximally located relative to distal opening 822 of outer sheath 820 and a position in which at least a portion of stopper 840 is distally located relative to distal opening 822 of outer sheath 820. In one example, while positioning the distal end of catheter 800 proximate a target site within a vasculature of a patient during an implantation procedure, stopper 840 may be located entirely within inner lumen 821 of outer sheath 820 such that IMD 380 fits within inner lumen 821 of outer sheath 820 at a position distal to the position of stopper 840 within inner lumen 821 of outer sheath 820. Further, tether 850 forms loop 851 on distal side 842 of stopper 840. Loop 851 engages a looped element of IMD 380 (not shown in FIG. 22) to couple IMD 380 to inner sheath 830 during the positioning of the distal end of catheter 800 proximate the target site within the vasculature of the patient during the implantation procedure.

During the implantation procedure, one the distal end of catheter 800 is positioned proximate the target site within the vasculature of the patient, the clinician may partially retract outer sheath 820 to expose IMD 380, but tether remains engaged with the looped element of IMD 380. If the clinician is satisfied with the position of IMD 380, the clinician may then further retract outer sheath 820 such that at least a portion of stopper 840 is distally located relative to distal opening 822 of outer sheath 820. When stopper is located in this position, tether 850 releases the looped element of IMD 380.

Specifically, one end of tether 850 is fixed to stopper 840 and the second end of tether 850 includes bead 852. When tether 850 forms the loop, bead 852 is located within inner lumen 821 of outer sheath 820 proximal to stopper 840. In this position, bead 852 is pinched between an inner surface of outer sheath 820 and a proximal side of stopper 840. Retracting outer sheath 820 such that at least a portion of stopper 840 is distally located relative to distal opening 822 of outer sheath 820 serves to free bead 852 from between an inner surface of outer sheath 820 and the proximal tapered surface of stopper 840 to open lopped 851.

In the example shown in FIG. 22, the proximal side of stopper 840 is tapered from an inner diameter to an outer diameter of stopper 840. Bead 852 provides a tapered profile configured to register with the taper of the proximal side of stopper 840 and the inner surface of the outer sheath 820. The tapered profile of bead 852 may mitigate binding between outer sheath 820, bead 852 and stopper 840 as compared to a bead having a different shape, such as a sphere shape. As also shown in the example shown in FIG. 22, stopper 840 includes groove 849 adjacent to outer sheath 820. Groove 849 is configured to receive tether 850 when tether 850 forms loop 851. This may further mitigate binding, i.e., binding between outer sheath 820, tether 850 and stopper 840.

As shown in FIG. 22, inner sheath 830 includes inner shaft 831, which extends from a proximal end of inner sheath 830 to a distal end of inner sheath 830 including through stopper 840. Inner sheath 830 further includes outer shaft 832 that extends from the proximal end of inner sheath 830 to a position within stopper 840 such that a distal end of outer shaft 832 is within stopper 840. In an example, outer shaft 832 is shrink tubing formed over inner sheath 830. In one example, stopper 840 is an overmold that encapsulates the distal end of outer shaft 832 and a portion of inner shaft 831 to fix the position of outer shaft 832 relative to inner shaft 831.

Outer shaft 832 provides stiffness to inner sheath 830 between the proximal end of inner sheath 830 and stopper 840. The stiffness provided by shaft 832 may mitigate buckling of inner sheath 830 during an implantation procedure. Meanwhile the configuration of inner sheath 830 provides a smaller diameter distal to stopper 840, which increases the space available for IMD 380 within inner lumen 821 of outer sheath 820, and reduces the outer diameter of outer sheath 820 needed for outer sheath 820 to contain both inner sheath 830 and IMD 380 within the distal portion of inner lumen 821.

As one example, the inner diameter of outer sheath 820 may be 13 French (0.13 inches) or less and the outer diameter of outer sheath 820 may be about 3 French (0.03 inches) greater than the inner diameter of outer sheath 820, i.e., 16 French or less. In some examples, the body portion of IMD 380 including a sensor may have a cross-sectional thickness of about 10 French (0.10 inches) and the entirety of IMD 380 including fixation element 381 may provide a cross-sectional profile thickness of about 12 French (0.12 inches) when fixation element 381 is in a fully-collapsed position. In an alternative configuration, a delivery catheter similar to delivery catheter 800 may be modified to be tipless, i.e., without enlarged distal portion 835. In such a configuration, inner sheath 830 would terminate at stopper 840, and the diameter of outer sheath 820 could be further reduced as the distal portion of inner lumen 821 would only have to be large enough to contain IMD 380 and not also contain inner shaft 831. The dimensions provided herein are merely examples, and the particular sizes of the components discussed herein may be modified to account for different size IMDs and/or different target sites and access routes within a patient.

FIGS. 23A-24C illustrate exemplary techniques for intravascular delivery of IMD 380 using delivery catheter 800. FIGS. 23A-23D illustrate deployment of IMD 380 from the distal end of delivery catheter 800, whereas FIGS. 24A-24C illustrate deployment handle 860 at the proximal end of delivery catheter 800. Delivery catheter 800 includes elongated outer sheath 820 and elongated inner sheath 830 in a substantially coaxial arrangement. Elongated outer sheath 820 and elongated inner sheath 830 each extend from deployment handle 860 to the distal end of delivery catheter 800. Delivery catheter 800 and outer sheath 820 are sized to traverse a vasculature of the patient, and delivery catheter 800 is configured to carry IMD 380 within a distal portion of inner lumen 821 of outer sheath 820 while traversing the vasculature of the patient. Inner sheath 830 is slidable within outer sheath 820 and includes enlarged distal portion 835 and tether 850. Enlarged distal portion 835 provides an inflatable member and flexible tapered tip 837, e.g., as described with respect to FIG. 14. In other examples, a tapered distal end, e.g., as described with respect to FIGS. 15A-15F may be used in place of the inflatable member. In some examples, inner sheath 830 and enlarged distal portion 835 may include a lumen (not shown) configured to receive a guidewire and/or deliver contrast injections during an implantation procedure.

IMD 380 includes expandable fixation element 381, which is deployable from a collapsed position to an expanded position secure the IMD 380 proximate a target site within a patient. While FIGS. 23A-23D illustrate implantation techniques using IMD 380, in different examples, IMD 380 may be substantially similar to IMD 17 (FIG. 8) or IMD 15 (FIG. 8). As one example, the techniques of FIGS. 23A-24C may be used to deliver IMD 17 to a position within a heart of a patient, such as a position proximate to an inner wall of the right ventricle, within the right atrium, the left atrium, and/or left ventricle. As another example, the techniques of FIGS. 23A-24C may be used to deliver IMD 15 to an intravascular position such as a pulmonary artery or other vasculature of the patient.

During an implantation procedure, a clinician first positions delivery catheter 800 such that the distal end of outer sheath 820 is proximate to a target site within the patient via a vasculature accessed during a surgical procedure, as represented by FIG. 23A. For example, delivery catheter 800 may be advanced into an entry vessel, such as the femoral artery, and then manipulated and navigated through the patient's vasculature until the distal end of outer sheath 820 proximate to a target site within the patient. In different examples, delivery catheter 800 may be steerable or be configured to traverse a guidewire to be directed to the target site from the access point of the vasculature. The clinician may use imaging techniques, such as fluoroscopy, to monitor the position of outer sheath 820, inner sheath 830, and IMD 380 throughout the implantation procedure. As shown in FIG. 22, outer sheath 820 includes marker band 824, which is visible to the clinician during imaging. As one example, marker band 824 may be a gold band. Bead 852 and/or stopper 840 may also include radiopaque materials to aid in visibility of catheter 800 during an implantation procedure. In some examples, bead 852 and stopper 840 may have different radiopaque materials such that bead 852 and stopper 840 such that a clinician can clearly distinguish bead 852 and stopper 840 from one another during imaging. In further examples, delivery catheter 800 may have an internal lumen for contrast injections. As one example, the internal lumen for contrast injections may be a guidewire lumen.

Enlarged distal portion 835 is configured to substantially fill inner lumen 821 of outer sheath 820 and close-off distal opening 822 of outer sheath 820 when inflated, for example, while delivery catheter 800 is advanced to a location proximate a target site within a patient.

After positioning the distal end of outer sheath 820 is proximate to the target site within the patient, the clinician operates deployment handle 860 (FIGS. 24A-24C) to deploy IMD 380. As shown in FIG. 24A, deployment handle is located at the proximal end of outer sheath 820 and inner sheath 830 (not indicated in FIG. 24A). Deployment handle 860 includes sheath retraction mechanism 870, which facilitates selectively retracting outer sheath 820 relative to inner sheath 830 to facilitate remote deployment of IMD 380 out of the distal opening of the inner lumen of the outer sheath.

Deployment handle 860 includes body 862, which forms grip surfaces 864 to improve the controllability of deployment handle 860 by a clinician. Sheath retraction mechanism 870 includes slidable deployment button 872, which is configured to selectively retract outer sheath 820 relative to inner sheath 830 when moved from a distal position on body 862 (as shown in FIG. 24A) to a more proximal position on the body (as shown in FIGS. 24B and 24C). Deployment button 872 may be directly coupled to outer sheath 820, whereas body 862 may be directly coupled to inner sheath 830 via guidewire port 886. Body 862 includes slot 873, which allows slidable deployment button 872 to be outside body 862 while being connected to outer sheath 820. Sheath retraction mechanism 870 further includes positive stops 875, which individually register with deployment button 872 such that a clinician can incrementally retract outer sheath 820 if desired.

Deployment handle 860 further includes partial deployment lock button 874. Partial deployment lock button 874 is configured to selectively prevent deployment button 872 from being moved to a position configured to fully release the IMD 380 from the inner sheath, i.e., a position in which bead 852 is released to open loop 851.

As mentioned above, deployment handle 860 includes guidewire port 886. Inner sheath 830 includes a guidewire lumen (not shown) extending throughout the length of inner sheath 830, the guidewire lumen being configured to slidably receive a guidewire. Guidewire port 886 is in substantial alignment with the guidewire lumen of inner sheath 830. Guidewire port 886 facilitates removal of a guidewire from within the guidewire lumen by pulling the guidewire proximally out of guidewire port 886 and the guidewire lumen of inner sheath 830. In some examples, guidewire port 886 may include a one-way valve to prevent patient fluids from flowing through guidewire lumen of inner sheath 830 and out of guidewire port 886 once the distal end of catheter 800 is inserted within a patient.

Deployment handle 860 further includes flushing check valve 882. Flushing check valve 882 is a one-way valve that facilitates flushing outer sheath 820 to remove air from within outer sheath 820 prior to inserting the distal end of catheter 800 within a patient to mitigate a risk of emboli within the patient. The one-way configuration of check valve 882 also serves to prevent patient fluids from flowing through inner lumen 821 of outer sheath 820 and out of check valve 882 once the distal end of catheter 800 is inserted within a patient.

Deployment handle 860 further includes inflation port 884, which is configured to exchange an inflation media via inflation media tube 885. The inflation port is used to selectively inflate inflatable member 835 on the distal end of inner sheath 830.

As mentioned previously, after positioning the distal end of outer sheath 820 is proximate to the target site within the patient, as represented by FIG. 23A, the clinician evaluates inflation media from inflatable member 835 via inflation port 884 deployment handle 860, as represented by FIG. 23B.

Then the clinician operates deployment handle 860 to deploy IMD 380. As shown in FIG. 24A, slidable deployment button 872 is in its most distal position, which coincides with the distal end of outer sheath 820 being in its most distal position as shown in FIGS. 23A and 23B. From this position, the clinician moves slidable deployment button 872 in a proximal direction relative to body 862 of deployment handle 860 as represented by FIG. 24B. This retracts outer sheath 820 relative to inner sheath 830 such that stopper 840 of pushes IMD 380 out of distal opening 822 of outer sheath 820 as represented by FIG. 23C. However, because the position of inner sheath 830 has been maintained within the patient while outer sheath 820 is retracted, the position of IMD 380 is also maintained within the patient while outer sheath 820 is retracted. In this manner, retracting outer sheath 820 rather than extending inner sheath 830 to push IMD 380 out of distal opening 822 of outer sheath 820 allows a clinician to locate IMD 380 at a target deployment site before IMD 380 is actually deployed.

As shown in FIG. 23C, all or a portion of expandable fixation element 381 of IMD 380 is expanded from a collapsed position to an expanded position as IMD 380 passes out of distal opening 822 of the distal end of outer sheath 820. In the expanded position, expandable fixation element 381 will secure IMD 380 within the patient, e.g., as described with respect to IMD 17 (FIG. 4) or IMD 15 (FIG. 8).

Partial deployment lock button 874 of deployment handle 860 selectively prevents deployment button 872 from being moved to a position configured to fully-release IMD 380 from inner sheath 830, i.e., a position in which bead 852 is released to open loop 851. As shown in FIG. 24B, partial deployment lock button 874 is engaged prevents slidable deployment button 872 from moving further in a proximal direction.

If a clinician is not satisfied with the position of IMD 380 after partial deployment, as represented by FIG. 23C and FIG. 24B, the clinician may advance outer sheath 820 relative to inner sheath 830 by moving deployment button 872 to its distal position as shown in FIG. 24A. This relocates IMD 380 within inner lumen 821 of outer sheath 820 via distal opening 822 of outer sheath 820. The clinician may then optionally redeploy IMD 380, e.g., at a different position within the patient.

Once a clinician is satisfied with the position of IMD 380 after partial deployment, as represented by FIG. 23C and FIG. 24B, the clinician may open partial deployment lock button 874 and move deployment button 872 to a more proximal position as represented by FIG. 24C. This further retracts outer sheath 820 in a more proximal direction relative to inner sheath 830 such that stopper 840 is positioned distally relative to distal opening 822 of outer sheath 820 to open tether loop 851 by releasing bead 852 and release expandable fixation element 381, a looped element of IMD 380, from inner sheath 830 as represented by FIG. 23D to fully deploy IMD 380. Once IMD 380 is fully deployed, a clinician may withdraw catheter 800 from the patient.

While deployment handle 860 has been described specifically with respect to catheter 800, the techniques disclosed with respect to deployment handle 860 may also be used with a variety of alternate catheter designs, including those disclosed herein.

Various examples of the disclosure have been described. These and other examples are within the scope of the following claims.

The invention claimed is:

1. A method for intravascular implantation of an implantable medical device within a patient comprising:
positioning a distal end of an elongated outer sheath forming an inner lumen with a distal opening adjacent a target site within a vasculature of the patient;
partially deploying the implantable medical device from the distal opening, wherein the implantable medical device includes an expandable fixation element with a looped element expandable from a collapsed position to an expanded position, wherein, in the expanded position, the looped element is configured to simultaneously contact opposite sides of the interior of the vasculature to secure the implantable medical device within the vasculature, wherein at least a portion of the expandable fixation element assumes the expanded position when the implantable medical device is partially deployed from the distal opening;
advancing the distal end of the outer sheath within the vasculature with the implantable medical device partially deployed from the distal opening; and
monitoring at least one of the vasculature and the portion of the expandable fixation element for deflection to determine when a size of the portion of the expandable fixation element corresponds to a size of the vasculature.

2. The method of claim 1, wherein monitoring at least one of the vasculature and the portion of the expandable fixation element for deflection comprises using fluoroscopy to view at least one of the vasculature and the portion of the expandable fixation element while advancing the distal end of the outer sheath within the vasculature.

3. The method of claim 1, further comprising injecting a contrast dye within the vasculature while monitoring at least one of the vasculature and the portion of the expandable fixation element for deflection.

4. The method of claim 1,
wherein the inner lumen is a first inner lumen,
wherein the outer sheath is part of an assembly including an elongated inner sheath within the first inner lumen, wherein positioning the distal end of the outer sheath adjacent the target site within the vasculature includes positioning a distal end of assembly adjacent the target site within the vasculature,
wherein the inner sheath forms a second inner lumen, wherein an outer diameter of the inner sheath is smaller than a diameter of the first inner lumen such that the inner sheath fits within the first inner lumen, wherein the inner sheath is slidable within the first inner lumen,
wherein the implantable medical device is carried within the second inner lumen at a distal end of the inner sheath,
wherein the inner sheath forms a slit at the distal end of the inner sheath, adjacent a distal opening of the second inner lumen, to facilitate deployment of the implantable medical device out of the distal opening of the first inner lumen of the outer sheath,
wherein partially deploying the implantable medical device from the distal opening comprises sliding the distal end of the inner sheath out of the first inner lumen to expose a portion of the inner sheath and at least a portion of the implantable medical device out of the distal end of the outer sheath.

5. The method of claim 4, wherein the distal end of the inner sheath is elastically deformed within the first inner lumen such that the distal end of the inner sheath uncurls to expose the implantable medical device when the distal end of the inner sheath passes out of the distal opening of the first inner lumen of the outer sheath.

6. The method of claim 4, wherein at least a portion of the expandable fixation element assumes the expanded position when the distal end of the inner sheath passes out of the distal opening of the first inner lumen of the outer sheath.

7. The method of claim 6, further comprising deploying the implantable medical device from the inner sheath by retracting the inner sheath into the outer sheath after the portion of the expandable fixation element assumes the expanded position such that the distal end of the outer sheath interacts with the expandable fixation element to slide the implantable medical device out of the second inner lumen.

8. The method of claim 4, the method further comprising retracting the inner sheath into the outer sheath to return the implantable medical device to the first inner lumen.

9. The method of claim 8, wherein retracting the implantable medical device by retracting the inner sheath into the outer sheath causes the portion of the expandable fixation element to resume the collapsed position within the second inner lumen.

10. The method of claim 1, further comprising positioning an elongated deployment receptacle within the inner lumen of the outer sheath,
wherein the deployment receptacle includes a deployment bay at a distal end of the deployment receptacle, wherein the deployment receptacle is slidable within the inner lumen of the outer sheath, wherein the deployment bay carries the implantable medical device and facilitates deployment of the implantable medical device out of the distal opening of the inner lumen of the outer sheath.

11. The method of claim 10, wherein the deployment receptacle further comprises a tether that is remotely controllable from a proximal end of the deployment receptacle to release the implantable medical device from the deployment bay, the method further comprising remotely controlling the tether to deploy the implantable medical device from the deployment bay.

12. The method of claim 11, wherein the tether includes a helical element, wherein remotely controlling the tether to deploy the implantable medical device from the deployment bay includes rotating the helical element such that the helical element releases the looped element of the implantable medical device.

13. The method of claim 12, wherein partially deploying the implantable medical device from the distal opening includes pushing the implantable medical device out of the deployment bay with the helical element while the helical element remains attached to the looped element of the implantable medical device.

14. The method of claim 12, wherein partially deploying the implantable medical device from the distal opening includes pushing the implantable medical device out of the deployment bay while the helical element remains attached to the looped element of the implantable medical device.

15. The method of claim 14, wherein the looped element of the implantable medical device is part of the expandable fixation element.

16. The method of claim 1, wherein the implantable medical device includes at least one sensor selected from a group consisting of:
a pressure sensor;
an electrocardiogram sensor;
a fluid flow sensor;
an oxygen sensor;
an accelerometer;
a glucose sensor;
a potassium sensor; and
a thermometer.

17. The method of claim 1, wherein the target site is within a pulmonary artery of the patient.

18. The method of claim 17, wherein the implantable medical device includes a pressure sensor.

19. The method of claim 1, wherein the implantable medical device includes a pressure sensor, the method further comprising:
monitoring pressure within the vasculature with the pressure sensor with the implantable medical device partially deployed from the distal opening to test the functionality of implantable medical device at that location; and after verifying functionality of implantable medical device at that location, fully releasing the implantable medical device to deploy the implantable medical device within the vasculature.

20. The method of claim 19, further comprising receiving an indication of the monitored pressure from the implantable medical device with an external programmer.

21. The method of claim 1, wherein the looped element forms an aperture that allows blood flow through the vasculature.

* * * * *